(12) United States Patent
Dugar et al.

(10) Patent No.: US 10,618,933 B2
(45) Date of Patent: Apr. 14, 2020

(54) HYDROXYSTEROID COMPOUNDS, THEIR INTERMEDIATES, PROCESS OF PREPARATION, COMPOSITION AND USES THEREOF

(71) Applicant: Epirium Bio Inc., San Diego, CA (US)

(72) Inventors: Sundeep Dugar, San Jose, CA (US); Dinesh Mahajan, Haryana (IN); George Frederic Schreiner, Los Altos Hills, CA (US)

(73) Assignee: EPIRIUM BIO INC., San Diego, CA (US)

( * ) Notice: Subject to any disclaimer, the term of this patent is extended or adjusted under 35 U.S.C. 154(b) by 0 days.

(21) Appl. No.: 15/327,545

(22) PCT Filed: Jul. 23, 2015

(86) PCT No.: PCT/IN2015/050072
§ 371 (c)(1),
(2) Date: Jan. 19, 2017

(87) PCT Pub. No.: WO2016/013030
PCT Pub. Date: Jan. 28, 2016

(65) Prior Publication Data
US 2017/0158730 A1 Jun. 8, 2017

(30) Foreign Application Priority Data

Jul. 23, 2014 (IN) .............................. 2085/DEL/2014
Jul. 23, 2014 (IN) .............................. 2086/DEL/2014

(51) Int. Cl.
| | | |
|---|---|---|
| C07J 73/00 | (2006.01) | |
| C07J 1/00 | (2006.01) | |
| C07J 41/00 | (2006.01) | |
| C07J 51/00 | (2006.01) | |
| C07J 43/00 | (2006.01) | |
| C07J 17/00 | (2006.01) | |
| C07J 9/00 | (2006.01) | |
| C07J 7/00 | (2006.01) | |
| C07J 3/00 | (2006.01) | |

(52) U.S. Cl.
CPC ............ *C07J 73/005* (2013.01); *C07J 1/004* (2013.01); *C07J 1/0007* (2013.01); *C07J 1/007* (2013.01); *C07J 1/0011* (2013.01); *C07J 1/0022* (2013.01); *C07J 1/0037* (2013.01); *C07J 1/0051* (2013.01); *C07J 1/0055* (2013.01); *C07J 1/0085* (2013.01); *C07J 3/00* (2013.01); *C07J 3/005* (2013.01); *C07J 7/002* (2013.01); *C07J 7/005* (2013.01); *C07J 7/007* (2013.01); *C07J 9/00* (2013.01); *C07J 17/00* (2013.01); *C07J 41/0011* (2013.01); *C07J 41/0016* (2013.01); *C07J 41/0038* (2013.01); *C07J 41/0044* (2013.01); *C07J 41/0066* (2013.01); *C07J 41/0072* (2013.01); *C07J 41/0088* (2013.01); *C07J 43/003* (2013.01); *C07J 51/00* (2013.01)

(58) Field of Classification Search
CPC .... C07J 73/005; C07J 1/0051; C07J 41/0066; C07J 1/0007; C07J 1/004; C07J 41/0044; C07J 7/005; C07J 51/00; C07J 41/0072; C07J 41/0038; C07J 41/0016; C07J 41/0011; C07J 1/0011; C07J 9/00; C07J 7/007; C07J 43/003; C07J 7/002; C07J 3/005; C07J 3/00; C07J 1/0085; C07J 1/007; C07J 1/0055; C07J 1/0037; C07J 1/0022; C07J 17/00; C07J 41/0088
See application file for complete search history.

(56) References Cited

U.S. PATENT DOCUMENTS

| | | | |
|---|---|---|---|
| 2,341,250 | A | 2/1944 | Wallis |
| 2,763,645 | A | 9/1956 | Bloom |
| 2,767,155 | A | 10/1956 | Oliveto |
| 2,989,550 | A | 6/1961 | Nathan |
| 3,657,226 | A | 4/1972 | Lefebvre |
| 4,334,067 | A | 6/1982 | Ohno |

(Continued)

FOREIGN PATENT DOCUMENTS

| | | |
|---|---|---|
| CN | 102612564 A | 7/2012 |
| CN | 105073119 A | 11/2015 |

(Continued)

OTHER PUBLICATIONS

Andrushina, V. A., "Hydroxylation of steroids by Curvularia lunata mycelium in the presence of methyl-β-cyclodextrine." Applied biochemistry and microbiology 47.1 (2011): 42-48.*

Caspi, E., "Degradation of Corticosteroids. V. Preparation and Certain Reactions of 11-Oxygenated-3, 5-seco-4-nor-5β-hydroxy-3-oic Acid 3, 5-Lactones1a, b, 2." The Journal of Organic Chemistry 26.10 (1961): 3898-3903. (Year: 1961).*

Ito, N., "A medium-term rat liver bioassay for rapid in vivo detection of carcinogenic potential of chemicals." Cancer science 94.1 (2003): 3-8. (Year: 2003).*

(Continued)

*Primary Examiner* — John M Mauro
(74) *Attorney, Agent, or Firm* — Morrison & Foerster LLP

(57) ABSTRACT

The present invention relates to novel steroidal compounds of formula (I), process for preparation of the same and composition comprising these compounds.

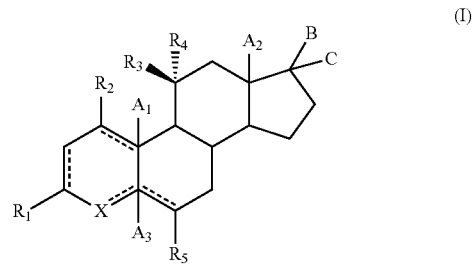

(I)

14 Claims, 5 Drawing Sheets

(56) References Cited

U.S. PATENT DOCUMENTS

| | | | |
|---|---|---|---|
| 4,996,335 | A | 2/1991 | Bodor |
| 5,215,894 | A | 6/1993 | Arison et al. |
| 6,410,052 | B1 | 6/2002 | Morre |
| 7,309,715 | B2 | 12/2007 | Vicker |
| 2006/0148725 | A1 | 7/2006 | Morris |
| 2009/0280525 | A1 | 11/2009 | Gupta |
| 2010/0048920 | A1 | 2/2010 | Romanczyk, Jr. |
| 2010/0260733 | A1 | 10/2010 | Qi |
| 2010/0266523 | A1 | 10/2010 | Vercauteren |
| 2015/0376225 | A1 | 12/2015 | Dugar |

FOREIGN PATENT DOCUMENTS

| | | | |
|---|---|---|---|
| EP | 1336602 | A1 | 8/2003 |
| EP | 2948152 | A2 | 12/2015 |
| GB | 2264494 | A | 9/1993 |
| JP | 05170789 | * | 7/1993 |
| JP | 2016505038 | A | 2/2016 |
| WO | WO1988002753 | A3 | 4/1988 |
| WO | WO198903390 | A1 | 4/1989 |
| WO | WO199518621 | A1 | 7/1995 |
| WO | WO1988002753 | A2 | 4/1998 |
| WO | WO1999032102 | A1 | 7/1999 |
| WO | WO2003101927 | A1 | 12/2003 |
| WO | WO2004037251 | A1 | 5/2004 |
| WO | WO2004097002 | A2 | 11/2004 |
| WO | WO2004097002 | A3 | 6/2005 |
| WO | WO2006058781 | A2 | 6/2006 |
| WO | WO2006058781 | A3 | 3/2007 |
| WO | WO2007058971 | A2 | 5/2007 |
| WO | WO2007058971 | A3 | 7/2007 |
| WO | WO2007103162 | A2 | 9/2007 |
| WO | WO2007103162 | A3 | 12/2008 |
| WO | WO2009085879 | A2 | 7/2009 |
| WO | WO2010118419 | A2 | 10/2010 |
| WO | WO2010121232 | A1 | 10/2010 |
| WO | WO2010118419 | A3 | 2/2011 |
| WO | WO2012101652 | A2 | 8/2012 |
| WO | WO2012101652 | A3 | 12/2012 |
| WO | WO2013020979 | A1 | 2/2013 |
| WO | WO2013022846 | A2 | 2/2013 |
| WO | WO2013121232 | A1 | 8/2013 |
| WO | WO2013022846 | A3 | 10/2013 |
| WO | WO2014115167 | A2 | 7/2014 |
| WO | WO2014115167 | A3 | 12/2014 |
| WO | WO2016013030 | A2 | 1/2016 |
| WO | WO2016013030 | A3 | 1/2016 |
| WO | WO2017221269 | A1 | 12/2017 |
| WO | WO2018083713 | A1 | 5/2018 |

OTHER PUBLICATIONS

JP 05170789, English Machine Translation, ProQuest Dialog Sep. 8, 2017; p. 1-86. (Year: 2003).*

JP 01570789 WIPO English machine translation May 2018; p. 1-74.*

CAS Registry No. 152398-87-3 Scifinder Entry Sep. 2018; p. 1.*

Allen, W.S. et al. (Jan. 1962). "Certain Steroid Ketals and Their Biological Activity," Journal of Medicinal and Pharmaceutical Chemistry 5(1):133-155.

Apsimon, J.W. et al. (1974). "Marine Organic Chemistry. II. Synthesis of 3β,6α-Dihydroxy-5α Pregn-9(11)-en-20-one, The Major Sapogenin of the Starfish Asterias forbesi" Canadian Journal of Chemistry 52(24):4113-4116.

Bellomo, R. et al. (May 24, 2004). "Acute Renal Failure—Definition, Outcome Measures, Animal Models, Fluid Therapy and Information Technology Needs: The Second International Consensus Conference of The Acute Dialysis Quality Initiative (ADQI) Group," Crit Care 8(4):R204-R212.

Bergstrom, C.G. (Jul. 1968). "The Synthesis and Biological Evaluation of 16.Beta.-Amino-17.Alpha.-Hydroxy-20-Oxopregnenes," J. Med. Chem. 11(4):875-879.

Brown, B.R. et al. (1974). "Reactions of Flavanoids and Condensed Tannins With Sulphur Nucleophiles," J. Chemical Society, Perkin Transaction pp. 2036-2019 14 pages.

CAS Registry No. 600-57-7, entered STN: Nov. 16, 1984.

Caspi, E. (Oct. 1961). "Degradation of Corticosteroids. V. Preparation and Certain Reactions of 11-Oxygenated-3,5-seco-4-nor-5β-hydroxy-3-oic Acid 3, 5-Lactones 1a, b,2," The Journal of Organic Chemistry 26 (10):3898-3903.

Cark-Lewis, J.W. et al. (1973). "Chemistry of 3-oxoflavans: Oxidation of (+)-Catechin 5,7,3',4'-Tetramethyl Ether to (+)-5,7,3',4'-Teramethoxy-3-Oxoflavan," Australian Journal of Chemistry 26(12):2675-2682.

Druzgala, P. et al. (Sep. 1991). "Regioselective O-Alkylation of Cortienic Acid and Synthesis of a New Class of Glucocorticoids Containing a 17α-alkoxy, a 17α-(1'-alkoxyethyloxy), a 17α-alkoxymethyloxy, or a 17α-methylthiomethyloxy Function," Steroids 56:490-494.

Fang, H. et al. (2001, e-pub. Feb. 10, 2001). "Structure-Activity Relationships for a Large Diverse Set of Natural, Synthetic, and Environmental Estrogens," Chem. Res. Toxicol. 14:280-294.

Fiet, J. et al. (Mar. 1989). "Increased Plasma 21-Deoxycorticosterone (21-DB) Levels in Late-Onset Adrenal 21-Hydroxylase Deficiency Suggest a Mild Defect of the Mineralocorticoid Pathway," Journal of Clinical Endocrinology and Metabolism 68(3):542-547.

Gohil, V.M. et al. (Mar. 2010, e-pub. Feb. 14, 2010). "Discovery and Therapeutic Potential of Drugs That Shift Energy Metabolism From Mitochondrial Respiration to Glycolysis," Nature Biotechnol. 28(3):249-257.

International Preliminary Report on Patentability, dated Jan. 24, 2017, for PCT Application No. PCT/IN2015/050072, filed Jan. 23, 2015, 7 pages.

International Preliminary Report on Patentability, dated Jul. 28, 2015, for PCT Application No. PCT/IN2014/000048, filed Jan. 23, 2014, 7 pages.

International Search Report, dated Jan. 14, 2016, for PCT Application No. PCT/IN2015/050072, filed Jan. 23, 2015, 3 pages.

International Search Report, dated Oct. 7, 2014, for PCT Application No. PCT/IN2014/000048, filed Jan. 23, 2014, 3 pages.

Ishibashi, K. et al. (Jul. 9, 1993). "Preparation of 4-Azazteroids as Testosterone 5.α.Reductase Inhibitors," Accession No. 1768, 4 pages.

Li, Z. et al. (Dec. 15, 2008, e-pub. Oct. 11, 2008). "Synthesis of a Library of Glycosylated Flavonols," Tetrahedron Letters 49(51):7243-7245.

Maloney, D.J. et al. (2005). "(+)-Myristinin A, a Naturally Occurring DNA Polymerase β Inhibitor and Potent DNA-Damaging Agent," J. Am. Chem. Soc.127(12):4140-4141.

Manz, B. et al. (1982). "Steroid Side-Chain Modification and Receptor Affinity: Binding of Synthetic Derivatives of Corticoids to Human Spleen Tumor and Rat Liver Glucocorticoid Receptors," J. Steroid Biochem. 17(3):335-342.

Nakken, G.N. et al. (2010, e-pub. Dec. 3, 2009). "Effects of Excess Corticosterone on LKB1 and AMPK Signaling in Rat Skeletal Muscle," J Appl. Physiol 108(2):298-305.

Oliver M.H. et al. (1989). "A Rapid and Convenient Assay for Counting Cells Cultured in Microwell Plates: Application for Assessment of Growth Factors," J Cell Sci. 3:513-518.

Pereira, C.V. et al. (2009). "Investigating Drug-induced Mitochondrial Toxicity: A Biosensor to Increase Drug Safety?" Current Drug Safety 4(1):1-22.

Prieur, B. et al. (Mar. 1, 1998). "Effects of Adrenal Steroid Hormones on Mitochondrial Maturation During the Late Fetal Period," European Journal of Biochemistry 252(2):194-199.

Rosenkranz, G. et al. (Feb. 1, 1952). "Steroids. XXIX.1 Synthesis of 11β-Hydroxyprogesterone," Journal of Organic Chemistry 17(2):290-293.

Sandham, D.A. et. al. (Oct. 1, 2004, e-pub. Aug. 4, 2004). "Synthesis and Biological Properties of Novel Glucocorticoid Androstene C-17 Furoate Esters," Bioorg. Med. Chem. 12(19):5213-5224.

Shimizu, H. et al. (Sep. 1, 2008). "Glucocorticoids Increase Neuropeptide Y and Agouti-Related Peptide Gene Expression via Adenosine Monophosphate-Activated Protein Kinase Signaling in the Arcuate Nucleus of Rats," Endocrinology 146(9):4544-4553.

(56) References Cited

OTHER PUBLICATIONS

Wagner, B.K. et al. (Mar. 2008). "Large-Scale Chemical Dissection of Mitochondrial Function," Nature Biotechnol 26(3):343-351.
Written Opinion, dated Jan. 14, 2016, for PCT Application No. PCT/IN2015/050072, filed Jan. 23, 2015, 6 pages.
Written Opinion, dated Oct. 7, 2014, for PCT Application No. PCT/IN2014/000048, filed Jan. 23, 2014, 3 pages.
Zhang, H. et al. (Oct. 31, 2001). Clinical New Drug Special Drug Manual The JinDun Publishing House Edition 1 p. 670. English Abstract.
Zhao, Y. (Jan. 29, 2008, e-pub. Nov. 26, 2007). "Chronic Corticosterone Injections Induce a Decrease of ATP Levels and Sustained Activation of AMP-Activated Protein Kinase in Hippocampal Tissues of Male Mice," Brain Research 1191:148-156.
Barreto-Torres, G. et al. (2011, e-pub. Apr. 1, 2011). "AMPK-Induced Inhibition of Mitochondrial Dysfunction is Mediated Through PPAR_Alpha in Acute Cardiac Ischemia/Reperfusion," FASEB J. 25(Supp. 1):Abstract.
Crabb, T.A. et al. (1988). "Microbiological Transformations, Part 10. Microbilogical Transformations of A-Ring Aza-Steroids With the Fungus Cunninghamella elegans: Synthesis of the 17β-Acetoxy-5-Hydroxy-4-aza-A-Homoandrostan-3-Ones," J. Chem. Research p. 207.
Crabb, T.A. et al. (1989). "Michrobiological Transformations. Part 11. Microbiological Transformations of A-Nor-, A-Homo-, and A-Ring-Heterocyclic Steroids With the Fungus *Aspergillus* ochraceus," J. Chem. Research pp. 280-281.
Ishibashi, K. et al. (1996). "Synthesis and Testosterone 5α-Reductase Inhibitory Activity of 11-Substituted 4-aza-5α-Androstane Compounds," Eur. J. Med. Chem. 31:675-681.
Lantier, L. et al. (2014). "AMPK Controls Exercise Endurance, Mitochondrial Oxidative Capacity, and Skeletal Muscle Integrity," FASEB J. 28:3211-3224.

\* cited by examiner

HYDROXYSTEROID COMPOUNDS, THEIR INTERMEDIATES, PROCESS OF PREPARATION, COMPOSITION AND USES THEREOF

FIELD OF INVENTION

The present invention relates hydroxysteroid compounds and their intermediates, composition comprising the same and method of preparation thereof and uses of the compounds of the present invention.

BACKGROUND OF THE INVENTION

Mitochondria are the powerhouses of the cell that are responsible for generating more than 90% of the energy needed by the body to sustain life and support growth. When mitochondrial function fails, less energy is generated within the cell, resulting in cell injury and ultimately cell death. Mitochondria are susceptible to degradation due to oxygen radicals produced by their own metabolic processes. Damaged mitochondria are later expelled by the cell. Their replacement by new mitochondria is called mitochondrial biogenesis. The proliferation of mitochondria or their hypertrophy to meet increased metabolic demand is also called mitochondrial biogenesis. It is signified by the expression of additional mitochondrial proteins, particularly those related to oxidative phosphorylation. The capacity for mitochondrial biogenesis is significantly lost with age. Thus many diseases of aging are associated with loss of mitochondria in various tissues, whose specialized function is diminished in the context of diminished mitochondrial function and/or number. Many disease states, such as those that have neuromuscular disease symptoms, sarcopenia, muscular dystrophy, diabetes mellitus, dementia, Parkinson's disease, Huntington's disease, amyotrophic lateral sclerosis (ALS), obesity, hyperlipidemia, heart failure, lupus, and ocular conditions such as age-related macular degeneration (AMD), are associated with progressive mitochondrial loss in various tissues. A number of drugs and drug classes also have an effect on mitochondrial function and biogenesis and can affect organ function and even lead to organ degeneration or other side effects which are directly related to the toxic effect of these drugs on the mitochondria.

Ischemic and ischemia/reperfusion injury are accompanied by decrease in mitochondrial function and number, leading to apoptotic cell death, necrosis, and functional organ deterioration in ischemic conditions such as myocardial infarction and stroke. Despite considerable advances in the diagnosis and treatment of such conditions, there remains a need for prophylactic and therapeutic approaches for the treatment of these conditions.

Compounds that have functions on mitochondrial activity are currently limited and there remains a need for novel compounds prophylactic and therapeutic approaches for the treatment of these conditions associated with chronic mitochondrial dysfunction and toxicity. Thus there is a need for compounds and treatments that stimulate mitochondrial function in response to increased metabolic demand and induce mitochondrial replication in response to agents or conditions that cause depletion of mitochondria in one or more tissues. Reflecting this understanding, the phrase "mitochondrial toxicity" as used herein refers to failure of the mitochondria resulting from the administration of chemical compositions to a subject.

Mitochondria are critical to cell function and the effects of mitochondrial disease can be varied and can take on unique characteristics. The severity of the specific defect may be great or small and often affect the operation of the mitochondria and multiple tissues more severely, leading to multi-system diseases. Injury to, or dysfunction of, skeletal muscle mitochondria generally results in muscle weakness and atrophy, termed sarcopenia in severe states. In the case of generalized muscle weakness, reduction in bone density can be generalized, one of the causes of the bone disease known as osteoporosis. Depleted mitochondria in the heart can eventuate in the symptoms of congestive heart failure and eventual death. Loss of mitochondrial density in the brain is associated with neurodegeneration states such as Huntington's disease, Alzheimer's disease, and Parkinson's disease. Generalized loss of mitochondria including liver mitochondria can result in hyperlipidemia, hypertension, and insulin resistance progression to Type 2 diabetes. Liver mitochondria are injured by fructose uptake. Fructose, uric acid, and other agents injurious to liver mitochondria can cause accumulation of intracellular lipids, particularly triglycerides that contribute to the syndrome of hepatic steatosis, and increased synthesis and export of triglycerides that contributes to systemic hyperlipidemia, and ultimately obesity and insulin resistance.

Hydroxysteroids are hydroxylated compounds with a sterol structure and are known to be produced in cells when the mitochondria are exposed to high levels of endogenous $H_2O_2$ which then acts via the mitochondrial enzyme, 11β-hydroxylase, to hydroxylate a variety of steroids, including cholesterol, pregnenolone, progesterone, and others. Hydroxylation can occur in numerous positions, including the 7, 16, and 11 positions. These molecules, termed hydroxysteroids, are then sulfated and secreted into the extracellular space, where in the brain they modulate GAB A-receptors and calcium channels on the plasma membrane. No intracellular activity of hydroxylsteroids has previously been described.

The present invention discloses novel hydroxyl steroids, their intermediates, process for synthesis of hydroxysteroids and their intermediates and composition comprising the same with their action on mitochondria.

OBJECT OF THE INVENTION

An object of the present invention is to provide novel steroidal compounds, a process for synthesis of hydroxysteroids and their intermediates and compositions comprising the same and effect of the said compounds on mitochondria.

SUMMARY OF THE INVENTION

The present invention provides hydroxysteroids and their intermediates of formula (I):

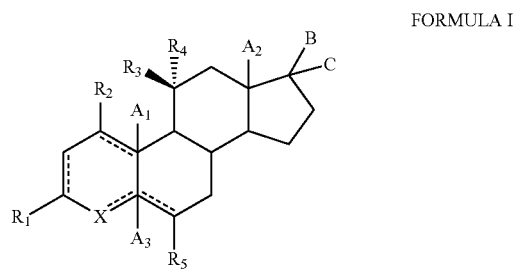

FORMULA I or a salt thereof, wherein:

is independently either a single bond, a double bond or a cyclopropyl ring, provided that adjacent double bonds are not allowed;

A₁, A₂, A₃ are independently selected from the group comprising hydrogen, hydroxyl, hydroxymethyl, halogen, $C_1$-$C_6$ alkyl;

B and C are each independently selected from the group comprising hydrogen, hydroxyl, halogen, —$OR_6$, —$COR_6$, —$COOR_6$, $OCOR_6$, $CH_2OH$, $CH_2OR_6$, —$CONHR_6$, $CONHR_6R_7$, —$C(OH)R_6R_7$, $NHR_6$, $NHR_5CONHR_6$, —$R_6NHCOOR_7$, —$NR_6R_7$, C(O)heteroaryl, C(O)heterocyclyl, $C_1$-$C_{12}$ straight or branched chain alkyl, 5-6 membered heterocycloalkyl, 5-6 membered heteroaryl;

wherein the $C_1$-$C_{12}$ straight or branched chain alkyl or 5-6 membered heterocycloalkyl or 5-6 membered heteroaryl; may be further optionally substituted with one or more substituents selected from the group comprising halogen, $C_1$-$C_6$ alkyl, —$OR_6$, —$COOR_6$, —$CONHR_6$, —$OCOR_6$, =NOH, $NR_6R_7$, —$NR_6COR_7$, 5-6 membered heterocycloalkyl or 5-6 membered heteroaryl; $C_1$-$C_{12}$ alkyl substituted 5-6 membered heterocycloalkyl or $C_1$-$C_{12}$ alkyl substituted 5-6 membered heteroaryl;

or B and C may combine together to form =O, =$NOR_6$, $NHR_6$, 5-6 membered heterocycloalkyl, or 5-6 membered heteroaryl;

wherein the said 5-6 membered heterocycloalkyl, 5-6 membered heteroaryl may optionally contain one or more heteroatom;

wherein, the heteroatom may be O, N, S;

R₁, R₂, and R₄ are independently selected from the group comprising hydrogen, deuterium, hydroxyl, halogen, =O, —$OR_6$, —$NR_6R_7$, —$COR_6$, —$COOR_6$, —$OCOR_6$, —$CONR_6R_7$, $C_1$-$C_6$ alkyl, —Otert-butyldimethylsilyl;

R₃ is hydroxyl, carbonyl, $OCOR_6$;

wherein R₃ is in beta configuration;

R₅ is selected from hydrogen, hydroxyl, halogen, $OR_6$;

R₆ and Rare each independently selected from the group comprising hydrogen, halogen, hydroxyl, $C_1$-$C_{12}$ alkyl, —$NH_2$, —$(CH_2)_nNH_2$, 3-6 membered cycloalkyl, 4-6 membered heterocycloalkyl, 5-6 membered heteroaryl;

X is selected from CH, NH, $NR_6$, O or S;

n is 0 to 3.

The present invention discloses processes for preparation of the compounds of formula I, compositions comprising the compounds of formula and use of the compounds of the present invention in mitochondrial biogenesis and AMPkinase activation.

The present invention also discloses the use of 11β-hydroxypregnenolone and 1β-hydroxyprogestrone in mitochondrial biogenesis and AMP kinase activation.

DEFINITIONS

Figure 1A:
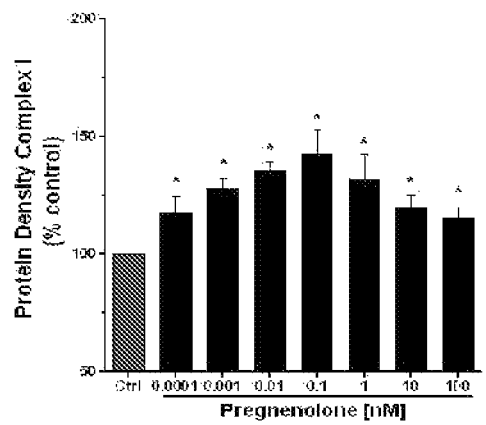
FIG. 1a depictsmitochondrial biogenesis and FIG. 1b depicts stimulation of expression of mitochondrial transcription factors at 3 hours post exposure (I) by 11β-hydroxypregnenolone.

The term "alkyl" refers to a linear or branched saturated monovalent hydrocarbon, wherein the alkylene may optionally be substituted as described herein. The term "alkyl" also encompasses both linear and branched alkyl, unless otherwise specified. In certain embodiments, the alkyl is a linear saturated monovalent hydrocarbon that has the specified number of carbon atoms, or branched saturated monovalent hydrocarbon of specified number of carbon atoms. As used herein, linear C1-C6 and branched C3-C6 alkyl groups are also referred as "lower alkyl." Examples of alkyl groups include, but are not limited to, methyl, ethyl, propyl (including allisomeric forms), n-propyl, isopropyl, butyl (including all isomeric forms), n-butyl, isobutyl, sec-butyl, t-butyl, pentyl (including all isomeric forms), and hexyl (including all isomeric forms). For example, C1-C6 alkyl refers to a linear saturated monovalent hydrocarbon of 1 to 6 carbon atoms or a branched saturated monovalent hydrocarbon of 3 to 6 carbon atoms.

The term "cycloalkyl" as used herein refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Unless otherwise stated, cycloalkyl groups are unsubstituted. A "substituted cycloalkyl" group can be substituted with one or more moieties selected from halo, hydroxy, amino, alkylamino, nitro, cyano, and alkoxy.

The term "heteroaryl" refers to a monocyclic aromatic group and/or multicyclic aromatic group that contain at least one aromatic ring, wherein at least one aromatic ring contains one or more heteroatoms independently selected from 0, S, and N. Each ring of a heteroaryl group may contain one or two 0 atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, andtriazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroarylgroupsinclude, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term heteroaralkyl refers to an aralkyl group as defined above, in which one or more (preferably 1, 2, 3 or 4) carbon atoms have been replaced by an oxygen, nitrogen, silicon, selenium, phosphorus, boron or sulphur atom (preferably oxygen, sulphur or nitrogen), that is to say groups that in accordance with the above definitions contain both aryl or heteroaryl and alkyl, alkenyl, alkynyl and/or heteroalkyl and/or cycloalkyl and/or heterocycloalkyl groups. A heteroaralkyl group preferably contains one or two aromatic ring systems (1 or 2 rings) with from 5 or 6 to 10 carbon atoms and one or two alkyl, alkenyl and/or alkynyl groups having from 1 or 2 to 6 carbon atoms and/or a cycloalkyl group having 5 or 6 ring carbon atoms, with 1, 2, 3 or 4 of those carbon atoms having been replaced by oxygen, sulphur or nitrogen atoms. Examples are aryl-heteroalkyl, aryl-heterocycloalkyl, aryl-heterocycloalkenyl, arylalkyl-heterocycloalkyl, arylalkenyl-heterocycloalkyl, arylalkynyl-heterocycloalkyl, arylalkyl-heterocycloalkenyl, heteroarylalkyl, heteroarylalkenyl, heteroarylalkynyl, heteroaryl-heteroalkyl, heteroarylcyclo-alkyl, heteroarylcycloalkenyl, heteroaryl-heterocycloalkyl, heteroaryl-heterocycloalkenyl, heteroarylalkylcycloalkyl, _ g _ heteroarylalkyl-heterocycloalkenyl, heteroaryl-heteroalkyl-cycloalkyl, heteroaryl-heteroalkylcycloalkenyl and hetero-aryl-heteroalkyl-heterocycloalkyl groups, the cyclic groups being saturated or mono-, di- or tri-unsaturated. Specific examples are the tetrahydroisoquinolinyl, benzoyl, 2- or 3-ethylindolyl, 4-methylpyridino, 2-, 3- or 4-methoxyphenyl, 4-ethoxyphenyl and 2-, 3- or 4-carboxylphenylalkyl groups.

The term "heterocycloalkyl" refers means a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 2 to 6 carbon atoms and from 1 to 3 heteroatoms, referred to herein as (C.sub.1-C.sub.6)heterocycloalkyl.

The term "non-aromatic", as used herein, refers to a cyclic moiety, that may be unsaturated, but that does not have an aromatic character.

The term "substituted" refers to where hydrogen radical on a molecule has been replaced by another atom radical, a functional group radical or a moiety radical; these radicals being generally referred to as "substituents."

The use of terms "a" and "an" and "the" and similar references in the context of describing the invention (especially in the context of the following claims) are to be construed to cover both the singular and the plural, unless otherwise indicated herein or clearly contraindicated by context.

The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise a basic moiety such as an amino group). Also included herein are quaternary ammonium salts such as alkyl ammonium salts. Pharmaceutically acceptable (i.e., non-toxic, physiologically acceptable) salts are preferred.

The term "pharmaceutically acceptable salts" refers to the acid addition salt compound formed with a suitable acid selected from an inorganic acid such as hydrochloric acid, hydrobromic acid; or an organic acid such as benzene sulfonic acid, maleic acid, oxalic acid, fumaric acid, succinic acid, p-toluenesulfonic acid and malic acid.

The term "hydrate" as used herein designates a crystalline molecular compound in which water molecules are incorporated into the crystal lattice. Generally speaking, a hydrate thus designates a crystalline form of a molecular compound, whereby the only further molecules incorporated into the crystal lattice are water molecules.

The term "stereoisomer's" refers to at least two compounds having the same molecular formula and connectivity of atoms, but having a different arrangement of atoms in a three-dimensional space. In view of the present disclosure, a stereoisomer can be, for example, an enantiomer, a diastereomer, or a meso compound.

The term "prophylactic" as used herein refers variously to medicaments, amounts or quantities, methods, uses and effects, etc., that prevent and/or aid in preventing infections.

The term "therapeutic" as used herein refers to preventing, ameliorating, treating, improving, or curing a disease or condition.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "muscular diseases" refers to diseases associated with impaired skeletal muscle or cardiac muscle cell number or function.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein. In certain embodiments, a combination of compounds is administered such that the clearance half-life of each compound from the body overlaps at least partially with one another. For example, a first pharmaceutical has a clearance half-life of 1 hour and is administered at time=0, and a second pharmaceutical has a clearance half-life of 1 hour and is administered at time=45 minutes.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

Compounds and compositions disclosed herein are administered in an "effective amount." This term is defined hereinafter. Unless dictated otherwise, explicitly or otherwise, an "effective amount" is not limited to a minimal amount sufficient to ameliorate a condition, or to an amount that results in an optimal or a maximal amelioration of the condition. In the case when two or more compounds are administered together, an effective amount of one such compound may not be, in and of itself, be an effective amount, but may be an effective amount when used together with additional compounds.

While the phrase "administered together" as used herein may refer to the provision of chemical compositions in the same pharmaceutical composition, the phrase as used herein is not intended to imply that this must be so. Rather, two or more chemical compositions are "administered together" if the $T_{1/2}$ for the clearances of each composition from the body overlaps at least partially with one another. For example, if a first pharmaceutical has a $T_{1/2}$ for clearance of 1 hour and is administered at time=0, and a second pharmaceutical has a $T_{1/2}$ for clearance of 1 hour and is administered at time=45 minutes, such pharmaceuticals are considered administered together. Conversely, if the second drug is administered at time=2 hours, such pharmaceuticals are not considered administered together.

DETAILED DESCRIPTION OF THE INVENTION

A. Compounds of the Present Invention

The present invention provides hydroxysteroids and their intermediates of formula (I):

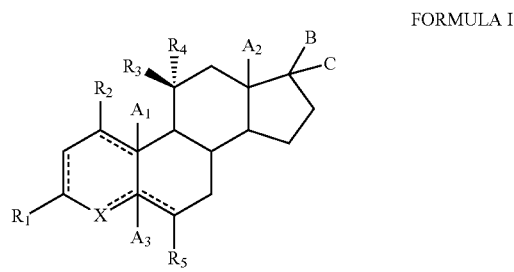

FORMULA I or a salt thereof, wherein:

⚟ is independently either a single bond, a double bond or a cyclopropyl ring, provided that adjacent double bonds are not allowed;

$A_1$, $A_2$, $A_3$ are independently selected from the group comprising hydrogen, hydroxyl, hydroxymethyl, halogen, $C_1$-$C_6$ alkyl;

B and C are each independently selected from the group comprising hydrogen, hydroxyl, halogen, —$OR_6$, —$COR_6$, —$COOR_6$, $OCOR_6$, $CH_2OH$, $CH_2OR_6$, —$CONHR_6$, $CONHR_6R_7$, —$C(OH)R_6R_7$, $NHR_6$, $NHR_5CONHR_6$, —$R_6NHCOOR_7$, —$NR_6R_7$, C(O)heteroaryl, C(O)heterocyclyl, $C_1$-$C_{12}$ straight or branched chain alkyl, 5-6 membered heterocycloalkyl, 5-6 membered heteroaryl;

wherein the $C_1$-$C_{12}$ straight or branched chain alkyl or 5-6 membered heterocycloalkyl or 5-6 membered heteroaryl; may be further optionally substituted with one or more substituents selected from the group comprising halogen, $C_1$-$C_6$ alkyl, —$OR_6$, —$COOR_6$, —$CONHR_6$, —$OCOR_6$, =NOH, $NR_6R_7$, —$NR_6COR_7$, 5-6 membered heterocycloalkyl or 5-6 membered heteroaryl; $C_1$-$C_{12}$ alkyl substituted 5-6 membered heterocycloalkyl or $C_1$-$C_{12}$ alkyl substituted 5-6 membered heteroaryl;

or B and C may combine together to form =O, =$NOR_6$, $NHR_6$, 5-6 membered heterocycloalkyl, or 5-6 membered heteroaryl;

wherein the said 5-6 membered heterocycloalkyl, 5-6 membered heteroaryl may optionally contain one or more heteroatom;

wherein, the heteroatom may be O, N, S;

$R_1$, $R_2$, and $R_4$ are independently selected from the group comprising hydrogen, deuterium, hydroxyl, halogen, =O, —$OR_6$, —$NR_6R_7$, —$COR_6$, —$COOR_6$, —$OCOR_6$, —$CONR_6R_7$, $C_1$-$C_6$ alkyl, —Otert-butyldimethylsilyl;

$R_3$ is hydroxyl, carbonyl, OCOR6;

wherein $R_3$ is in beta configuration;

$R_5$ is selected from hydrogen, hydroxyl, halogen, $OR_6$;

$R_6$ and Rare each independently selected from the group comprising hydrogen, halogen, hydroxyl, $C_1$-$C_{12}$ alkyl, —$NH_2$, —$(CH_2)_nNH_2$, 3-6 membered cycloalkyl, 4-6 membered heterocycloalkyl, 5-6 membered heteroaryl;

X is selected from CH, NH, $NR_6$, O or S;

n is 0 to 3.

The present invention provides hydroxysteroids and their intermediates of formula (II):

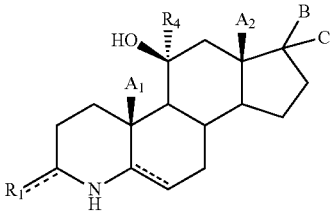

FORMULA II or a salt thereof, wherein:

⌇ is independently either a single bond, a double bond or a cyclopropyl ring, provided that adjacent double bonds are not allowed;

$A_1$, $A_2$, are independently selected from the group comprising hydrogen, hydroxyl, hydroxymethyl, halogen, $C_1$-$C_6$ alkyl;

B and C are each independently selected from the group comprising hydrogen, hydroxyl, halogen, —$OR_6$, —$COR_6$, —$COOR_6$, $OCOR_6$, $CH_2OH$, $CH_2OR_6$, —$CONHR_6$, $CONHR_6R_7$, —$C(OH)R_6R_7$, $NHR_6$, $NHR_5CONHR_6$, —$R_6NHCOOR_7$, —$NR_6R_7$, C(O)heteroaryl, C(O)heterocyclyl, $C_1$-$C_{12}$ straight or branched chain alkyl, 5-6 membered heterocycloalkyl, 5-6 membered heteroaryl;

wherein the $C_1$-$C_{12}$ straight or branched chain alkyl or 5-6 membered heterocycloalkyl or 5-6 membered heteroaryl; may be further optionally substituted with one or more substituents selected from the group comprising halogen, $C_1$-$C_6$ alkyl, —$OR_6$, —$COOR_6$, —$CONHR_6$, —$OCOR_6$, =NOH, $NR_6R_7$, —$NR_6COR_7$, 5-6 membered heterocycloalkyl or 5-6 membered heteroaryl; $C_1$-$C_{12}$ alkyl substituted 5-6 membered heterocycloalkyl or $C_1$-$C_{12}$ alkyl substituted 5-6 membered heteroaryl;

or B and C may combine together to form =O, =$NOR_6$, $NHR_6$, 5-6 membered heterocycloalkyl, or 5-6 membered heteroaryl;

wherein the said 5-6 membered heterocycloalkyl, 5-6 membered heteroaryl may optionally contain one or more heteroatom;

wherein, the heteroatom may be O, N, S;

$R_1$ and $R_4$ are independently selected from the group comprising hydrogen, deuterium, hydroxyl, halogen, =O, —$OR_6$, —$NR_6R_7$, —$COR_6$, —$COOR_6$, —$OCOR_6$, —$CONR_6R_7$, $C_1$-$C_6$ alkyl, —Otert-butyldimethylsilyl;

$R_6$ and Rare each independently selected from the group comprising hydrogen, halogen, hydroxyl, $C_1$-$C_{12}$ alkyl, —$NH_2$, —$(CH_2)nNH_2$, 3-6 membered cycloalkyl, 4-6 membered heterocycloalkyl, 5-6 membered heteroaryl;

n is 0 to 3.

The present invention provides hydroxysteroids and their intermediates of formula (III):

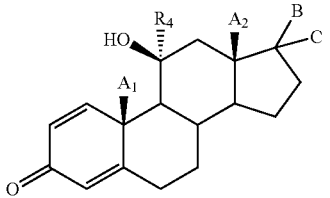

FORMULA III or a salt thereof, wherein:

$A_1$ and $A_2$ are independently selected from the group comprising hydrogen, hydroxyl, hydroxymethyl, halogen, $C_1$-$C_6$ alkyl;

B and C are each independently selected from the group comprising hydrogen, hydroxyl, halogen, —$OR_6$, —$COR_6$, —$COOR_6$, $OCOR_6$, $CH_2OH$, $CH_2OR_6$, —$CONHR_6$, $CONHR_6R_7$, —$C(OH)R_6R_7$, $NHR_6$, $NHR_5CONHR_6$, —$R_6NHCOOR_7$, —$NR_6R_7$, C(O)heteroaryl, C(O)heterocyclyl, $C_1$-$C_{12}$ straight or branched chain alkyl, 5-6 membered heterocycloalkyl, 5-6 membered heteroaryl;

wherein the $C_1$-$C_{12}$ straight or branched chain alkyl or 5-6 membered heterocycloalkyl or 5-6 membered heteroaryl; may be further optionally substituted with one or more substituents selected from the group comprising halogen, $C_1$-$C_6$ alkyl, —$OR_6$, —$COOR_6$, —$CONHR_6$, —$OCOR_6$, =NOH, $NR_6R_7$, —$NR_6COR_7$, 5-6 membered heterocycloalkyl or 5-6 membered heteroaryl; $C_1$-$C_{12}$ alkyl substituted 5-6 membered heterocycloalkyl or $C_1$-$C_{12}$ alkyl substituted 5-6 membered heteroaryl;

or B and C may combine together to form =O, =$NOR_6$, $NHR_6$, 5-6 membered heterocycloalkyl, or 5-6 membered heteroaryl;

wherein the said 5-6 membered heterocycloalkyl, 5-6 membered heteroaryl may optionally contain one or more heteroatom;

wherein, the heteroatom may be O, N, S;

$R_4$ is independently selected from the group comprising hydrogen, deuterium, hydroxyl, halogen, =O, —$OR_6$, —$NR_6R_7$, —$COR_6$, —$COOR_6$, —$OCOR_6$, —$CONR_6R_7$, $C_1$-$C_6$ alkyl, —Otert-butyldimethylsilyl;

$R_6$ and $R_7$ are each independently selected from the group comprising hydrogen, halogen, hydroxyl, $C_1$-$C_{12}$ alkyl, —$NH_2$, —$(CH_2)nNH_2$, 3-6 membered cycloalkyl, 4-6 membered heterocycloalkyl, 5-6 membered heteroaryl;

n is 0 to 3.

The present invention provides hydroxysteroids and their intermediates of formula (IV):

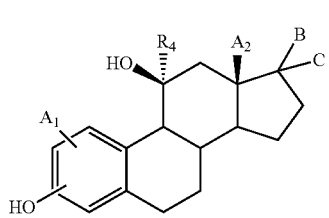

FORMULA IV or a salt thereof, wherein:

A1 and $A_2$ are independently selected from the group comprising hydrogen, hydroxyl, hydroxymethyl, halogen, $C_1$-$C_6$ alkyl;

B and C are each independently selected from the group comprising hydrogen, hydroxyl, halogen, —$OR_6$, —$COR_6$, —$COOR_6$, $OCOR_6$, $CH_2OH$, $CH_2OR_6$, —$CONHR_6$, $CONHR_6R_7$, —$C(OH)R_6R_7$, $NHR_6$, $NHR_5CONHR_6$, —$R_6NHCOOR_7$, —$NR_6R_7$, C(O)heteroaryl, C(O)heterocyclyl, $C_1$-$C_{12}$ straight or branched chain alkyl, 5-6 membered heterocycloalkyl, 5-6 membered heteroaryl;

wherein the $C_1$-$C_{12}$ straight or branched chain alkyl or 5-6 membered heterocycloalkyl or 5-6 membered heteroaryl; may be further optionally substituted with one or more substituents selected from the group comprising halogen, $C_1$-$C_6$ alkyl, —$OR_6$, —$COOR_6$, —$CONHR_6$, —$OCOR_6$, =NOH, $NR_6R_7$, —$NR_6COR_7$, 5-6 membered heterocycloalkyl or 5-6 membered heteroaryl; $C_1$-$C_{12}$ alkyl substituted 5-6 membered heterocycloalkyl or $C_1$-$C_{12}$ alkyl substituted 5-6 membered heteroaryl;

or B and C may combine together to form =O, =NOR$_6$, NHR$_6$, 5-6 membered heterocycloalkyl, or 5-6 membered heteroaryl;

wherein the said 5-6 membered heterocycloalkyl, 5-6 membered heteroaryl may optionally contain one or more heteroatom;

wherein, the heteroatom may be O, N, S;

$R_4$ is independently selected from the group comprising hydrogen, deuterium, hydroxyl, halogen, =O, —OR$_6$, —NR$_6$R$_7$, —COR$_6$, —COOR$_6$, —OCOR$_6$, —CONR$_6$R$_7$, $C_1$-$C_6$ alkyl, —Otert-butyldimethylsilyl;

$R_6$ and $R_7$ are each independently selected from the group comprising hydrogen, halogen, hydroxyl, $C_1$-$C_{12}$ alkyl, —NH$_2$, —(CH$_2$)nNH$_2$, 3-6 membered cycloalkyl, 4-6 membered heterocycloalkyl, 5-6 membered heteroaryl;

n is 0 to 3.

The compounds of the present invention may be illustrated but not limited to the examples as provided in Table 1.

TABLE 1

Illustrative compounds of present invention

| No. | IUPAC name | Structure |
|---|---|---|
| 1001 | (10R,11S,13S,17S)-2,3,6,7,8,9,10,11,12,13,14,15,16,17-tetradecahydro-11-hydroxy-10,13-dimethyl-3-oxo-1H-cyclopenta[a]phenanthrene-17-carboxylic acid | 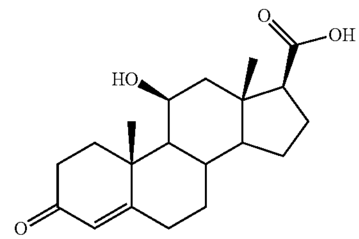 [SMILES: C[C@]12CCC(=O)C=C1CCC1C2[C@@H](O)C[C@@]2(C)C1CC[C@@H]2C(=O)O] |
| 1002 | (3S,8S,9S,10S,11S,13S,14S,17S)-hexadecahydro-3,11-dihydroxy-N,10,13-trimethyl-1H-cyclopenta[a]phenanthrene-17-carboxamide | 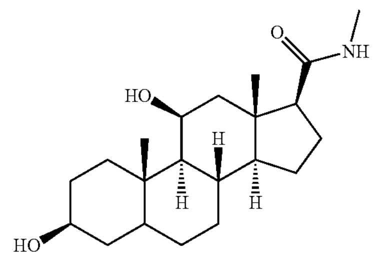 |
| 1003 | (3S,8S,9S,10S,11S,13S,14S,17S)-N-(2-aminoethyl)-hexadecahydro-3,11-dihydroxy-10,13-dimethyl-1H-cyclopenta[a]phenanthrene-17-carboxamide | 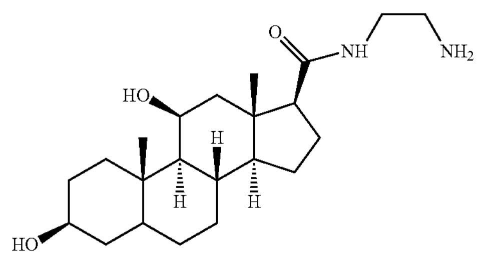 |
| 1004 | (3S,5R,6R,10R,11S,13S,17S)-hexadecahydro-6-methoxy-10,13-dimethyl-17-(2-methyl-1,3-dioxolan-2-yl)-1H-cyclopenta[a]phenanthrene-3,5,11-triol | 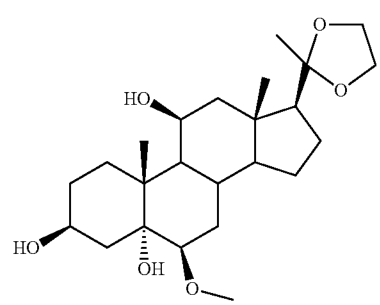 [SMILES: CO[C@@H]1CC2C3CC[C@H](C4(C)OCCO4)[C@@]3(C)C[C@H](O)C2[C@@]2(C)CC[C@H](O)C[C@]12O] |
| 1005 | (4aR,5S,6aS)-5-hydroxy-4a,6a-dimethyl-4,4a,4b,5,6,6a,9,9a,9b,10-decahydro-1H-indeno[5,4-f]quinoline-2,7(3H,8H)-dione | 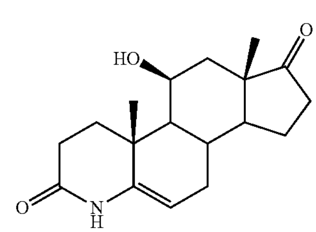 [SMILES: C[C@]12CCC(=O)NC1=CCC1C2[C@@H](O)C[C@]2(C)C(=O)CCC12] |

TABLE 1-continued

Illustrative compounds of present invention

| No. | IUPAC name | Structure |
|---|---|---|
| 1006 | (4a'R,5'S,6a'S)-5'-hydroxy-4a',5',6a'-trimethyl-3',4',4a',4b',5',6',6a',8',9',9a',9b',10'-dodecahydrospiro[[1,3]dioxolane-2,7'-indeno[5,4-f]quinolin]-2'(1'H)-one | 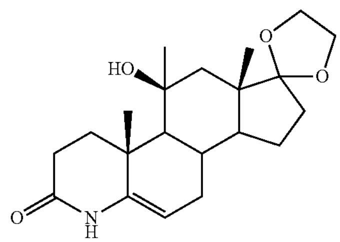 [SMILES: C[C@]1(O)C[C@@]2(C)C(CCC23OCCO3)C2CC=C3NC(=O)CC[C@]3(C)C21] |
| 1007 | (4aR,5S,6aS)-4,4a,4b,5,6,6a,9,9a,9b,10-decahydro-5-hydroxy-4a,6a-dimethyl-1H-indeno[5,4-f]quinoline-2,7(3H,8H)-dione | 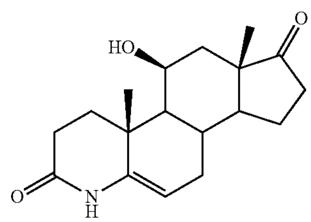 [SMILES: C[C@]12CCC(=O)NC1=CCC1C2[C@@H](O)C[C@]2(C)C(=O)CCC12] |
| 1008 | (4aR,5S,6aS)-7-acetyl-4,4a,4b,5,6,6a,7,8,9,9a,9b,10-dodecahydro-5-hydroxy-4a,5,6a-trimethyl-1H-indeno[5,4-f]quinolin-2(3H)-one | 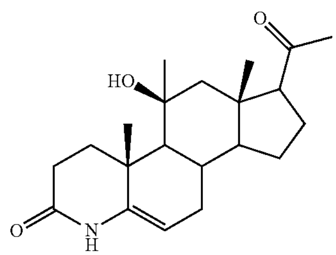 [SMILES: CC(=O)C1CCC2C3CC=C4NC(=O)CC[C@]4(C)C3[C@@](C)(O)C[C@]12C] |
| 1009 | (11S)-7,8,9,11,12,13,14,15,16,17-decahydro-3,11-dihydroxy-6H-cyclopenta[a]phenanthrene-17-carboxylic acid | 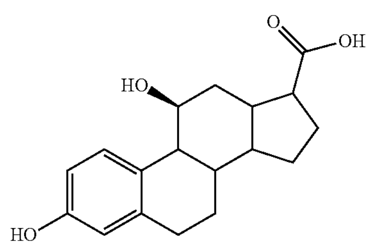 [SMILES: O=C(O)C1CCC2C1C[C@H](O)C1c3ccc(O)cc3CCC21] |
| 1010 | (4aR,6aS)-2,3,4,4a,4b,5,6,6a,7,8,9,9a,9b,10-tetradecahydro-4a,6a-dimethyl-2,5-dioxo-1H-indeno[5,4-f]quinoline-7-carboxylic acid | 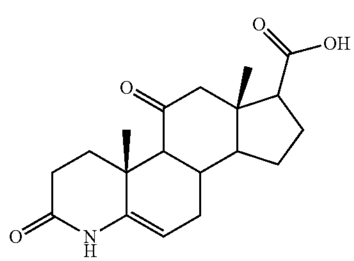 [SMILES: C[C@]12CC(=O)C3C(CC=C4NC(=O)CC[C@@]43C)C1CCC2C(=O)O] |
| 1011 | (17S)-17-acetyl-7,8,13,15,16,17-hexahydro-3-hydroxy-1-methyl-6H-cyclopenta[a]phenanthren-11(9H,12H,14H)-one | 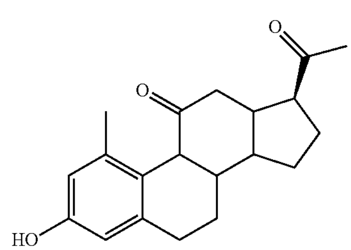 [SMILES: CC(=O)[C@H]1CCC2C3CCc4cc(O)cc(C)c4C3C(=O)CC21] |

TABLE 1-continued

Illustrative compounds of present invention

| No. | IUPAC name | Structure |
|---|---|---|
| 1012 | (13S,17S)-17-acetyl-7,8,13,15,16,17-hexahydro-3-hydroxy-13-methyl-6H-cyclopenta[a]phenanthren-11(9H,12H,14H)-one | 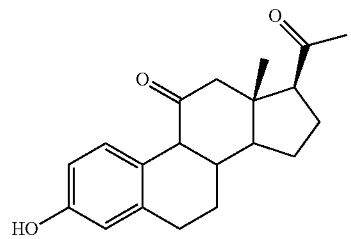 [SMILES: CC(=O)[C@H]1CCC2C3CCc4cc(O)ccc4C3C(=O)C[C@@]21C] |
| 1013 | (10R,11S,13S,17S)-11-hydroxy-10,13-dimethyl-3-oxo-6,7,8,9,10,11,12,13,14,15,16,17-dodecahydro-3H-cyclopenta[a]phenanthrene-17-carboxylic acid | 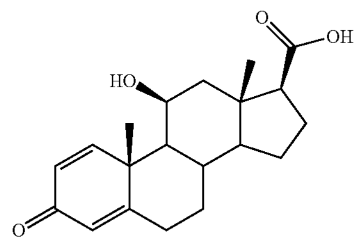 [SMILES: C[C@]12C=CC(=O)C=C1CCC1C2[C@@H](O)C[C@@]2(C)C1CC[C@@H]2C(=O)O] |
| 1014 | (10R,11S,13S,17S)-11-hydroxy-N,N,10,13-tetramethyl-3-oxo-6,7,8,9,10,11,12,13,14,15,16,17-dodecahydro-3H-cyclopenta[a]phenanthrene-17-carboxamide | 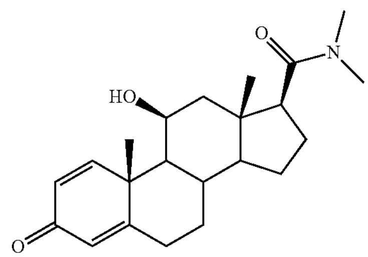 [SMILES: CN(C)C(=O)[C@H]1CCC2C3CCC4=CC(=O)C=C[C@]4(C)C3[C@@H](O)C[C@@]21C] |
| 1015 | (10R,11S,13S,17S)-17-acetyl-11-hydroxy-10,13-dimethyl-6,7,8,9,10,11,12,13,14,15,16,17-dodecahydro-3H-cyclopenta[a]phenanthren-3-one | 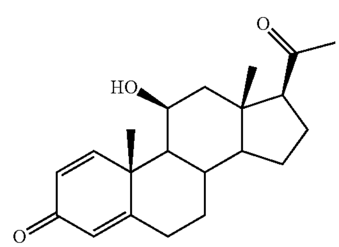 [SMILES: CC(=O)[C@H]1CCC2C3CCC4=CC(=O)C=C[C@]4(C)C3[C@@H](O)C[C@@]21C] |
| 1016 | (10R,11S,13S,17S)-11-hydroxy-17-((R)-1-hydroxyethyl)-10,13-dimethyl-6,7,8,9,10,11,12,13,14,15,16,17-dodecahydro-3H-cyclopenta[a]phenanthren-3-one | 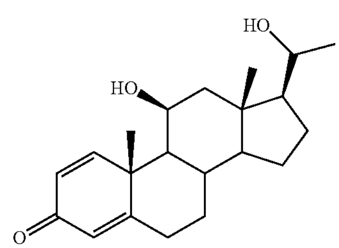 [SMILES: CC(O)[C@H]1CCC2C3CCC4=CC(=O)C=C[C@]4(C)C3[C@@H](O)C[C@@]21C] |
| 1017 | (4a'R,5'S,6a'S)-5'-hydroxy-4a',6a'-dimethyl-3',4',4a',4b',5',6',6a',8',9',9a',9b',10'-dodecahydrospiro[[1,3]dioxolane-2,7'-indeno[5,4-f]quinolin]-2'(1'H)-one | 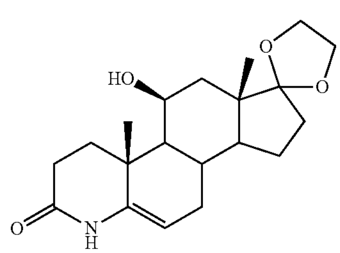 [SMILES: C[C@]12CCC(=O)NC1=CCC1C2[C@@H](O)C[C@@]2(C)C1CCC21OCCO1] |

TABLE 1-continued

Illustrative compounds of present invention

| No. | IUPAC name | Structure |
|---|---|---|
| 1018 | (4aR,5R,6aS)-5-hydroxy-4a,5,6a-trimethyl-4,4a,4b,5,6,6a,9,9a,9b,10-decahydro-1H-indeno[5,4-f]quinoline-2,7(3H,8H)-dione | 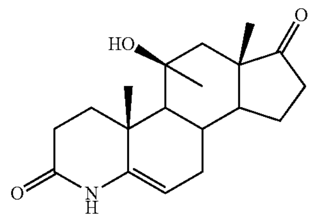 |
| 1019 | (4aR,5S,6aS)-5,7-dihydroxy-4a,6a-dimethyl-4,4a,4b,5,6,6a,7,8,9,9a,9b,10-dodecahydro-1H-indeno[5,4-f]quinolin-2(3H)-one | 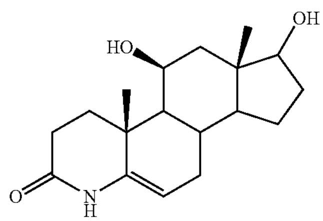 [SMILES: C[C@]12C[C@H](O)C3C(CC=C4NC(=O)CC[C@@]43C)C1CCC2O] |
| 1020 | (4aR,5S,6aS)-7-fluoro-5-hydroxy-4a,6a-dimethyl-4,4a,4b,5,6,6a,7,8,9,9a,9b,10-dodecahydro-1H-indeno[5,4-f]quinolin-2(3H)-one | 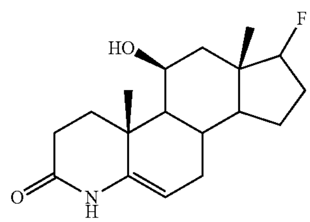 [SMILES: C[C@]12C[C@H](O)C3C(CC=C4NC(=O)CC[C@@]43C)C1CCC2F] |
| 1021 | (4aR,5S,6aS,Z)-5-hydroxy-7-(hydroxyimino)-4a,6a-dimethyl-4,4a,4b,5,6,6a,7,8,9,9a,9b,10-dodecahydro-1H-indeno[5,4-f]quinolin-2(3H)-one | 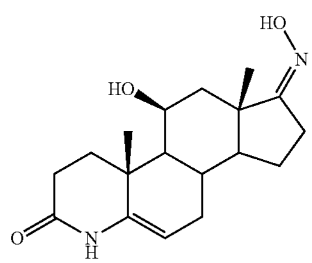 [SMILES: C[C@]12CCC(=O)NC1=CCC1C2[C@@H](O)C[C@]2(C)/C(=N\O)CCC12] |
| 1022 | (4aR,5S,6aS)-5,7-dihydroxy-1,4a,6a-trimethyl-4,4a,4b,5,6,6a,7,8,9,9a,9b,10-dodecahydro-1H-indeno[5,4-f]quinolin-2(3H)-one | 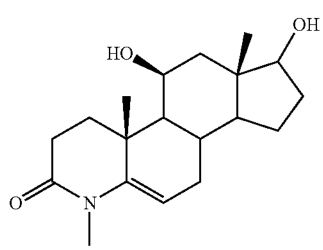 [SMILES: CN1C(=O)CC[C@@]2(C)C1=CCC1C3CCC(O)[C@@]3(C)C[C@H](O)C12] |
| 1023 | (4aR,5S,6aS)-5,7-dihydroxy-4a,6a-dimethyltetradecahydro-1H-indeno[5,4-f]quinolin-2(3H)-one | 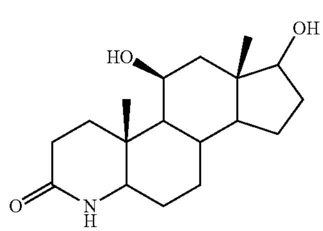 [SMILES: C[C@]12CCC(=O)NC1CCC1C3CCC(O)[C@@]3(C)C[C@H](O)C12] |

TABLE 1-continued

Illustrative compounds of present invention

| No. | IUPAC name | Structure |
| --- | --- | --- |
| 1024 | (4aR,5S,6aS)-7-amino-5-hydroxy-4a,6a-dimethyltetradecahydro-1H-indeno[5,4-f]quinolin-2(3H)-one | 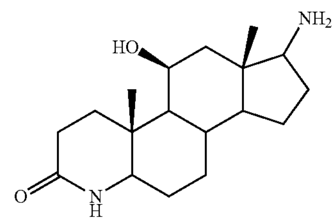 [SMILES: C[C@]12CCC(=O)NC1CCC1C3CCC(N)[C@@]3(C)C[C@H](O)C12] |
| 1025 | (4aR,5S,6aS,7S)-5-hydroxy-4a,6a-dimethyl-7-(2-methyl-1,3-dioxolan-2-yl)-4,4a,4b,5,6,6a,7,8,9,9a,9b,10-dodecahydro-1H-indeno[5,4-f]quinolin-2(3H)-one | 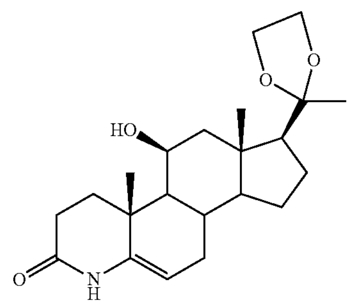 [SMILES: CC1([C@H]2CCC3C4CC=C5NC(=O)CC[C@]5(C)C4[C@@H](O)C[C@@]32C)OCCO1] |
| 1026 | (4aR,5S,6aS,7S)-5-hydroxy-4a,5,6a-trimethyl-7-(2-methyl-1,3-dioxolan-2-yl)-4,4a,4b,5,6,6a,7,8,9,9a,9b,10-dodecahydro-1H-indeno[5,4-f]quinolin-2(3H)-one | 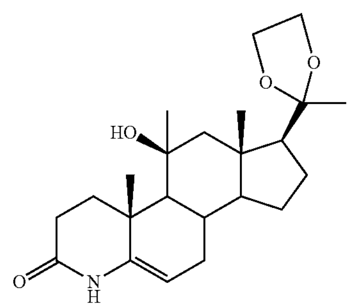 [SMILES: CC1([C@H]2CCC3C4CC=C5NC(=O)CC[C@]5(C)C4[C@@](C)(O)C[C@@]32C)OCCO1] |
| 1027 | (4aR,5S,6aS,7S)-5-hydroxy-4a,6a-dimethyl-2-oxo-2,3,4,4a,4b,5,6,6a,7,8,9,9a,9b,10-tetradecahydro-1H-indeno[5,4-f]quinoline-7-carboxylic acid | 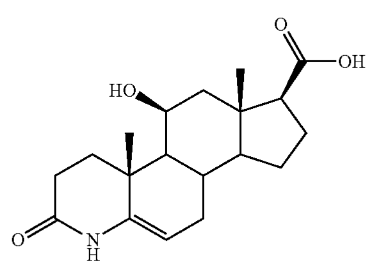 [SMILES: C[C@]12CCC(=O)NC1=CCC1C2[C@@H](O)C[C@@]2(C)C1CC[C@@H]2C(=O)O] |
| 1028 | (11S,13S)-17-(1-hydroxyethyl)-13-methyl-7,8,9,11,12,13,14,15,16,17-decahydro-6H-cyclopenta[a]phenanthrene-3,11-diol | 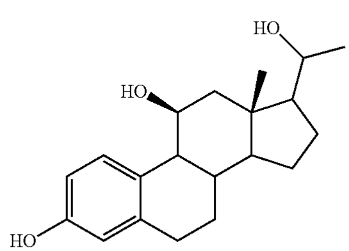 [SMILES: CC(O)C1CCC2C3CCc4cc(O)ccc4C3[C@@H](O)C[C@]12C] |

TABLE 1-continued

Illustrative compounds of present invention

| No. | IUPAC name | Structure |
|---|---|---|
| 1029 | 1-((11S,13S)-3,11-dihydroxy-13-methyl-7,8,9,11,12,13,14,15,16,17-decahydro-6H-cyclopenta[a]phenanthren-17-yl)ethanone | 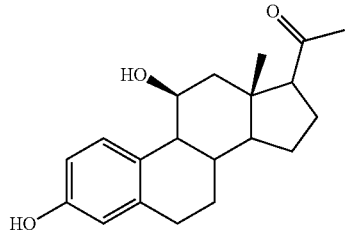 [SMILES: CC(=O)C1CCC2C3CCc4cc(O)ccc4C3[C@@H](O)C[C@]12C] |
| 1030 | (11S,13S)-17-(1-hydroxyethyl)-3-methoxy-13-methyl-7,8,9,11,12,13,14,15,16,17-decahydro-6H-cyclopenta[a]phenanthren-11-ol | 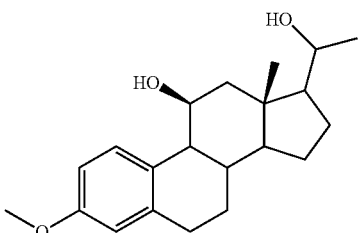 |
| 1031 | (11S,13S)-3-((tert-butyldimethylsilyl)oxy)-13-methyl-17-(2-methyl-1,3-dioxolan-2-yl)-7,8,9,11,12,13,14,15,16,17-decahydro-6H-cyclopenta[a]phenanthren-11-ol | 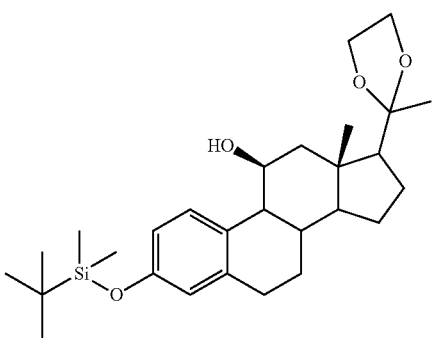 [SMILES: CC1(C2CCC3C4CCc5cc(O[Si](C)(C)C(C)(C)C)ccc5C4[C@@H](O)C[C@@]32C)OCCO1] |
| 1032 | (11S,3S)-13-methyl-17-(2-methyl-1,3-dioxolan-2-yl)-7,8,9,11,12,13,14,15,16,17-decahydro-6H-cyclopenta[a]phenanthrene-3,11-diol | 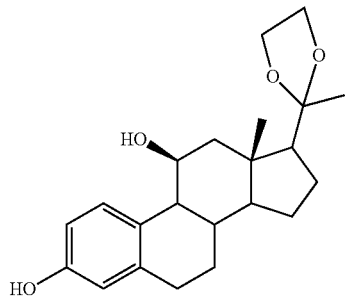 [SMILES: CC1(C2CCC3C4CCc5cc(O)ccc5C4[C@@H](O)C[C@@]32C)OCCO1] |
| 1033 | (10R,11S,13S,17S)-11,17-dihydroxy-10,13-dimethyl-6,7,8,9,10,11,12,13,14,15,16,17-dodecahydro-3H-cyclopenta[a]phenanthren-3-one | 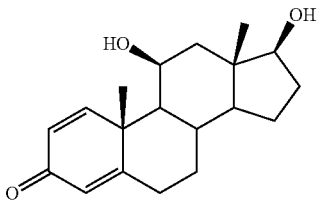 [SMILES: C[C@]12C=CC(=O)C=C1CCC1C2[C@@H](O)C[C@@]2(C)C1CC[C@@H]2O] |
| 1034 | (10R,11S,13S)-11-hydroxy-10,13-dimethyl-7,8,9,10,11,12,13,14,15,16-decahydro-3H-cyclopenta[a]phenanthrene-3,17(6H)-dione | 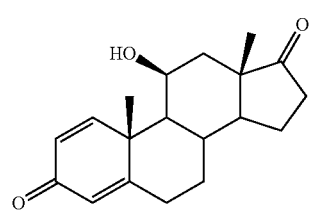 [SMILES: C[C@]12C=CC(=O)C=C1CCC1C2[C@@H](O)C[C@]2(C)C(=O)CCC12] |

TABLE 1-continued

Illustrative compounds of present invention

| No. | IUPAC name |
|---|---|
| 1035 | (11S,13S,17S)-4,11-dihydroxy-1,13-dimethyl-7,8,9,11,12,13,14,15,16,17-decahydro-6H-cyclopenta[a]phenanthrene-17-carboxylic acid |
| 1036 | (11S,13S,17S)-13-methyl-7,8,9,11,12,13,14,15,16,17-decahydro-6H-cyclopenta[a]phenanthrene-3,11,17-triol |
| 1037 | (4aR,5S,6aS,7S)-7-acetyl-5-hydroxy-4a,6a-dimethyl-4,4a,4b,5,6,6a,7,8,9,9a,9b,10-dodecahydro-1H-indeno[5,4-f]quinolin-2(3H)-one |
| 1038 | (4aR,5S,6aS,7S)-5-hydroxy-7-(2-hydroxypropan-2-yl)-4a,6a-dimethyl-4,4a,4b,5,6,6a,7,8,9,9a,9b,10-dodecahydro-1H-indeno[5,4-f]quinolin-2(3H)-one |
| 1039 | 1-((8S,9S,10R,11S,13S,14S)-3,11-dihydroxy-10,13-dimethyl-2,3,4,7,8,9,10,11,12,13,14,15,16,17-tetradecahydro-1H-cyclopenta[a]phenanthren-17-yl)ethanone |
| 1040 | (8S,9S,10R,11S,13S,14S)-17-acetyl-11-hydroxy-10,13-dimethyl-6,7,8,9,10,11,12,13,14,15,16,17-dodecahydro-1H-cyclopenta[a]phenanthren-3(2H)-one |

TABLE 1-continued

Illustrative compounds of present invention

| No. | IUPAC name | Structure |
|---|---|---|
| 1041 | (10R,11S,13S,17S)-11-hydroxy-10,13-dimethyl-3-oxo-6,7,8,9,10,11,12,13,14,15,16,17-dodecahydro-3H-cyclopenta[a]phenanthrene-17-carboxamide | 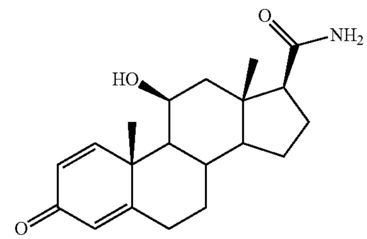 [SMILES: C[C@]12C=CC(=O)C=C1CCC1C2[C@@H](O)C[C@@]2(C)C1CC[C@@H]2C(N)=O] |
| 1042 | (10R,11S,13S,17S)-11-hydroxy-17-(hydroxymethyl)-10,13-dimethyl-6,7,8,9,10,11,12,13,14,15,16,17-dodecahydro-3H-cyclopenta[a]phenanthren-3-one | 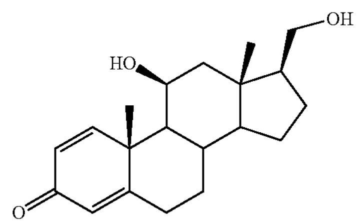 [SMILES: C[C@]12C=CC(=O)C=C1CCC1C2[C@@H](O)C[C@@]2(C)C1CC[C@@H]2CO] |
| 1043 | (10R,11S,13S,17S)-17-((dimethylamino)methyl)-11-hydroxy-10,13-dimethyl-6,7,8,9,10,11,12,13,14,15,16,17-dodecahydro-3H-cyclopenta[a]phenanthren-3-one | 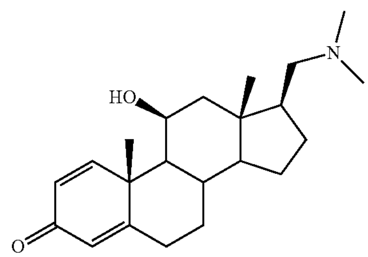 [SMILES: CN(C)C[C@H]1CCC2C3CCC4=CC(=O)C=C[C@]4(C)C3[C@@H](O)C[C@@]21C] |
| 1044 | (11S,13S,17S)-methyl 4,11-dihydroxy-1,13-dimethyl-7,8,9,11,12,13,14,15,16,17-decahydro-6H-cyclopenta[a]phenanthrene-17-carboxylate | 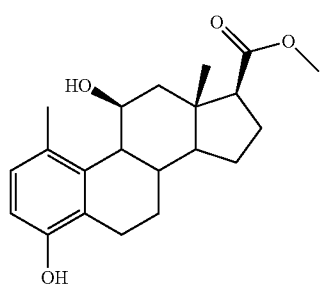 [SMILES: COC(=O)[C@H]1CCC2C3CCc4c(O)ccc(C)c4C3[C@@H](O)C[C@@]21C] |
| 1045 | (11S,13S,17S)-4,11-dihydroxy-1,13-dimethyl-7,8,9,11,12,13,14,15,16,17-decahydro-6H-cyclopenta[a]phenanthrene-17-carboxamide | 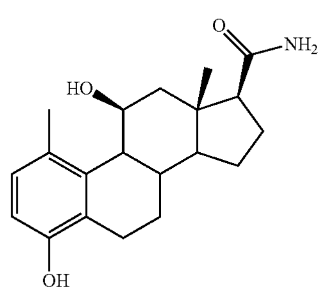 [SMILES: Cc1ccc(O)c2c1C1C(CC2)C2CC[C@H](C(N)=O)[C@@]2(C)C[C@@H]1O] |

TABLE 1-continued

Illustrative compounds of present invention

| No. | IUPAC name | Structure |
| --- | --- | --- |
| 1046 | (11S,13S,17S)-4,11-dihydroxy-N,N,1,13-tetramethyl-7,8,9,11,12,13,14,15,16,17-decahydro-6H-cyclopenta[a]phenanthrene-17-carboxamide | 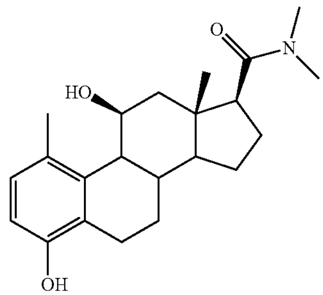 [SMILES: Cc1ccc(O)c2c1C1C(CC2)C2CC[C@H](C(=O)N(C)C)[C@@]2(C)C[C@@H]1O] |
| 1047 | ((11S,13S,17S)-4,11-dihydroxy-1,13-dimethyl-7,8,9,11,12,13,14,15,16,17-decahydro-6H-cyclopenta[a]phenanthren-17-yl)(piperazin-1-yl)methanone | 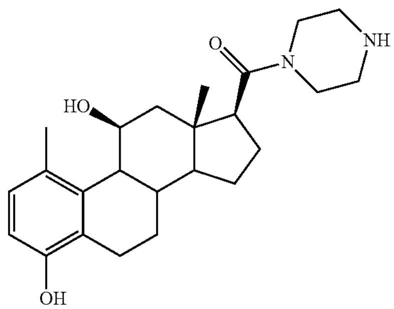 [SMILES: Cc1ccc(O)c2c1C1C(CC2)C2CC[C@H](C(=O)N3CCNCC3)[C@@]2(C)C[C@@H]1O] |
| 1048 | (11S,13S,17S)-17-(hydroxymethyl)-1,13-dimethyl-7,8,9,11,12,13,14,15,16,17-decahydro-6H-cyclopenta[a]phenanthrene-4,11-diol | 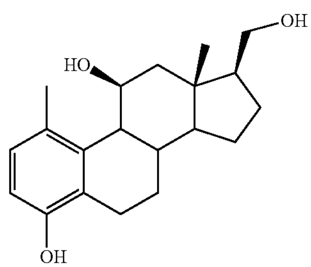 [SMILES: Cc1ccc(O)c2c1C1C(CC2)C2CC[C@H](CO)[C@@]2(C)C[C@@H]1O] |
| 1049 | (11S,13S,17S)-11-hydroxy-4-methoxy-1,13-dimethyl-7,8,9,11,12,13,14,15,16,17-decahydro-6H-cyclopenta[a]phenanthrene-17-carboxylic acid | 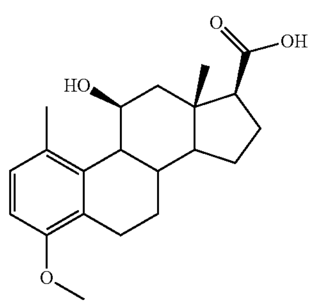 [SMILES: COc1ccc(C)c2c1CCC1C2[C@@H](O)C[C@@]2(C)C1CC[C@@H]2C(=O)O] |
| 1050 | (11S,13S,17S)-17-((dimethylamino)methyl)-1,13-dimethyl-7,8,9,11,12,13,14,15,16,17-decahydro-6H-cyclopenta[a]phenanthrene-4,11-diol | 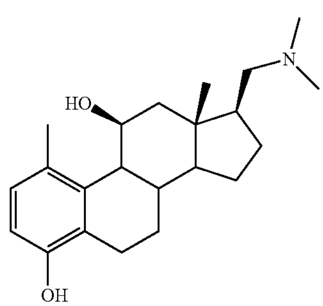 [SMILES: Cc1ccc(O)c2c1C1C(CC2)C2CC[C@H](CN(C)C)[C@@]2(C)C[C@@H]1O] |

TABLE 1-continued

Illustrative compounds of present invention

| No. | IUPAC name | Structure |
|---|---|---|
| 1051 | 1-((11S,13S)-11-hydroxy-3-methoxy-13-methyl-7,8,9,11,12,13,14,15,16,17-decahydro-6H-cyclopenta[a]phenanthren-17-yl)ethanone | 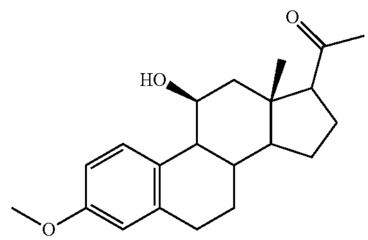 [SMILES: COc1ccc2c(c1)CCC1C2[C@@H](O)C[C@]2(C)C(C(C)=O)CCC12] |
| 1052 | (E)-1-((11S,13S)-3,11-dihydroxy-13-methyl-7,8,9,11,12,13,14,15,16,17-decahydro-6H-cyclopenta[a]phenanthren-17-yl)ethanone oxime | 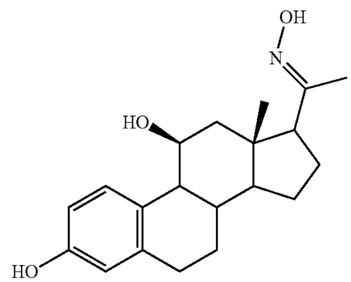 [SMILES: C/C(=N\O)C1CCC2C3CCc4cc(O)ccc4C3[C@@H](O)C[C@]12C] |
| 1053 | (E)-1-((11S,13S)-3,11-dihydroxy-13-methyl-7,8,9,11,12,13,14,15,16,17-decahydro-6H-cyclopenta[a]phenanthren-17-yl)ethanone oxime | 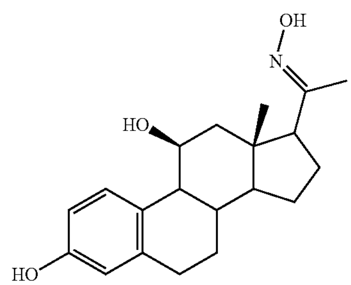 [SMILES: C/C(=N\O)C1CCC2C3CCc4cc(O)ccc4C3[C@@H](O)C[C@]12C] |
| 1054 | (11S,13S)-17-(2-hydroxypropan-2-yl)-13-methyl-7,8,9,11,12,13,14,15,16,17-decahydro-6H-cyclopenta[a]phenanthrene-3,11-diol | 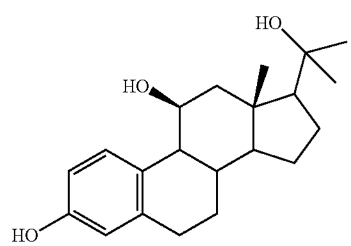 [SMILES: CC(C)(O)C1CCC2C3CCc4cc(O)ccc4C3[C@@H](O)C[C@@]21C] |
| 1055 | (11S,13R)-17-ethyl-13-methyl-7,8,9,11,12,13,14,15,16,17-decahydro-6H-cyclopenta[a]phenanthrene-3,11-diol | 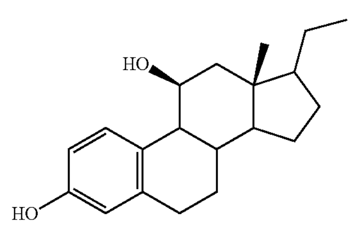 [SMILES: CCC1CCC2C3CCc4cc(O)ccc4C3[C@@H](O)C[C@]12C] |
| 1056 | (8S,9S,10R,11S,13S,14S,Z)-11-hydroxy-17-(hydroxyimino)-10,13-dimethyl-6,7,8,9,10,11,12,13,14,15,16,17-dodecahydro-3H-cyclopenta[a]phenanthren-3-one | 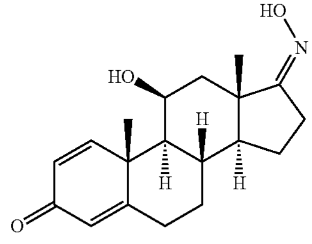 |

TABLE 1-continued

Illustrative compounds of present invention

| No. | IUPAC name | Structure |
|---|---|---|
| 1057 | (8S,9S,10R,11S,13S,14S)-17-amino-11-hydroxy-10,13-dimethyl-6,7,8,9,10,11,12,13,14,15,16,17-dodecahydro-3H-cyclopenta[a]phenanthren-3-one | 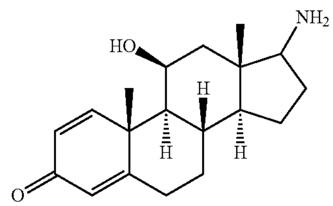 |
| 1058 | (8S,9S,10R,11S,13S,14S)-11-hydroxy-10,13-dimethyl-6,7,8,9,10,11,12,13,14,15,16,17-dodecahydro-3H-cyclopenta[a]phenanthren-3-one | 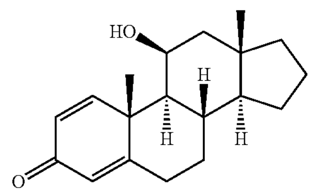 |
| 1059 | (8S,9S,10R,11S,13S,14S,17S)-11,17-dihydroxy-10,13,17-trimethyl-6,7,8,9,10,11,12,13,14,15,16,17-dodecahydro-3H-cyclopenta[a]phenanthren-3-one | 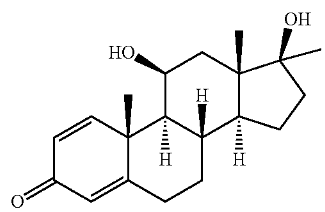 |
| 1060 | (11R,13S,17S)-11,13,17-trimethyl-7,8,9,11,12,13,14,15,16,17-decahydro-6H-cyclopenta[a]phenanthrene-3,11,17-triol | 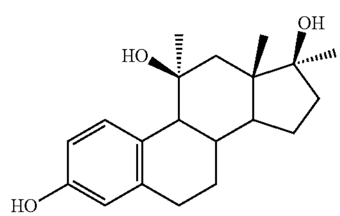 [SMILES: C[C@]1(O)C[C@@]2(C)C(CC[C@]2(C)O)C2CCc3cc(O)ccc3C21] |
| 1061 | (11S,13S)-13-methyl-7,8,9,11,12,13,14,15,16,17-decahydro-6H-cyclopenta[a]phenanthrene-3,11-diol | 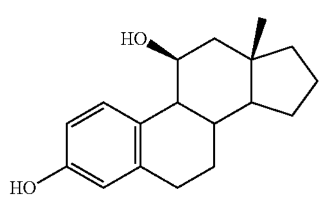 [SMILES: C[C@@]12CCCC1C1CCc3cc(O)ccc3C1[C@@H](O)C2] |
| 1062 | (11S,13S,17S)-17-amino-13-methyl-7,8,9,11,12,13,14,15,16,17-decahydro-6H-cyclopenta[a]phenanthrene-3,11-diol | 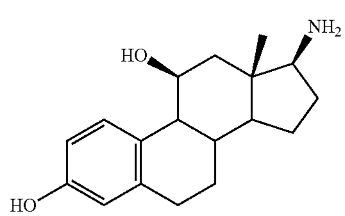 [SMILES: C[C@]12C[C@H](O)C3c4ccc(O)cc4CCC3C1CC[C@@H]2N] |
| 1063 | (11S,13S,Z)-3,11-dihydroxy-13-methyl-7,8,9,11,12,13,15,16-octahydro-6H-cyclopenta[a]phenanthren-17(14H)-one oxime | 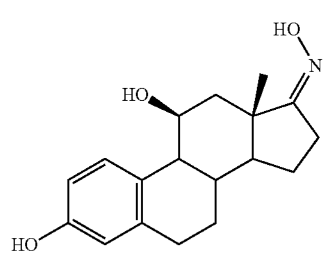 [SMILES: C[C@]12C[C@H](O)C3c4ccc(O)cc4CCC3C1CC/C2=N/O] |

TABLE 1-continued

Illustrative compounds of present invention

| No. | IUPAC name | Structure |
|---|---|---|
| 1064 | (4aR,5S,6aS,7S)-5-hydroxy-4a,6a-dimethyl-7-(2-methyl-1,3-dioxolan-2-yl)-4,4a,4b,5,6,6a,7,8,9,9a,9b,10-dodecahydro-1H-indeno[5,4-f]quinolin-2(3H)-one | 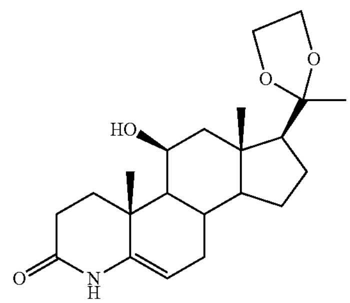 [SMILES: CC1([C@H]2CCC3C4CC=C5NC(=O)CC[C@]5(C)C4[C@@H](O)C[C@@]32C)OCCO1] |
| 1065 | (4aR,5S,6aS,7S)-5-hydroxy-4a,6a-dimethyl-2-oxo-2,3,4,4a,4b,5,6,6a,7,8,9,9a,9b,10-tetradecahydro-1H-indeno[5,4-f]quinoline-7-carboxylic acid | 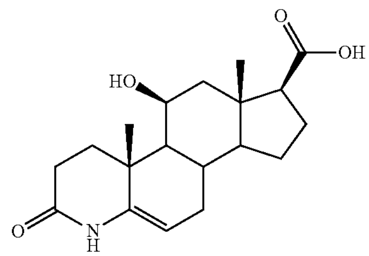 [SMILES: C[C@]12CCC(=O)NC1=CCC1C2[C@@H](O)C[C@@]2(C)C1CC[C@@H]2C(=O)O] |

The compounds of the present invention include:
i. (10R,11S,13S,17S)-2,3,6,7,8,9,10,11,12,13,14,15,16,17-tetradecahydro-11-hydroxy-10,13-dimethyl-3-oxo-1H-cyclopenta[a]phenanthrene-17-carboxylic acid
ii. (3S,8S,9S,10S,11S,13S,14S,17S)-hexadecahydro-3,11-dihydroxy-N,10,13-trimethyl-1H-cyclopenta[a]phenanthrene-17-carboxamide
iii. (3S,8S,9S,10S,11S,13S,14S,17S)—N-(2-aminoethyl)-hexadecahydro-3,11-dihydroxy-10,13-dimethyl-1H-cyclopenta[a]phenanthrene-17-carboxamide
iv. (3S,5R,6R,10R,11S,13S,17S)-hexadecahydro-6-methoxy-10,13-dimethyl-17-(2-methyl-1,3-dioxolan-2-yl)-1H-cyclopenta[a]phenanthrene-3,5,11-triol
v. (4aR,5S,6aS)-5-hydroxy-4a,6a-dimethyl-4,4a,4b,5,6,6a,9,9a,9b,10-decahydro-1H-indeno[5,4-f]quinoline-2,7βH,8H)-dione(4a'R,5'S,6a'S)-5'-hydroxy-4a',5',6a'-trimethyl-3',4',4a',4b',5',6',6a',8',9',9a',9b',10'-dodecahydrospiro[[1,3]dioxolane-2,7'-indeno[5,4-f]quinolin]-2'(1'H)-one
vi. (4aR,5S,6aS)-4,4a,4b,5,6,6a,9,9a,9b,10-decahydro-5-hydroxy-4a,6a-dimethyl-1H-indeno[5,4-f]quinoline-2,7βH,8H)-dione
vii. (4aR,5S,6aS)-7-acetyl-4,4a,4b,5,6,6a,7,8,9,9a,9b,10-decahydro-5-hydroxy-4a,5,6a-trimethyl-1H-indeno[5,4-f]quinolin-2(3H)-one
viii. (11S)-7,8,9,11,12,13,14,15,16,17-decahydro-3,11-dihydroxy-6H-cyclopenta[a]phenanthrene-17-carboxylic acid
ix. (4aR,6aS)-2,3,4,4a,4b,5,6,6a,7,8,9,9a,9b,10-tetradecahydro-4a,6a-dimethyl-2,5-dioxo-1H-indeno[5,4-f]quinoline-7-carboxylic acid
x. (17S)-17-acetyl-7,8,13,15,16,17-hexahydro-3-hydroxy-1-methyl-6H-cyclopenta[a]phenanthren-11(9H,12H,14H)-one
xi. (13S,17S)-17-acetyl-7,8,13,15,16,17-hexahydro-3-hydroxy-13-methyl-6H-cyclopenta[a]phenanthren-11(9H,12H,14H)-one
xii. (10R,11S,13S,17S)-11-hydroxy-10,13-dimethyl-3-oxo-6,7,8,9,10,11,12,13,14,15,16,17-dodecahydro-3H-cyclopenta[a]phenanthrene-17-carboxylic acid
xiii. (10R,11S,13S,17S)-11-hydroxy-N,N,10,13-tetramethyl-3-oxo-6,7,8,9,10,11,12,13,14,15,16,17-dodecahydro-3H-cyclopenta[a]phenanthrene-17-carboxamide
xiv. (10R,11S,13S,17S)-17-acetyl-11-hydroxy-10,13-dimethyl-6,7,8,9,10,11,12,13,14,15,16,17-dodecahydro-3H-cyclopenta[a]phenanthren-3-one
xv. (10R,11S,13S,17S)-11-hydroxy-17-((R)-1-hydroxyethyl)-10,13-dimethyl-6,7,8,9,10,11,12,13,14,15,16,17-dodecahydro-3H-cyclopenta[a]phenanthren-3-one
xvi. (4a'R,5'S,6a'S)-5'-hydroxy-4a',6a'-dimethyl-3',4',4a',4b',5',6',6a',8',9',9a',9b',10'-dodecahydrospiro[[1,3]dioxolane-2,7'-indeno[5,4-f]quinolin]-2'(1'H)-one
xvii. (4aR,5R,6aS)-5-hydroxy-4a,5,6a-trimethyl-4,4a,4b,5,6,6a,9,9a,9b,10-decahydro-1H-indeno[5,4-f]quinoline-2,7βH,8H)-dione
xviii. (4aR,5S,6aS)-5,7-dihydroxy-4a,6a-dimethyl-4,4a,4b,5,6,6a,7,8,9,9a,9b,10-dodecahydro-1H-indeno[5,4-f]quinolin-2(3H)-one
xix. (4aR,5S,6aS)-7-fluoro-5-hydroxy-4a,6a-dimethyl-4,4a,4b,5,6,6a,7,8,9,9a,9b,10-dodecahydro-1H-indeno[5,4-f]quinolin-2(3H)-one
xx. (4aR,5S,6aS,Z)-5-hydroxy-7-(hydroxyimino)-4a,6a-dimethyl-4,4a,4b,5,6,6a,7,8,9,9a,9b,10-dodecahydro-1H-indeno[5,4-f]quinolin-2(3H)-one
xxi. (4aR,5S,6aS)-5,7-dihydroxy-1,4a,6a-trimethyltetradecahydro-1H-indeno[5,4-f]quinolin-2(3H)-one
xxii. (4aR,5S,6aS)-5,7-dihydroxy-1,4a,6a-trimethyl-4,4a,4b,5,6,6a,7,8,9,9a,9b,10-dodecahydro-1H-indeno[5,4-f]quinolin-2(3H)-one
xxiii. (4aR,5S,6aS)-7-amino-5-hydroxy-4a,6a-dimethyltetradecahydro-1H-indeno[5,4-f]quinolin-2(3H)-one
xxiv. (4aR,5S,6aS,7S)-5-hydroxy-4a,6a-dimethyl-7-(2-methyl-1,3-dioxolan-2-yl)-4,4a,4b,5,6,6a,7,8,9,9a,9b,10-dodecahydro-1H-indeno[5,4-f]quinolin-2(3H)-one
xxv. (4aR,5S,6aS,7S)-5-hydroxy-4a,5,6a-trimethyl-7-(2-methyl-1,3-dioxolan-2-yl)-4,4a,4b,5,6,6a,7,8,9,9a,9b,10-dodecahydro-1H-indeno[5,4-f]quinolin-2(3H)-one xxvi. (4aR,5S,6aS,7S)-5-hydroxy-4a,6a-dimethyl-2-oxo-2,3,4,4a,4b,5,6,6a,7,8,9,9a,9b,10-tetradecahydro-1H-indeno[5,4-f]quinoline-7-carboxylic acid xxvii. (11S,13S)-17-(1-hydroxyethyl)-13-methyl-7,8,9,11,12,13,14,15,16,17-decahydro-6H-cyclopenta[a]phenanthrene-3,11-diol xxviii. 1-((11S,13S)-3,11-dihydroxy-13-methyl-7,8,9,11,12,13,14,15,16,17-decahydro-6H-cyclopenta[a]phenanthren-17-yl)ethanone xxix. (11S,13S)-17-(1-hydroxyethyl)-3-methoxy-13-methyl-7,8,9,11,12,13,14,15,16,17-decahydro-6H-cyclopenta[a]phenanthren-11-ol xxx. (11S,13S)-3-((tert-butyldimethylsilyl)oxy)-13-methyl-17-(2-methyl-1,3-dioxolan-2-yl)-7,8,9,11,12,13,14,15,16,17-decahydro-6H-cyclopenta[a]phenanthren-11-ol xxxi. (11S,13S)-13-methyl-17-(2-methyl-1,3-dioxolan-2-yl)-7,8,9,11,12,13,14,15,16,17-decahydro-6H-cyclopenta[a]phenanthrene-3,11-diol xxxii. (10R,11S,13S,17S)-11,17-dihydroxy-10,13-dimethyl-6,7,8,9,10,11,12,13,14,15,16,17-dodecahydro-3H-cyclopenta[a]phenanthren-3-one xxxiii. (10R,11S,13S)-11-hydroxy-10,13-dimethyl-7,8,9,10,11,12,13,14,15,16-decahydro-3H-cyclopenta[a]phenanthrene-3,17(6H)-dione xxxiv. (11S,13S,17S)-4,11-dihydroxy-1,13-dimethyl-7,8,9,11,12,13,14,15,16,17-decahydro-6H-cyclopenta[a]phenanthrene-17-carboxylic acid xxxv. (11S,13S,17S)-13-methyl-7,8,9,11,12,13,14,15,16,17-decahydro-6H-cyclopenta[a]phenanthrene-3,11,17-triol xxxvi. (4aR,5S,6aS,7S)-7-acetyl-5-hydroxy-4a,6a-dimethyl-4,4a,4b,5,6,6a,7,8,9,9a,9b,10-dodecahydro-1H-indeno[5,4-f]quinolin-2(3H)-one xxxvii. (4aR,5S,6aS,7S)-5-hydroxy-7-(2-hydroxypropan-2-yl)-4a,6a-dimethyl-4,4a,4b,5,6,6a,7,8,9,9a,9b,10-dodecahydro-1H-indeno[5,4-f]quinolin-2(3H)-one xxxviii. 1-((8S,9S,10R,11S,13S,14S)-3,11-dihydroxy-10,13-dimethyl-2,3,4,7,8,9,10,11,12,13,14,15,16,17-tetradecahydro-1H-cyclopenta[a]phenanthren-17-yl)ethanone xxxix. (8S,9S,10R,11S,13S,14S)-17-acetyl-11-hydroxy-10,13-dimethyl-6,7,8,9,10,11,12,13,14,15,16,17-dodecahydro-1H-cyclopenta[a]phenanthren-3(2H)-one xl. (10R,11S,13S,17S)-11-hydroxy-10,13-dimethyl-3-oxo-6,7,8,9,10,11,12,13,14,15,16,17-dodecahydro-3H-cyclopenta[a]phenanthrene-17-carboxamide xli. (10R,11S,13S,17S)-11-hydroxy-17-(hydroxymethyl)-10,13-dimethyl-6,7,8,9,10,11,12,13,14,15,16,17-dodecahydro-3H-cyclopenta[a]phenanthren-3-one xlii. (10R,11S,13S,17S)-17-((dimethylamino)methyl)-11-hydroxy-10,13-dimethyl-6,7,8,9,10,11,12,13,14,15,16,17-dodecahydro-3H-cyclopenta[a]phenanthren-3-one xliii. (11S,13S,17S)-methyl 4,11-dihydroxy-1,13-dimethyl-7,8,9,11,12,13,14,15,16,17-decahydro-6H-cyclopenta[a]phenanthrene-17-carboxylate xliv. (11S,13S,17S)-4,11-dihydroxy-1,13-dimethyl-7,8,9,11,12,13,14,15,16,17-decahydro-6H-cyclopenta[a]phenanthrene-17-carboxamide xlv. (11S,13S,17S)-4,11-dihydroxy-N,N,1,13-tetramethyl-7,8,9,11,12,13,14,15,16,17-decahydro-6H-cyclopenta[a]phenanthrene-17-carboxamide xlvi. ((11S,13S,17S)-4,11-dihydroxy-1,13-dimethyl-7,8,9,11,12,13,14,15,16,17-decahydro-6H-cyclopenta[a]phenanthren-17-yl)(piperazin-1-yl)methanone xlvii. (11S,13S,17S)-17-(hydroxymethyl)-1,13-dimethyl-7,8,9,11,12,13,14,15,16,17-decahydro-6H-cyclopenta[a]phenanthrene-4,11-diol xlviii. (11S,13S,17S)-11-hydroxy-4-methoxy-1,13-dimethyl-7,8,9,11,12,13,14,15,16,17-decahydro-6H-cyclopenta[a]phenanthrene-17-carboxylic acid xlix. (11S,13S,17S)-17-((dimethylamino)methyl)-1,13-dimethyl-7,8,9,11,12,13,14,15,16,17-decahydro-6H-cyclopenta[a]phenanthrene-4,11-diol l. 1-((11S,13S)-11-hydroxy-3-methoxy-13-methyl-7,8,9,11,12,13,14,15,16,17-decahydro-6H-cyclopenta[a]phenanthren-17-yl)ethanone li. (E)-1-((11S,13S)-3,11-dihydroxy-13-methyl-7,8,9,11,12,13,14,15,16,17-decahydro-6H-cyclopenta[a]phenanthren-17-yl)ethanone oxime lii. (E)-1-((11S,13S)-3,11-dihydroxy-13-methyl-7,8,9,11,12,13,14,15,16,17-decahydro-6H-cyclopenta[a]phenanthren-17-yl)ethanone oxime liii. (11S,13S)-17-(2-hydroxypropan-2-yl)-13-methyl-7,8,9,11,12,13,14,15,16,17-decahydro-6H-cyclopenta[a]phenanthrene-3,11-diol liv. (11S,13R)-17-ethyl-13-methyl-7,8,9,11,12,13,14,15,16,17-decahydro-6H-cyclopenta[a]phenanthrene-3,11-diol lv. (8S,9S,10R,11S,13S,14S,Z)-11-hydroxy-17-(hydroxyimino)-10,13-dimethyl-6,7,8,9,10,11,12,13,14,15,16,17-dodecahydro-3H-cyclopenta[a]phenanthren-3-one lvi. (8S,9S,10R,11S,13S,14S)-17-amino-11-hydroxy-10,13-dimethyl-6,7,8,9,10,11,12,13,14,15,16,17-dodecahydro-3H-cyclopenta[a]phenanthren-3-one lvii. (8S,9S,10R,11S,13S,14S)-11-hydroxy-10,13-dimethyl-6,7,8,9,10,11,12,13,14,15,16,17-dodecahydro-3H-cyclopenta[a]phenanthren-3-one lviii. (8S,9S,10R,11S,13S,14S,17S)-11,17-dihydroxy-10,13,17-trimethyl-6,7,8,9,10,11,12,13,14,15,16,17-dodecahydro-3H-cyclopenta[a]phenanthren-3-one lix. (11R,13S,17S)-11,13,17-trimethyl-7,8,9,11,12,13,14,15,16,17-decahydro-6H-cyclopenta[a]phenanthrene-3,11,17-triol lx. (11S,13S)-13-methyl-7,8,9,11,12,13,14,15,16,17-decahydro-6H-cyclopenta[a]phenanthrene-3,11-diol lxi. (11S,13S,17S)-17-amino-13-methyl-7,8,9,11,12,13,14,15,16,17-decahydro-6H-cyclopenta[a]phenanthrene-3,11-diol lxii. (11S,13S,Z)-3,11-dihydroxy-13-methyl-7,8,9,11,12,13,15,16-octahydro-6H-cyclopenta[a]phenanthren-17(14H)-one oxime lxiii. (4aR,5S,6aS,7S)-5-hydroxy-4a,6a-dimethyl-7-(2-methyl-1,3-dioxolan-2-yl)-4,4a,4b,5,6,6a,7,8,9,9a,9b,10-dodecahydro-1H-indeno[5,4-f]quinolin-2(3H)-one lxiv. (4aR,5S,6aS,7S)-5-hydroxy-4a,6a-dimethyl-2-oxo-2,3,4,4a,4b,5,6,6a,7,8,9,9a,9b,10-tetradecahydro-1H-indeno[5,4-f]quinoline-7-carboxylic acid The present invention includes within its scope the salts and isomers. Compounds of the present invention after being novel may in some cases form salts which are also within the scope of this invention. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise a basic moiety such as an amino group). Also included herein are quaternary ammonium salts such as alkyl ammonium salts. Pharmaceutically acceptable (i.e., non-toxic, physiologically acceptable) salts are preferred.

All stereoisomer's of the present compounds, such as those which may exist due to asymmetric carbons on the R substituents of the compound, including enantiomeric and diastereomeric forms, are contemplated within the scope of this invention. The Compounds of the present invention may be present in their enantiomeric pure forms or their mixtures.

B. Salts and Isomers and Counter Ions

The present invention includes within its scope the salts and isomers. Compounds of the present invention after being novel may in some cases form salts which are also within the scope of this invention. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise a basic moiety such as an amino group). Pharmaceutically acceptable (i.e., non-toxic, physiologically acceptable) salts are preferred. All stereoisomer's of the present compounds, such as those which may exist due to asymmetric carbons on the R substituents of the compound, including enantiomeric and diastereomeric forms, are contemplated within the scope of this invention. The Compounds of the present invention may be present in their enantiomeric pure forms or their mixtures.

C. Composition of the Present Invention

The invention thus provides the use of the novel compounds as defined herein for use in human or veterinary medicine. The compound for use as a pharmaceutical may be presented as a pharmaceutical composition. The invention therefore provides in a further aspect a pharmaceutical composition comprising the novel compounds of the invention along with pharmaceutically acceptable excipients/carriers thereof and optionally other therapeutic and/or prophylactic ingredients. The excipients/carriers must be "acceptable" in the sense of being compatible with the other ingredients of the composition and not deleterious to the recipient thereof. Suitably the pharmaceutical composition will be in an appropriate formulation.

The pharmaceutical formulations may be any formulation and include those suitable for oral, intranasal, or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both, and then, if necessary, shaping the product into the desired formulation. For these purposes the compounds of the present invention may be administered orally, topically, intranasally, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasteral injection or infusion techniques. In addition to the treatment of warm-blooded animals such as mice, rats, horses, dogs, cats, etc., the compounds of the invention are effective in the treatment of humans.

D. Use of Compounds of the Present Invention

The compounds of the present invention are used in diseases and disorders pertaining to mitochondrial biogenesis. The mitochondrial biogenesis-mediated disease is selected from the group comprising skeletal or cardiac muscle diseases associated with ischemia, or impaired or inadequate blood flow, diseases associated with genetic disorders that directly or indirectly affect the number, structure, or function of mitochondria, diseases associated with impaired neurological function associated with decreased mitochondrial number or function, diseases associated with loss of number, loss of function, or loss of correct, optimally efficient internal organization of skeletal muscle cells or cardiac muscle cells, metabolic diseases, and conditions associated with liver cell injury and altered fatty acid metabolism.

The mitochondrial biogenesis-mediated disease is selected from the group comprising acute coronary syndrome, myocardial infarction, angina, renal injury, renal ischemia, diseases of the aorta and its branches, injuries arising from medical interventions, atherosclerosis, trauma, diabetes, hyperlipidemia, vascular stenosis, peripheral arterial disease, vasculopathy, and vasculitis. The mitochondrial biogenesis-mediated disease is selected from the group consisting of Friedreich's ataxia, muscular dystrophy, Duchenne muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, spinal muscular atrophy and Emery-Dreifuss muscular dystrophy. Huntington's disease, parkinson's disease, alzheimer's disease, and amyotrophic lateral sclerosis. The mitochondrial biogenesis-mediated disease is selected from the group comprising sarcopenia, congestive heart failure, aging, myocarditis, myositis, polymyalgia rheumatic, polymyositis, HIV, cancer and/or the side effects of chemotherapy targeting the cancer, malnutrition, aging, inborn errors of metabolism, trauma, and stroke or other types of neurological impairment like hepatic steatosis, hepatic fibrosis, cirrhosis, and hepatocyte or stellate cell injury.

The compounds of the present invention may be used in treating or preventing the adverse effects of administration of compounds which exhibit mitochondrial toxicity The compounds of the present invention are capable of improving muscle structure or function; improving mitochondrial effects associated with exercise; enhancing the capacity for exercise in those limited by age, inactivity, diet, or diseases; enhancing muscle health and function in response to exercise; enhancing muscle health and function in the clinical setting of restricted capacity for exercise; enhancing recovery of muscles from vigorous activity or from injury associated with vigorous or sustained activity.

The compounds of the present invention are capable of enhancing sports performance and endurance, building muscle shape and strength, or facilitating recovery from the muscle related side effects of training or competition.

E. Dose of the Compounds of the Present Invention

In further embodiments, the methods disclosed herein comprise the administration of compounds of the disclosure in a total daily dose of about 0.001 mg/kg/dose to about 10 mg/kg/dose, alternately from about 0.3 mg/kg/dose to about 3 mg/kg/dose. In another embodiment the dose range is from about 0.1 to about 1 mg/kg/day. Generally between about 0.01 mg and about 0.1 gram per day can be administered; alternately between about 2.5 mg and about 200 mg can be administered. The dose may be administered in as many divided doses as is convenient.

In further embodiments, the desired concentration is maintained for at least 30 minutes, 1 hour, 3 hours, 6 hours, 12 hours, 24 hours, 48 hours, 72 hours, or more. In yet further embodiments, the desired concentration is achieved at least once during each 12-hour period over at least 24 hours, 48 hours, 72 hours, 1 week, one month, or more; or at least once during each 24-hour period over at least 48 hours, 72 hours, 1 week, one month, or more. In order to maintain a desired concentration for a desired time, multiple doses of one or more compounds may be employed. The dosing interval may be determined based on the clearance half-life for each compound of interest from the body.

It is envisaged within the scope of the present invention that the compounds may be administered in combination with other therapeutic agents. The compounds may be administered together or sequentially.

Without being limited by theory, it is submitted that the novel compounds of the present invention exhibit substantially different pharmacokinetic and pharmacodynamic profiles. The invention is described in detail herein below with respect to the following examples which are provided merely for illustration. However, these examples may not be construed to restrict the scope of the invention. Any embodiments that may be apparent to a person skilled in the art are deemed to fall within the scope of present invention.

Example 1: Preparation of Compounds of the Present Invention

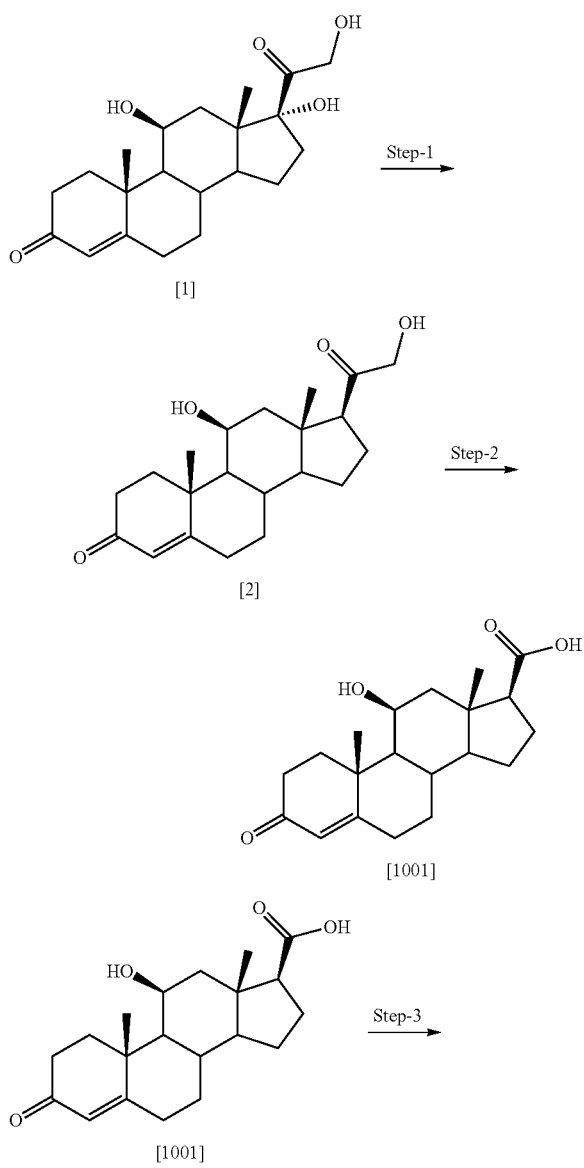

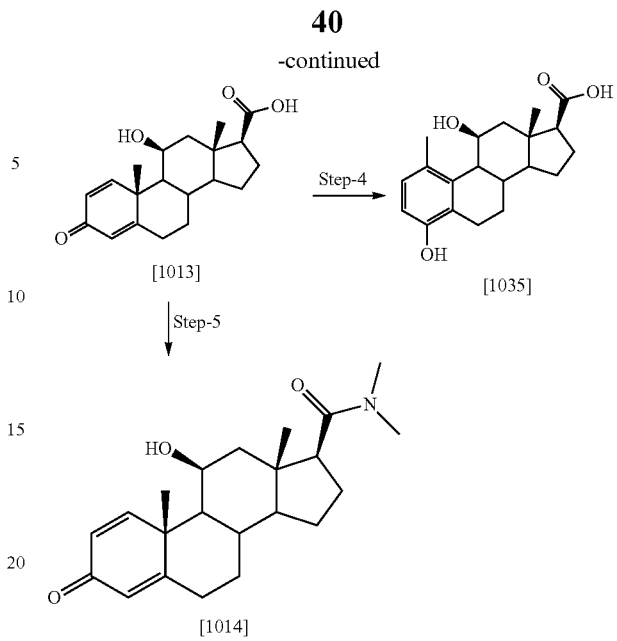

Step 1:
Compound[1] (500 mg, 1.38 mmol) was taken in ACN (200 ml) and trimethyl silyl iodide (1.17 ml, 8.28 mmol) was added dropwise. The reaction mixture was stirred at room temperature for 20 min After completion, the reaction was quenched by 10% sodium thiosulfate (50 ml), washed with saturated NaHCO$_3$ and extracted with ethyl acetate. Organic layer was separated; dried over Na$_2$SO$_4$ and evaporated under reduced pressure to obtain [2] as light yellow solid (450 mg, 94%). MS (ESI) m/z (M$^+$+1) 347.

Step 2:
To a stirred solution of [2] (1.0 g, 2.89 mmol) in acetone, a water (50 ml) solution of NaIO$_4$ (2.47 g, 11.5 mmol) was added and reaction mixture was stirred for 2 hr at rt. Reaction was quenched with water (25 ml), extracted with EtOAc. Organic layer was separated, dried over Na2SO4 and evaporated under reduced pressure to obtain [1001] as white solid (850 mg, 88%), MS (ESI) m/z (M$^+$+1) 333.

Step 3:
A solution of compound [1001] (1.0 g, 3.01 mmol) in dioxane (50 ml) was treated with TBDMSCl (0.022 g, 0.152 mmol) followed by DDQ (0.90 g, 3.95 mmol) at 0° C. The mixture was allowed to stirred at RT for 2 hr. Reaction mixture was diluted with ethyl acetate and washed with saturated sodium carbonate solution and brine, dried over sodium sulfate, concentrated and purified by silica gel column chromatography eluting with 3% MeOH:DCM to give compound [1013] as a light yellow solid (0.61 g, 61% yield). MS (ESI) m/z (M++1) 331.

Step 4:
The compound [1013] (0.5 g, 1.51 mmol) was taken in pyridine (15 mL) and zinc dust (19.6 g, 30.2 mmol) was added to it, followed by addition of water (0.5 ml). The reaction mixture was heated at 115° C. for 90 mins and cooled, filtered, washed with 0.1 N HCl and extracted with DCM (2×100 mL). The organic layer was dried over Na2SO4, concentrated and purified by silica gel column chromatography by eluting with 40% ethyl acetate:hexane to give compound [24] as a white solid to obtain product [1035] as off white solid. Yield (0.38 g, 76% yield). MS (ESI) m/z (M$^+$+1) 331.

Step-5:

A solution of [1013] (0.2 mg, 0.606 mmol) in DMF (3 ml), EDC.HCl (0.17 mg, 0.909 mmol) was added and mixture was stirred at room temperature for 30 min. Dimethyl amine 2M solution in THF (1.5 ml, 3.03 mmol) was added followed by N-methyl morpholine (0.15 g, 1.51 mmol) and stirring was continued for 18 hrs at room temperature. The reaction mixture was quenched with brine (50 ml), extracted with ethyl acetate (3×100 ml). The combined organic extract was dried ($Na_2SO_4$) concentrated to obtain crude which was purified by column chromatography (silica gel 100-200 mesh) to obtain compound [1014] as off white solid (0.125 g, 58% yield). MS (ESI) m/z ($M^+$+1) 358.

A few illustrated examples of this series synthesized based on example 1 include 1014, 1041-1050

Example 2 (a): Preparation of Compounds of the Present Invention

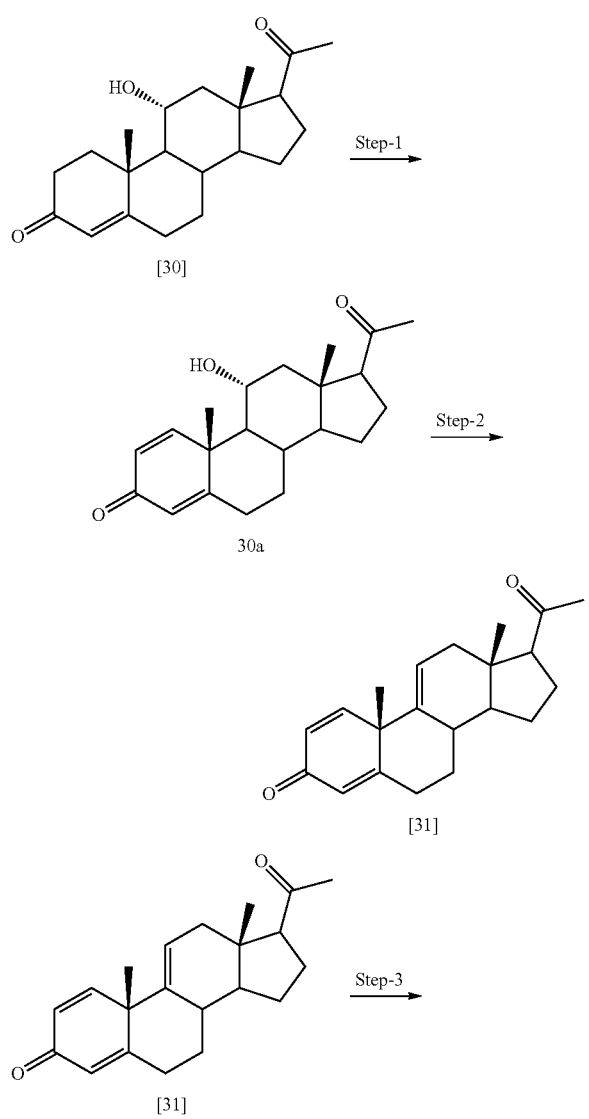

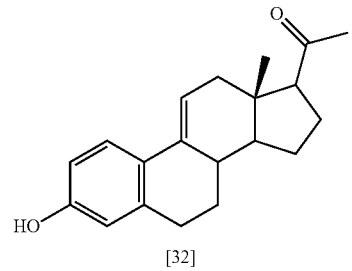

Step 1:

A solution of compound [30] (1.0 g, 3.04 mmol) in dioxane (50 ml) was treated with TBDMSCl (0.022 g, 0.152 mmol) followed by DDQ (0.90 g, 3.95 mmol) at 0° C. The mixture was allowed to stirred at RT for 2 hr. Reaction mixture was diluted with ethyl acetate and washed with saturated sodium carbonate solution and brine, dried over sodium sulfate and purified by silica gel column chromatography eluting with 40% ethyl acetate:hexane to give compound [30a] as a white solid (0.45 g, 45% yield). MS (ESI) m/z ($M^+$+1) 325.

Step 2:

A solution of compound [30a] (1 g, 3.08 mmol) in Dry THF (5 ml) was taken. To this $PCl_5$ (1.15 g, 5.55 mmol) was added at −80° C. and stirred at 30 mins. After completion, 10% NaOH solution was added to adjust pH upto 7 and organic layer was extracted with ethyl acetate. Organic phase was dried over sodium sulfate and was evaporated under reduced pressure to get crude residue. The crude residue was purified by silica gel column chromatography by eluting with 15-20% ethyl acetate:hexane to obtain brown solid[31]. (0.80 g, 77% yield). MS (ESI) m/z ($M^+$+1) 313.

Step 3:

The compound [31] (0.5 g, 1.60 mmol) was taken in pyridine (15 mL) and Zn dust (20.8 g, 32 mmol) was added to it followed by addition of. 0.5 ml of water. The reaction mixture was heated at 115° C. for 90 mins for completion. Reaction mixture was cooled, filtered, washed with 0.1 N HCl and extracted with DCM (2×100 mL). The organic layer was dried over $Na_2SO_4$, concentrated to obtain product [32] as off white solid. (0.35 g, 73% yield), MS (ESI) m/z ($M^+$+1) 297.

Example 2b: Preparation of Compounds of the Present Invention

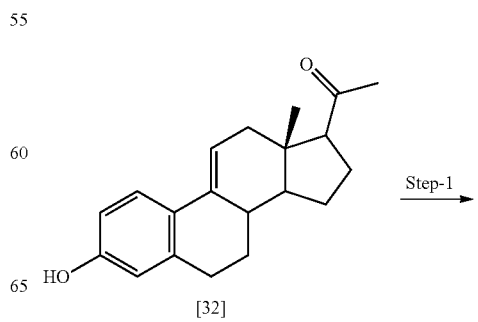

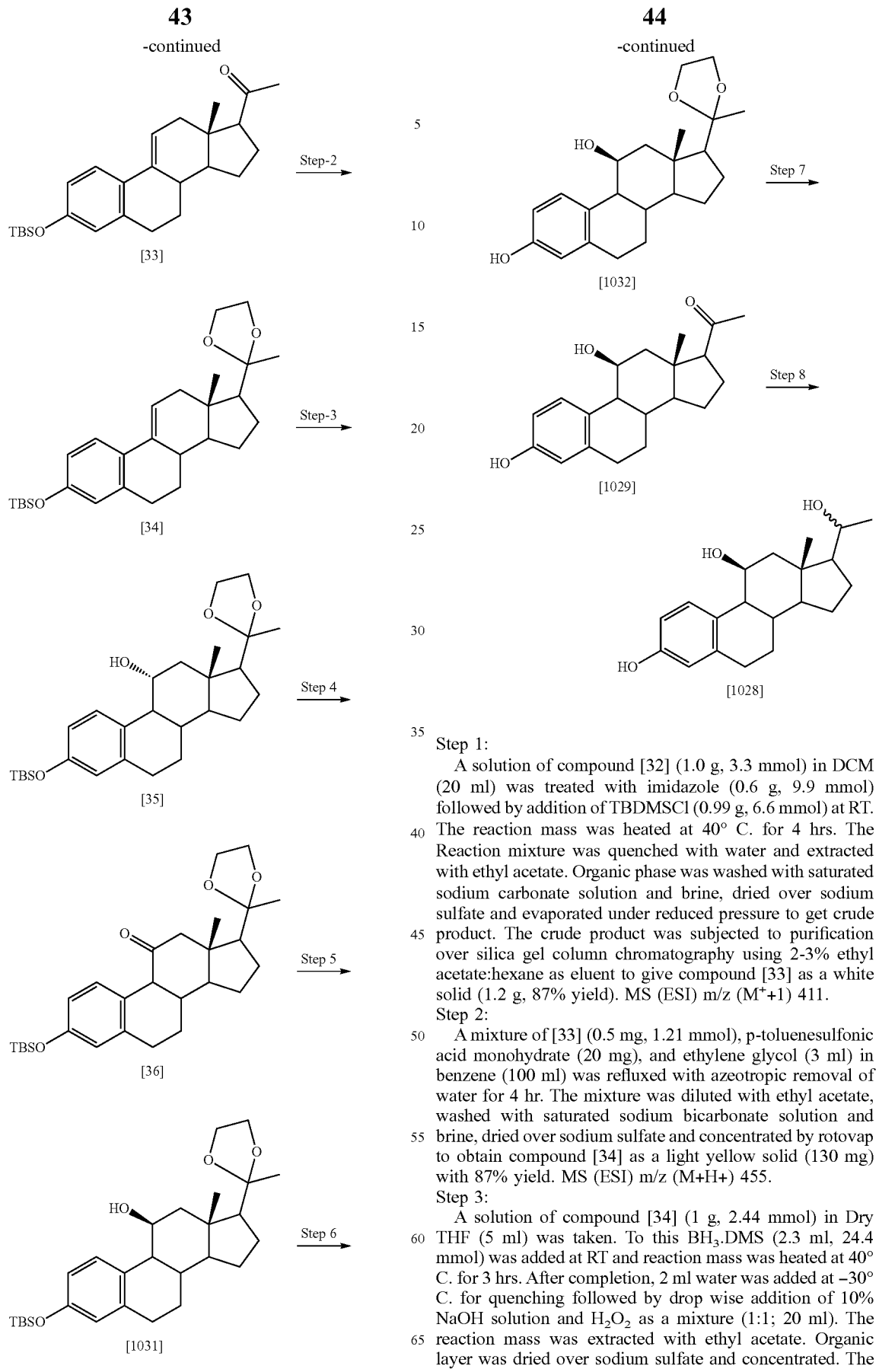

Step 1:

A solution of compound [32] (1.0 g, 3.3 mmol) in DCM (20 ml) was treated with imidazole (0.6 g, 9.9 mmol) followed by addition of TBDMSCl (0.99 g, 6.6 mmol) at RT. The reaction mass was heated at 40° C. for 4 hrs. The Reaction mixture was quenched with water and extracted with ethyl acetate. Organic phase was washed with saturated sodium carbonate solution and brine, dried over sodium sulfate and evaporated under reduced pressure to get crude product. The crude product was subjected to purification over silica gel column chromatography using 2-3% ethyl acetate:hexane as eluent to give compound [33] as a white solid (1.2 g, 87% yield). MS (ESI) m/z (M$^+$+1) 411.

Step 2:

A mixture of [33] (0.5 mg, 1.21 mmol), p-toluenesulfonic acid monohydrate (20 mg), and ethylene glycol (3 ml) in benzene (100 ml) was refluxed with azeotropic removal of water for 4 hr. The mixture was diluted with ethyl acetate, washed with saturated sodium bicarbonate solution and brine, dried over sodium sulfate and concentrated by rotovap to obtain compound [34] as a light yellow solid (130 mg) with 87% yield. MS (ESI) m/z (M+H+) 455.

Step 3:

A solution of compound [34] (1 g, 2.44 mmol) in Dry THF (5 ml) was taken. To this BH$_3$.DMS (2.3 ml, 24.4 mmol) was added at RT and reaction mass was heated at 40° C. for 3 hrs. After completion, 2 ml water was added at −30° C. for quenching followed by drop wise addition of 10% NaOH solution and H$_2$O$_2$ as a mixture (1:1; 20 ml). The reaction mass was extracted with ethyl acetate. Organic layer was dried over sodium sulfate and concentrated. The crude residue was purified by silica gel column chromatography using 60% ethyl acetate:hexane as eluent to obtain yellow solid[35]. (0.6 g, 52% yield). MS (ESI) m/z (M$^+$−1). 473

Step 4:

A solution of compound [35] (0.5 g, 1.16 mmol) in DCM (20 ml) was treated with Dess martin periodinane (1.97 g, 4.65 mmol) at RT for 20 hr. Reaction mixture was diluted with DCM and washed with saturated sodium carbonate solution and brine, dried over sodium sulfate and purified by silica gel column chromatography using 30% ethyl acetate in hexane as eluent to give compound [36] as a white solid (0.31 g, 62% yield). MS (ESI) m/z (M$^+$+1). 471

Step 5:

A solution of compound [36] (0.2 g, 0.47 mmol) in ethanol (50 ml) was added sodium borohydride (0.034 g, 0.93 mmol) at 0° C. The reaction was stirred in an ice bath for 8 hr. The reaction was quenched with water (5 ml) and concentrated under vacuum until solid appears. The solid residue was purified by silica gel column chromatography (2% MeOH:DCM as an eluent) to give compound [1031] as a white solid (0.15 g, Yield 75%). MS (ESI) m/z (M$^+$+1).473

Step 6:

A solution of compound [1031] (0.2 g, 0.423 mmol) in THF (10 ml) was treated with TBAF 1M solution in THF (0.85 ml, 0.847 mmol) at 0° C. The mixture was allowed to stirred at RT for 1 hr. Reaction mixture was diluted with ethyl acetate and washed with saturated sodium carbonate solution and brine, dried over sodium sulfate and purified by silica gel column chromatography eluting with 40% Ethyl acetate in Hexane to give compound [1032] as a light yellow solid (0.125 g, 82% yield). MS (ESI) m/z (M$^+$+1) 359

Step 7

A solution of compound [1032] (0.1 g, 0.21 mmol) in acetone (7 ml) and water (3 ml) was treated with concentrated sulfuric acid (0.5 ml) at 0° C. The mixture was allowed to stirred for 2 hr. Reaction mixture was diluted with ethyl acetate and washed with saturated sodium carbonate solution and brine, dried over sodium sulfate and purified purified by silica gel column chromatography eluting with 40% Ethyl acetate:Haxene to give compound [1029] as a white solid (0.05 mg, 75% yield). MS (ESI) m/z (M$^+$+1) 315.

Step 8:

A solution of compound [1029] (0.1 g, 0.317 mmol) in ethanol (50 ml) was added sodium borohydride (0.024 g, 0.634 mmol) at 0° C. The reaction was stirred in an ice bath for 4 hr. The reaction was quenched with water (5 ml) and concentrated under vacuum until solid appears. The solid residue was purified by silica gel column chromatography (2% MeOH:DCM as an eluent) to give compound [1028] as a white solid (0.080 g, Yield 80%). MS (ESI) m/z (M$^+$+1) 319. A few illustrated examples of this series synthesized based on example 2b include 1028, 1051-1055

Example 3: Preparation of Compounds of the Present Invention

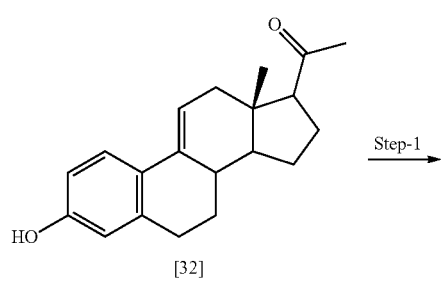

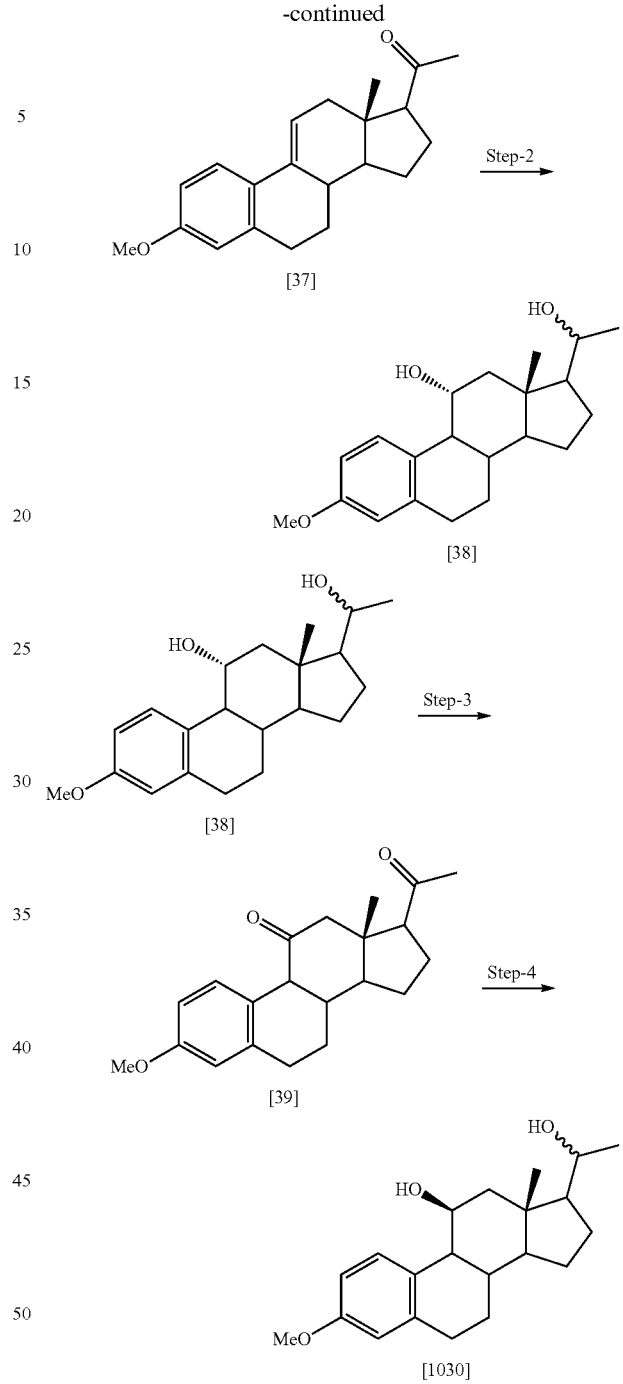

Step 1:

A solution of compound [32] (1.0 g, 3.3 mmol) in DMF:Acetone (20 ml) was treated with MeI (1.4 g, 9.9 mmol) and K$_2$CO$_3$ (1.36 g, 9.9 mmol) and catalytic amount of 18-crown-6 at RT. The reaction mass was heated at 40° C. for 14 hrs and progress of the reaction was monitored by TLC. The reaction mixture was cooled to room temperature and filtered. The filtrate was concentrated under reduced pressure to evaporate excess of the solvent. Residual mass was dissolved in water and extracted with ethyl acetate. Organic layer was washed with water and brine, dried over sodium sulfate and purified by silica gel column chromatography using with 2-3% ethyl acetate in hexane as eluents to give compound [37] as a white solid (1.2 g, 87% yield), MS (ESI) m/z (M⁺+1) 311.

Step 2:

Compound[38] was synthesized using the same procedure as mentioned in example 2b. Yield 54%. MS (ESI) m/z (M⁺+1) 331.

Step 3:

Compound[39] was synthesized using the same procedure as mentioned in example 2b. Yield 65%. MS (ESI) m/z (M⁺+1) 327.

Step 4:

Compound [1030] was synthesized using the same procedure as mentioned in example 2b. Yield 70%. MS (ESI) m/z (M⁺+1) 331.

Example 4: Preparation of Compounds of the Present Invention

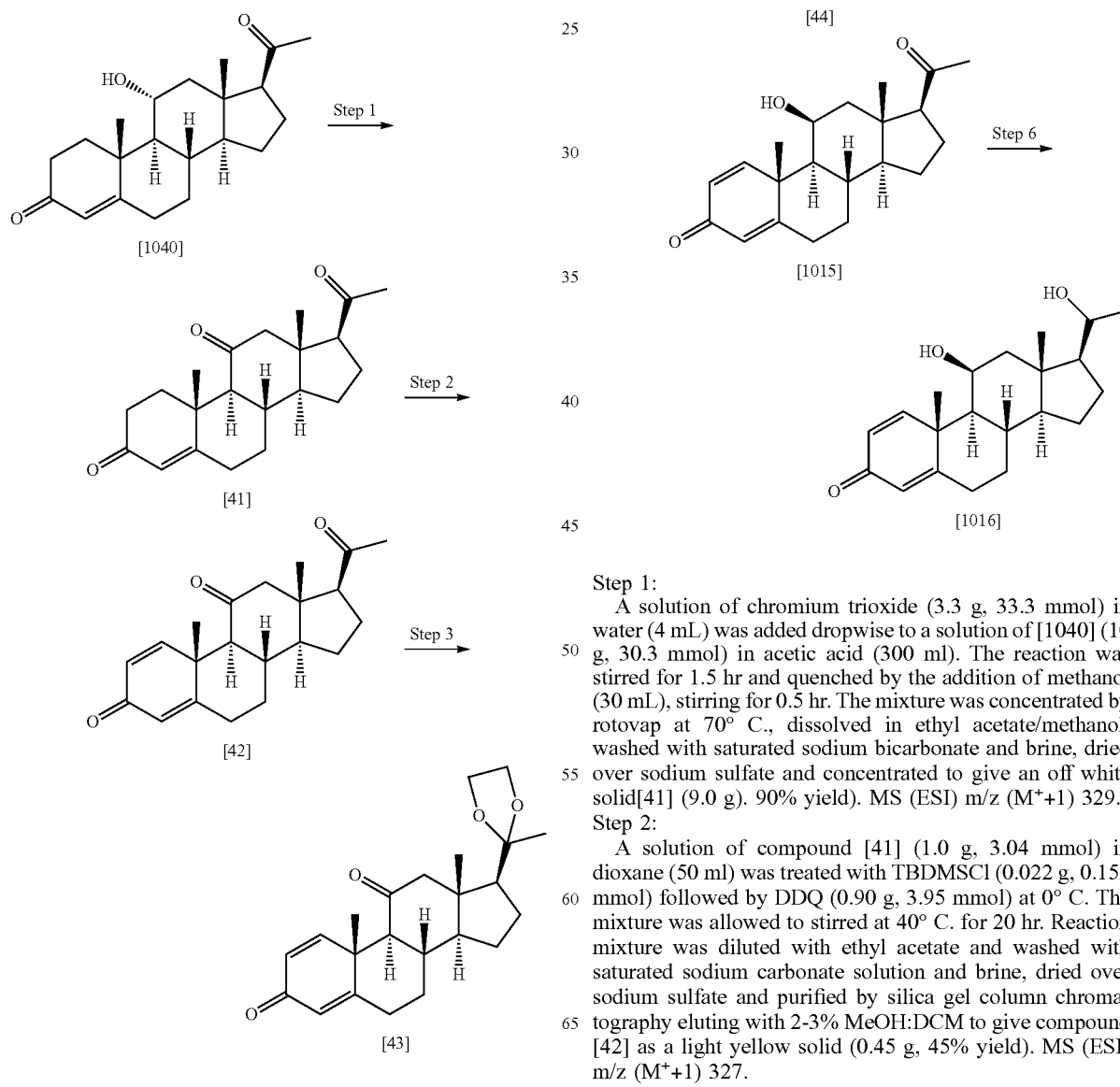

Step 1:

A solution of chromium trioxide (3.3 g, 33.3 mmol) in water (4 mL) was added dropwise to a solution of [1040] (10 g, 30.3 mmol) in acetic acid (300 ml). The reaction was stirred for 1.5 hr and quenched by the addition of methanol (30 mL), stirring for 0.5 hr. The mixture was concentrated by rotovap at 70° C., dissolved in ethyl acetate/methanol, washed with saturated sodium bicarbonate and brine, dried over sodium sulfate and concentrated to give an off white solid[41] (9.0 g). 90% yield). MS (ESI) m/z (M⁺+1) 329.

Step 2:

A solution of compound [41] (1.0 g, 3.04 mmol) in dioxane (50 ml) was treated with TBDMSCl (0.022 g, 0.152 mmol) followed by DDQ (0.90 g, 3.95 mmol) at 0° C. The mixture was allowed to stirred at 40° C. for 20 hr. Reaction mixture was diluted with ethyl acetate and washed with saturated sodium carbonate solution and brine, dried over sodium sulfate and purified by silica gel column chromatography eluting with 2-3% MeOH:DCM to give compound [42] as a light yellow solid (0.45 g, 45% yield). MS (ESI) m/z (M⁺+1) 327.

Step 3:

Compound[43] was synthesized using the same procedure as mentioned in example 2b. Yield 78%. MS (ESI) m/z (M$^+$+1) 371.

Step 4:

Compound [44] was synthesized using the same procedure as mentioned in example 2b. Yield 78%. MS (ESI) m/z (M$^+$+1) 373.

Step 5:

Compound[45] was synthesized using the same procedure as mentioned in example 2b. Yield 78%. MS (ESI) m/z (M$^+$+1) 329.

Step 6:

Compound[1016] was synthesized using the same procedure as mentioned in example 2b. Yield 78%. MS (ESI) m/z (M$^+$+1) 331.

Example 5: Preparation of Compounds of the Present Invention

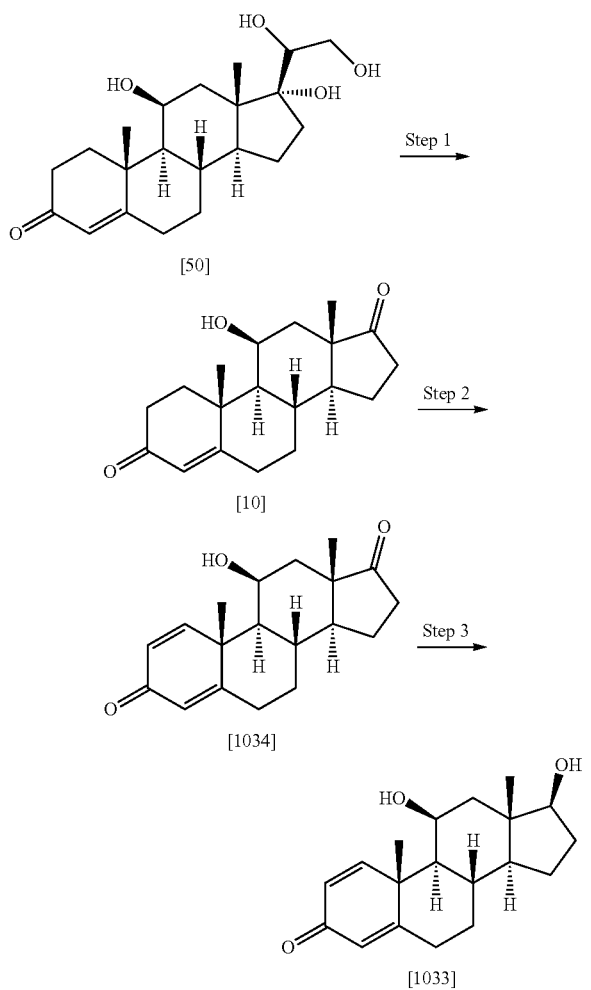

Step 1:

A solution of compound [50] (0.21 mg, 0.6 mmol) in THF (4 ml) and methanol (2 ml) was treated with a hot solution of sodium metaperiodate (383 mg, 1.8 mmol) in water and stirred for 1 hr at RT. The mixture was diluted with water (10 ml) and concentrated by rotovap until a precipitate forms which is filtered, washed with water and dried under hard vacuum to give compound [10] as a white solid (0.15 mg). Yield 86%. MS (ESI) m/z (M−1) 303.

Step 2:

Synthetic procedure is same as in example 2 to provide [1034]. Yield 80%. MS (ESI) m/z (M$^+$+1) 301.

Step 3:

Synthetic procedure is same as that of example 2 to provide [1033]. Yield 75%. MS (ESI) m/z (M$^+$+1) 303.

Some illustrated examples of this series synthesized based on example 5 include 1033, 1056-1059

Example 6a: Preparation of Compounds of the Present Invention

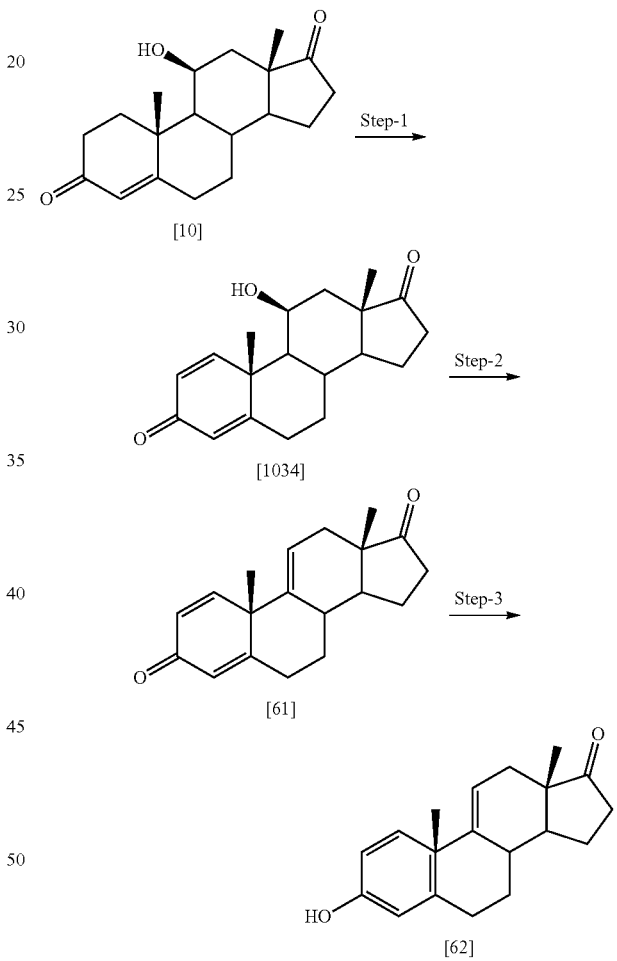

Step 1:

Compound was synthesized using the same procedure as mentioned in example 2a to provide [1034]. Yield 75%. MS (ESI) m/z (M$^+$+1) 301.

Step 2:

Compound was synthesized using the same procedure as mentioned in example 2a to yield [61]. Yield 80%. MS (ESI) m/z (M$^+$+1) 283.

Step 3:

Compound was synthesized using the same procedure as mentioned in example 2a to result in [62]. Yield 78%. MS (ESI) m/z (M$^+$+1) 269.

Example 6b

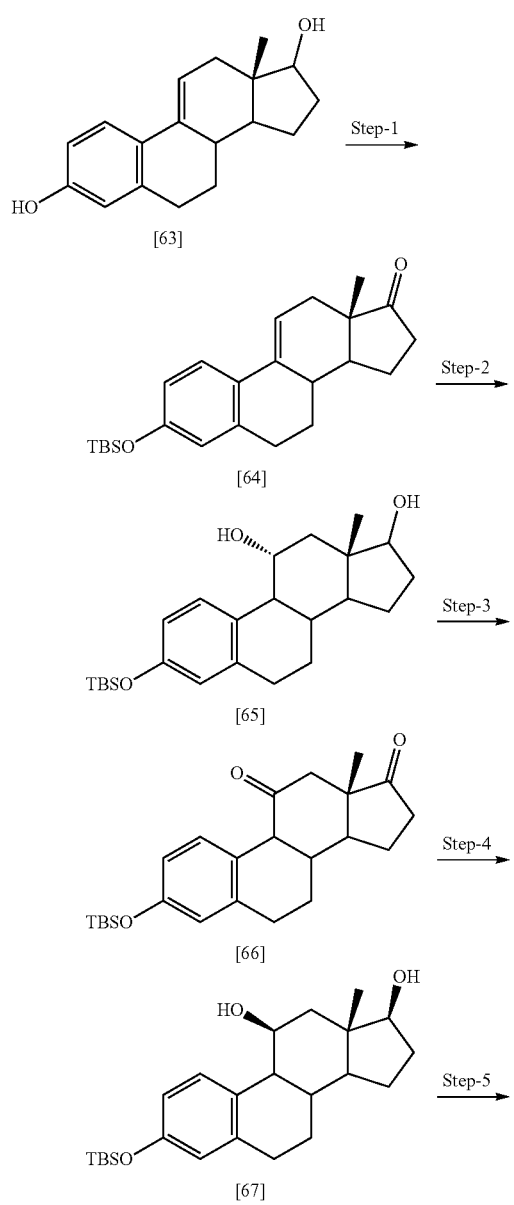

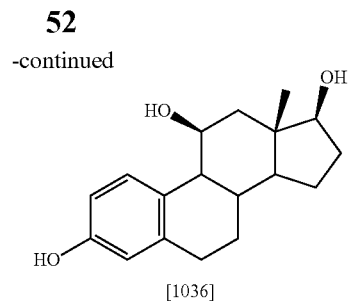

Step 1:
Compound was synthesized using the same procedure as mentioned in example 2b to provide [64]. Yield 70%. MS (ESI) m/z (M++1) 383.

Step 2:
Compound was synthesized using the same procedure as mentioned in example 2b to provide [65]. Yield 56%. MS (ESI) m/z ($M^+$+1) 403.

Step 3:
Compound was synthesized using the same procedure as mentioned in example 2b to provide [66]. Yield 71%. MS (ESI) m/z ($M^+$+1) 399.

Step 4:
Compound was synthesized using the same procedure as mentioned in example 2b to result in [67]. Yield 78%. MS (ESI) m/z ($M^+$+1) 403.

Step 5:
A solution of compound [67] (0.1 g, 0.248 mmol) in THF (10 ml) was treated with TBAF 1M solution in THF (0.5 ml, 0.497 mmol) at 0° C. The mixture was allowed to stirred at RT for 1 hr. Reaction mixture was diluted with ethyl acetate and washed with saturated sodium carbonate solution and brine, dried over sodium sulfate and purified by silica gel column chromatography eluting with 40% ethyl acetate in hexane to give compound [1036] as a light yellow solid (0.05 g, 70% yield). MS (ESI) m/z ($M^+$+1) 289.

A few illustrated examples of this series synthesized based on example 6a & 6b include 1060-1063

Example 7a: Preparation of Compounds of the Present Invention

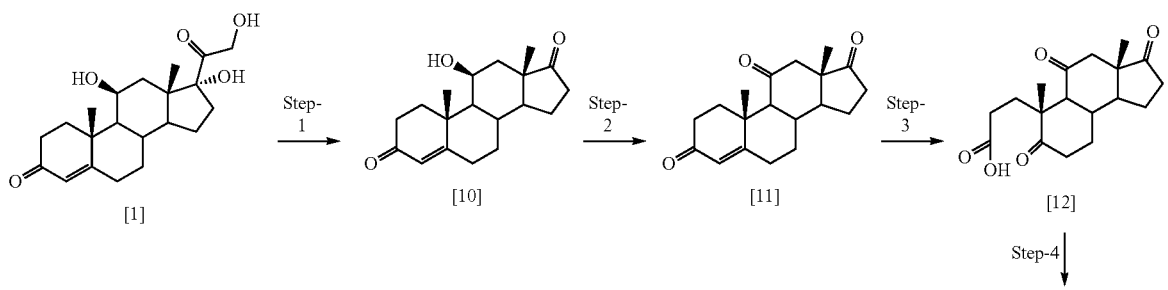

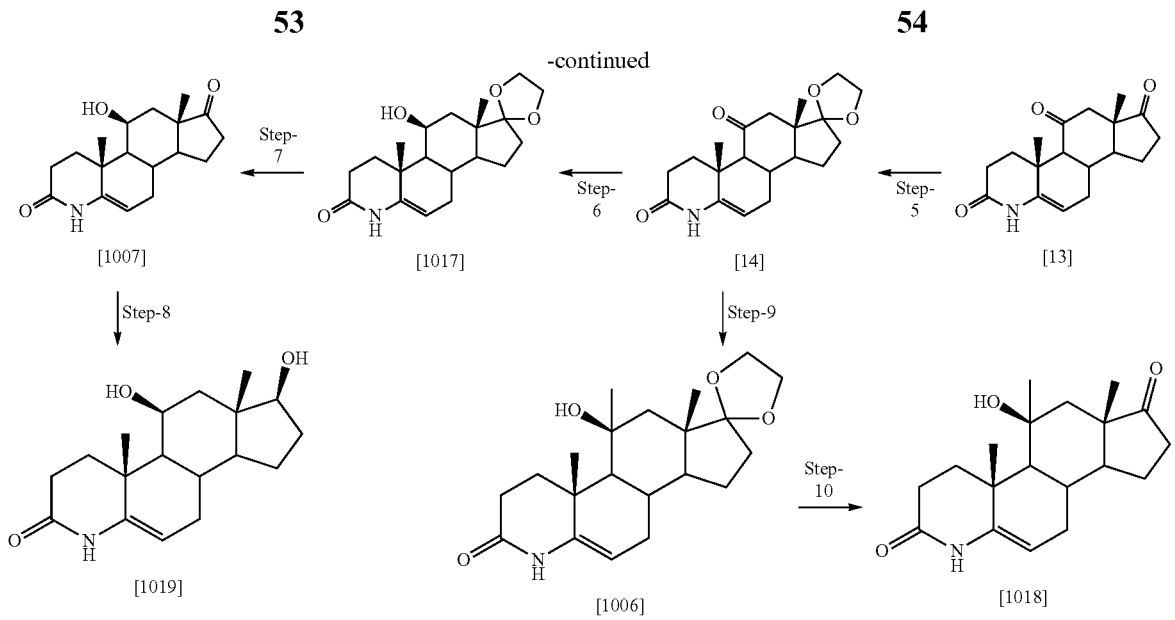

Step 1:

A solution of hydrocortisone [1] (2.0 g, 5.52 mmol) in EtOH—CH2Cl2 (40 ml, 1:1) was treated with NaBH4 (84 mg, 2.20 mmol). After 2 hr, acetone (10 ml) was added followed by water 910 ml) and NaIO4 (2.95 g, 13.8 mmol). The solution was stirred at room temperature overnight followed by the addition of water (200 ml), extraction with CHCl3 and flushing through a silica gel plug. After evaporation of the solvent, 1.5 g of ketone [10] was obtained as a white solid with 90% yield. MS (ESI) m/z (M+H$^+$) 303.

Step 2:

A solution of chromium trioxide (0.364 g, 3.64 mmol) in water (1 mL) was added drop wise to a solution of compound [10] (1 g, 3.31 mmol) in acetic acid (30 ml). The reaction was stirred for 1.5 hr and quenched by the addition of methanol (30 mL) while stirring for 0.5 hr. The mixture was concentrated by rotovap at 70° C., dissolved in ethyl acetate/methanol, washed with saturated sodium bicarbonate and brine, dried over sodium sulfate and concentrated to give compound [11] as an off white solid (0.9 g) with 90% yield. MS (ESI) m/z (M+H+) 301.

Step 3:

To a solution of [11] (0.9 g, 3.0 mmol) in tert-butanol (10 ml), anhydrous sodium carbonate (0.509 g, 4.8 mmol) and water (1 ml) were added and the reaction mixture was refluxed. A solution of sodium periodate (5.3 g, 24.9 mmol) and potassium permanganate (66 mg, 0.42 mmol) in water (14 ml) was added dropwise to the refluxed reaction mixture and refluxing was maintained for an additional 3 hr. The precipitate thus formed was filtered, washed with water. The filtrate was acidified with 5M HCl and extracted with dichloromethane. The organic phase was dried with anhydrous Na2SO4, filtered and filtrate was evaporated. The crude product was purified by silica gel column chromatography (MeOH:DCM 3:1) to obtained compound [12] as a yellow solid (320 mg) with 33% of yield. MS (ESI) m/z (M+H$^+$) 321.

Step 4:

To a mixture of compound [12] (320 mg, 1.0 mmol) in acetic acid (4 ml) was added ammonium acetate (231 mg, 3.0 mmol) and refluxed for 4 hr. The reaction mixture was evaporated to remove acetic acid and washed with water, neutralized with saturated bicarbonate solution and extracted with dichloromethane. The organic layer was separated and dried over anhydrous Na2SO4, filtered and filtrate was evaporated under vacuum to obtained crude product. The crude product was purified by silica gel column chromatography (2% MeOH:DCM as an eluent) to give [13] as a light yellow solid (130 mg) with 43% yield. MS (ESI) m/z (M+H$^+$) 302.

Step 5:

A mixture of [13] (130 mg, 0.43 mmol), p-toluenesulfonic acid monohydrate (13 mg), and ethylene glycol (1.3 ml) in benzene (100 ml) was refluxed with azeotropic removal of water for 8 hr. The mixture was diluted with ethyl acetate, washed with saturated sodium bicarbonate solution and brine, dried over sodium sulfate and concentrated by rotovap to obtain compound [14] as a light yellow solid (130 mg) with 87% yield. MS (ESI) m/z (M+H$^+$) 346.

Step 6:

A solution of compound [14] (50 mg, 0.14 mmol) in 7:3 ethanol/THF (10 ml) was added sodium borohydride (11 mg, 0.28 mmol) at 0° C. The reaction was stirred in an ice bath for 8 hr. The reaction was quenched with water (5 ml) and concentrated under vacuum until solid appears. The solid residue was purified by silica gel column chromatography (2% MeOH:DCM as an eluent) to give compound [1006] as a white solid (40 mg, Yield 80%). MS (ESI) m/z (M+H$^+$) 348.

Step 7:

A solution of compound [15] (40 mg, 0.11 mmol) in acetone (7 ml) and water (3 ml) was treated with concentrated sulfuric acid (0.1 ml) at 0° C. The mixture was allowed to stirred for 2 hr. Reaction mixture was diluted with ethyl acetate and washed with saturated sodium carbonate solution and brine, dried over sodium sulfate and purified purified by silica gel column chromatography eluting with 2-3% MeOH:DCM to give compound [1005] as a white solid (17 mg, 50% yield). MS (ESI) m/z (M+H+) 304.

Step 8:

A solution of compound [14] (40 mg, 0.13 mmol) in ethanol (10 ml) was added sodium borohydride (10 mg, 0.26 mmol) at 0° C. The reaction was stirred in an ice bath for 8 hr. The reaction was quenched with water (5 ml) and concentrated under vacuum until solid appears. The solid residue was purified by silica gel column chromatography (2% MeOH:DCM as an eluent) to give compound [1008] as a white solid (30 mg, Yield 75%). MS (ESI) m/z (M⁺+1) 306.

Step 9:

To a stirred solution of compound [14] (50 mg, 0.14 mmol) in dry THF (10 ml) was added MeLi dropwise (0.06 ml, 0.18 mmol) at 0° C. and allowed for 6 hr at room temperature. The reaction mixture was quenched with saturated solution of ammonium chloride and extracted with ethyl acetate. Organic phase dried over sodium sulfate, filter and filtrate was evaporated. The crude residue was purified by silica gel column chromatography eluting with 2%-3% MeOH:DCM to give compound [1006] as a light yellow solid (40 mg, 76% yield). MS (ESI) m/z (M+H+) 362

Step 10:

A solution of compound [1006] (40 mg, 0.11 mmol) in acetone (7 ml) and water (3 ml) was treated with concentrated sulfuric acid (0.1 ml) at 0° C. The mixture was allowed to stirred for 2 hr. Reaction mixture was diluted with ethyl acetate and washed with saturated sodium carbonate solution and brine, dried over sodium sulfate and purified purified by silica gel column chromatography eluting with 2%-3% MeOH:DCM to give compound [1007] as a light yellow solid (18 mg, 51% yield). MS (ESI) m/z (M+H+) 318.

Example 7b: Preparation of Compounds of the Present Invention

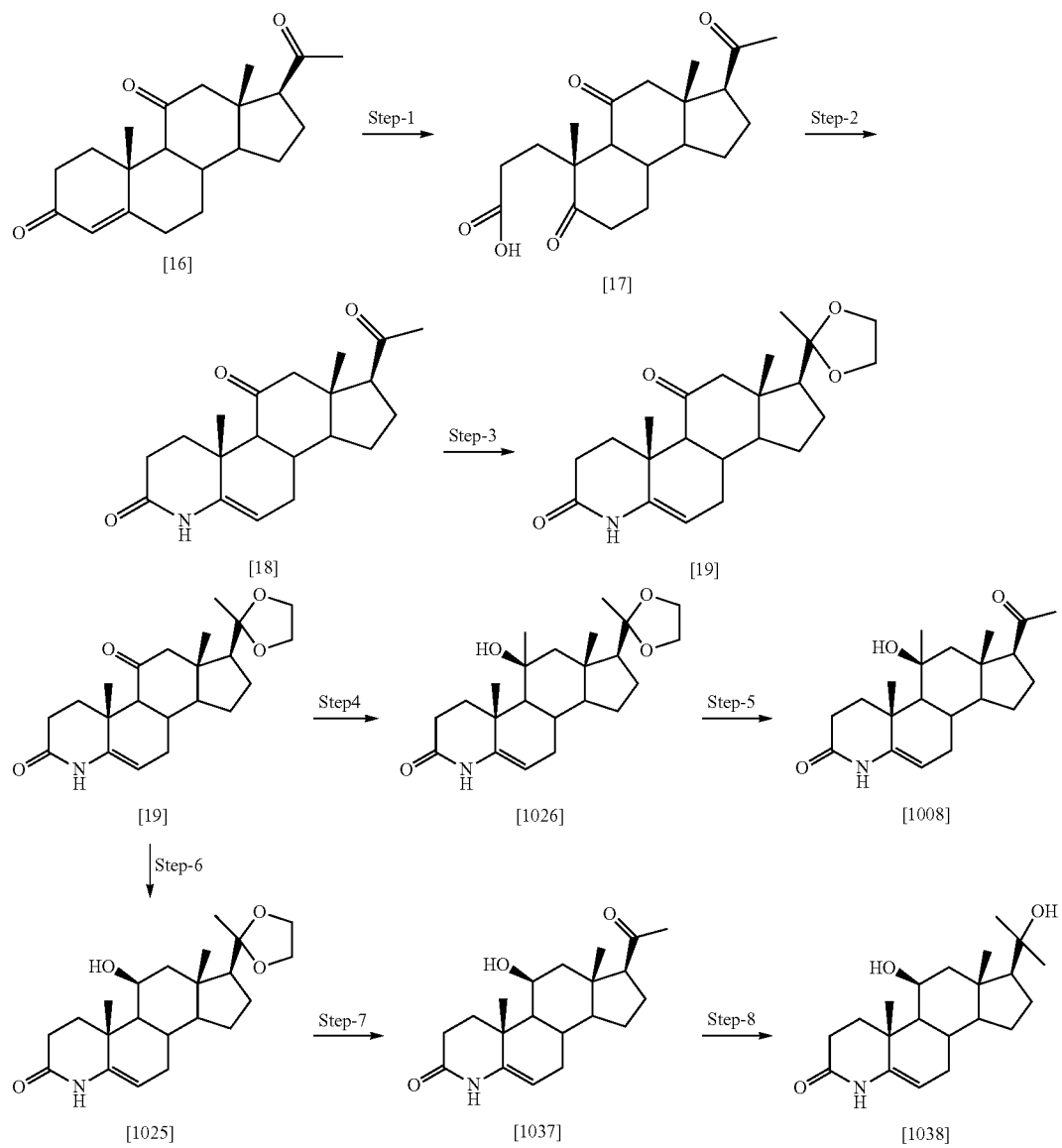

Step 1:

To a solution of [16] (3 g, 9.0 mmol) in tert-butanol (30 ml), anhydrous sodium carbonate (1.65 g, 28.09 mmol) and water (3 ml) was added and the reaction mixture was refluxed. Solutions of sodium periodate (17.1, 50.0 mmol) and potassium permagnate (0.21 g, 4.2 mmol) in water (30 ml) was dropwise added to refluxed reaction mixture. The reaction mass was refluxed for an additional 3 hr. The precipitate was filtered washed with water and the filtrate was acidified with 5M HCl and extracted with dichloromethane. The organic phase was dried with anhydrous Na2SO4, filtered and filtrate was evaporated. The crude product was purified by silica gel column chromatography (MeOH:DCM 3:1) to obtain compound [17] as a yellow solid (1.8 g) with 56% of yield. MS (ESI) m/z (M+1) 349.

Step 2:

To a mixture of compound [17] (1.8 mg, 5.17 mmol) in acetic acid (5 ml) was added ammonium acetate (1.19 g, 15.5 mmol) and refluxed at 130° C. for 4 hr. The reaction mixture was evaporated to remove acetic acid and washed with water, neutralized with saturated and extracted with dichloromethane. The organic portion dried over $Na_2SO_4$, filter and filtrate was evaporated under vacuum. The crude product was purified by silica gel column chromatography (2% MeOH:DCM as a eluent) to give compound [18] as a light yellow solid (1.3 g) with 76% yield. MS (ESI) m/z (M+1) 330.

Step 3:

A mixture of Compound [18] (0.300 g, 0.91 mmol), p-toluenesulfonic acid monohydrate (13 mg), and ethylene glycol (2.5 ml) in benzene (250 ml) was refluxed with azeotropic removal of water for 8 hr. The mixture was diluted with ethyl acetate, washed with saturated sodium bicarbonate solution and brine, dried over sodium sulfate and concentrated under vacuum to obtain compound [19] as a light yellow solid (0.336 g) with 99% yield. MS (ESI) m/z (M+1) 374.

Step 4:

To a stirred solution of compound [19] (0.1 g, 0.268 mmol) in dry THF (100 ml) was added MeMgBr dropwise (0.134 ml, 0.40 mmol) at 0° C. and allowed for 6 hr at room temperature. The reaction mixture was quenched with saturated solution of ammonium chloride and extracted with ethyl acetate. Organic phase dried over sodium sulfate, filter and filtrate was evaporated. The crude residue was purified by silica gel column chromatography eluting with 2-3% MeOH:DCM to give compound [1026] as a light yellow solid (0.50 g, 48% yield). MS (ESI) m/z (M+H$^+$) 390

Step 5:

A solution of compound [1026] (0.05 g, 0.128 mmol) in acetone (10 ml) was treated with concentrated sulfuric acid (0.05 ml) at 0° C. The mixture was allowed to stirred for 2 hr. Reaction mixture was diluted with ethyl acetate and washed with saturated sodium carbonate solution and brine, dried over sodium sulfate and purified purified by silica gel column chromatography eluting with 2-3% MeOH:DCM to give compound [1008] as a light yellow solid (20 mg, 45% yield). MS (ESI) m/z (M+H$^+$) 346.

Step 6:

Compound [1025] was synthesized using the same procedure as mentioned in step 6 example 7a. Yield 80%. MS (ESI) m/z (M+1) 376.

Step 7:

Compound [1037] was synthesized using the same procedure as mentioned in step 5 example 7b. Yield 70%. MS (ESI) m/z (M+1) 332.

Step 8:

Compound [1038] was synthesized using the same procedure as mentioned in step 4 example 7b. Yield 75%. MS (ESI) m/z (M+1) 348.

Example 7c: Preparation of Compounds of the Present Invention

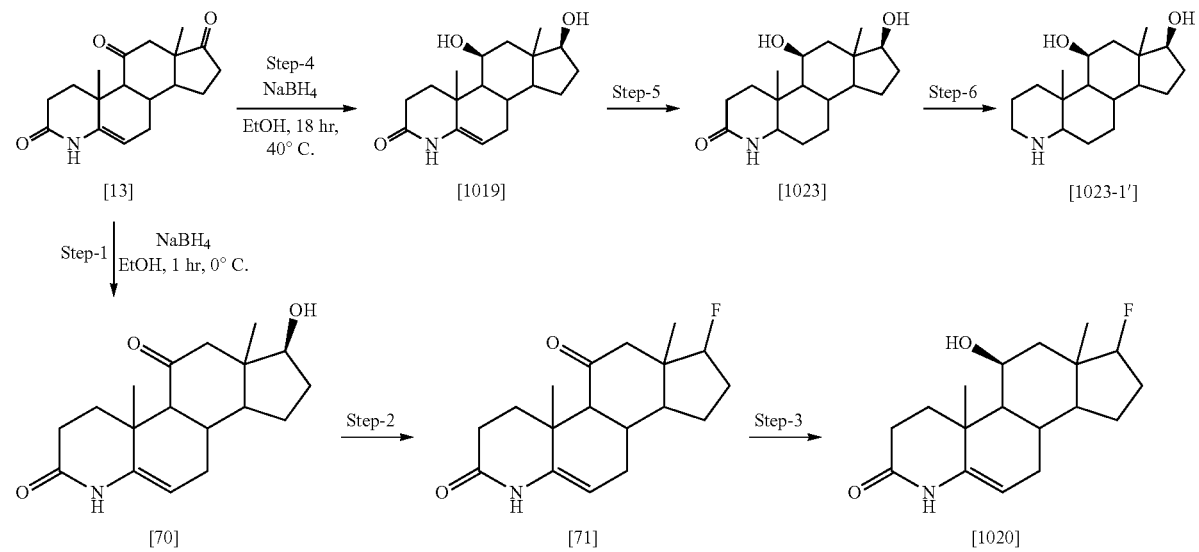

Step-1:

To a stirring solution of compound [13] (0.4 gm, 1.32 mmol) in EtOH (10 ml), NaBH$_4$ (0.05 gm, 1.32 mmol) was added portion wise. Reaction was stirred for additional 1 hour and progress of the reaction was monitored by TLC. After completion of reaction, 10 ml of acetone was added followed by addition of water (20 ml). Organic layer was extracted with ethyl acetate. Organic layer was dried over sodium sulfate and evaporated to get crude compound [70] (yield 90%), MS (ESI) m/z (M+1) 304.

Step-2:

Compound [70] (0.065 mg, 0.165) was dissolved in DCM, followed by addition of DAST (0.04 mg, 0.247) and stirred for one hour. Reaction was monitored by TLC and was diluted with water after completion. Organic layer was extracted with ethyl acetate and dried over sodium sulfate followed by evaporation under reduced pressure to get crude compound[71] (yield 75%), MS(ESI) m/z (M+1) 306.

Step-3:

To a solution of compound [71] (0.5 gm, 1.65 mmol) in EtOH (10 ml), NaBH4 (0.31 gm, 8.27 mmol) was added and reaction mixture was heated at 40° C. for 18 hrs. Reaction was monitored by TLC and quenched with 10 ml of acetone followed by a dilution with water. Organic layer was extracted with ethyl acetate and dried over sodium sulfate followed by evaporation to get crude compound [1020] as white solid (yield 80%), MS (ESI) m/z (M+1) 308

Step:4

Compound [1019] was synthesized using the same procedure as mentioned in step 3 example 7c at elevated temperature. Yield 80% MS (ESI) m/z (M+1) 306 Step:-5 Compound [1023] (50 mg) was dissolved in EtOH and Pd/C (5 mg) was added. Reaction was stirred under hydrogen pressure for 3 hrs to completion. Progress of the reaction was monitored with TLC. After completion reaction mass was filtered over celite layer and excess of solvent was evaporated under reduced pressure to get compound 1023 (yield 80%). MS (ESI) m/z (M+1) 308

Step 6:

To a solution of compound [1023] (0.2 gm, 0.651 mmol) in THF, was added LAH (85 mg, 2.28 mmol) and reaction mixture was stirred for 12 hrs. Progress of the reaction was monitored by TLC. Reaction was diluted with water and extracted with ethyl acetate. Organic layer was dried over NaSO4 and evaporated to get compound [1023-1']. Yield 85%. MS (ESI) m/z (M+1) 294

Example 7d: Preparation of Compounds of the Present Invention

Step:-1 To a solution of compound [13] (0.1 gm, 0.33 mmol) in DMF (2 ml), was added NaH (0.01 gm, 0.33 mm) at 0° C. Reaction mixture was stirred for 20 min at same temp, followed by addition of MeI (0.05 ml, 0.33 mmol). Reaction mass was stirred for additional 2-3 hrs at RT and progress of the reaction was monitored by TLC. After completion, reaction was quenched with water and extracted with ethyl acetate (100×2). Organic layer was dried over anhy sodium sulfate, and evaporated under vacuum, to get compound[74] (yield 90%).

MS (ESI) m/z (M+1) 316.

Step 2:

Compound [1022] was synthesized using the same procedure as mentioned in example 2b. Yield 80%. MS (ESI) m/z (M+1) 320.

Step 3:

Compound [13] (0.5 g, 1.65 mmol) was taken in MeOH: water (20 mL). Hydroxylamine hydrochloride (0.24 g, 3.46 mmol) was added to this solution followed by addition of sodium acetate (0.29 g, 3.63). The mixture was heated at 60° C. for 2 hrs. The solvent was evaporated and crude mass was taken in water (50 ml), extracted with ethyl acetate (3×100 ml). The organic layer was separated, dried over anhydrous Na2SO4, filtered and concentrated to obtain compound as off white solid (0.2 g, 95%). MS (ESI) m/z (M+1) 317.

Step 4:

Compound 1021 was synthesized using the same procedure as mentioned in step 4 example 7c. Yield 80%. MS (ESI) m/z (M+1) 319.

Step-5: The compound 1021 (0.2 g. 0.627 mmol) was taken in MeOH (50 ml). Pd/C (0.030 g) was added and reaction was stirred at room temperature under H2 atm (60 psi, Parr shaker). After completion, the excess of solvent was filtered, concentrated to obtain compound [1024] as light brown solid (0.17 g, 88%). MS (ESI) m/z (M+1) 307.

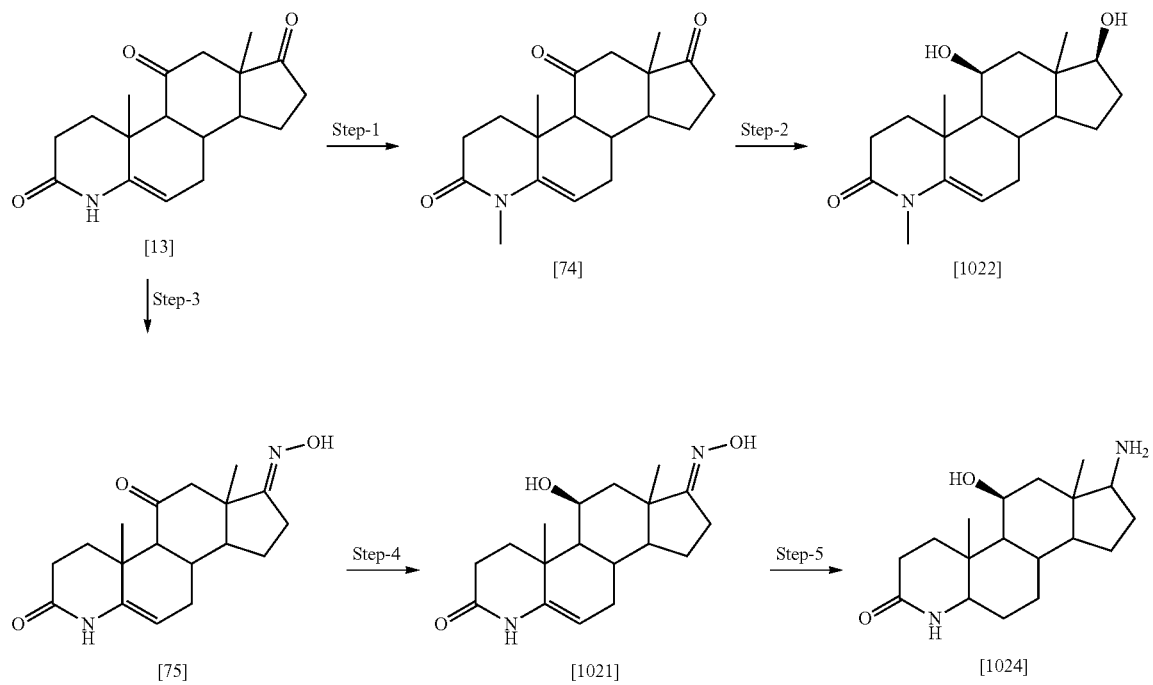

Example 7e: Preparation of Compounds of the Present Invention

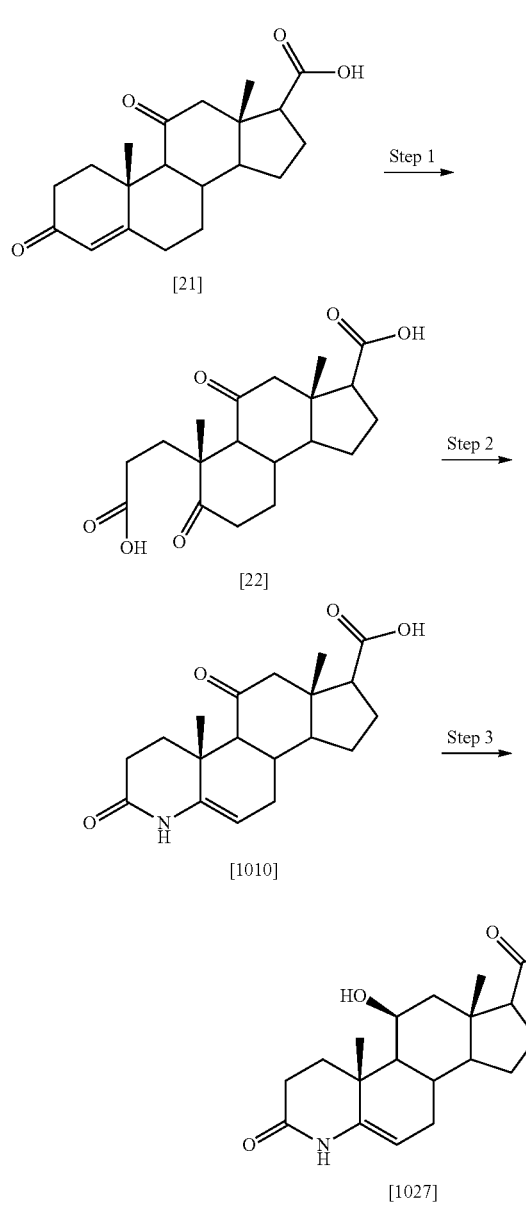

Example 8: Preparation of Compounds of the Present Invention

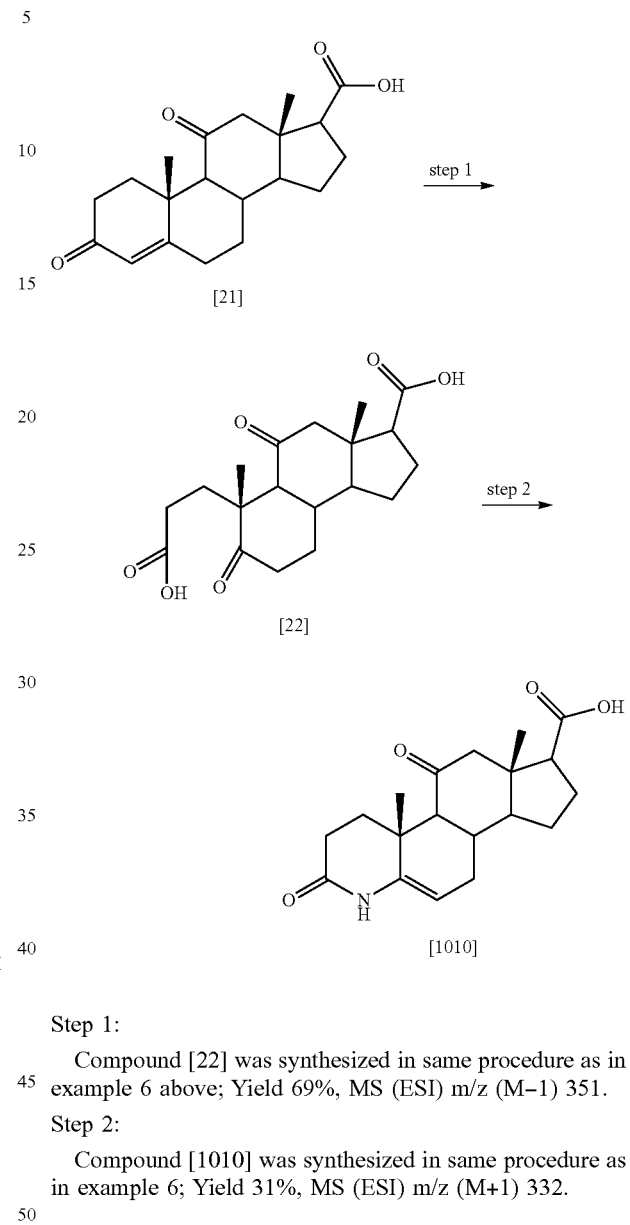

Step 1:
Compound [22] was synthesized in same procedure as in example 6 above; Yield 69%, MS (ESI) m/z (M−1) 351.

Step 2:
Compound [1010] was synthesized in same procedure as in example 6; Yield 31%, MS (ESI) m/z (M+1) 332.

Step 1:
The compound [22] was synthesized in same procedure as in example 6 above; Yield 69%, MS (ESI) m/z (M−1) 349.

Step 2:
The compound [1010] was synthesized in same procedure as in example 6; Yield 31%, MS (ESI) m/z (M+1) 334.

Step 4:
Compound [1027] was synthesized using the same procedure as mentioned in step 4 example 7c. Yield 76%; MS (ESI) m/z (M+1) 334.

A few illustrative examples of this series synthesized based on example 7a, 7b and 7c include 1005, 1008, 1017, 1018, 1020-1023, 1026, 1064, 1065

Example 9: Preparation of Compounds of the Present Invention

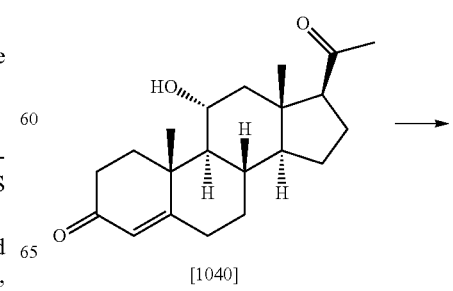

-continued

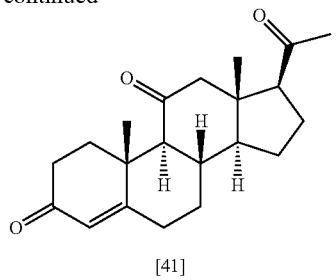

[41]

Step 1:
A solution of chromium trioxide (3.3 g, 33.3 mmol) in water (4 mL) was added dropwise to a solution of [1040] (10 g, 30.3 mmol) in acetic acid (300 ml). The reaction was stirred for 1.5 hr and quenched by the addition of methanol (30 mL), stirring for 0.5 hr. The mixture was concentrated by rotovap at 70° C., dissolved in ethyl acetate/methanol, washed with saturated sodium bicarbonate and brine, dried over sodium sulfate and concentrated to give 17-acetyl-10, 13-dimethyl-1,6,7,8,9,10,12,13,14,15,16,17-dodecahydro-2H-cyclopenta[a]phenanthrene-3,11-dione as an off white solid (9.0 g).

Step 2

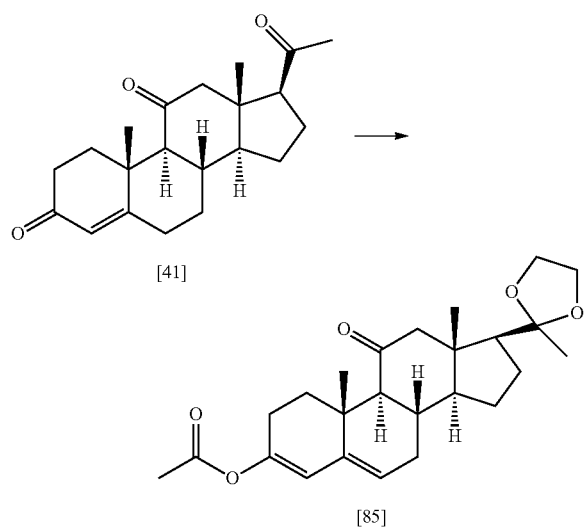

A solution of 70% formic acid (10 ul) in ethyl acetate (10 ml) is added to a solution of acetic anhydride (4.8 mL) in ethyl acetate (30 ml) and the final volume is brought up to 50 ml. [41] (500 mg, 1.5 mmol) was added and the reaction was stirred for 7 min then washed with saturated sodium bicarbonate, dried over sodium sulfate, and concentrated by rotovap at 70° C. The resulting oil was dissolved in methanol (10 ml), treated with pyridine (1 ml) and concentrated by rotovap to an oil which was dissolved in ethyl acetate, washed with 10% citric acid, saturated sodium bicarbonate, and brine, dried over sodium sulfate and concentrated to give the acetate diene as an oil which solidified on standing. A mixture of toluenesulfonic acid hydrate (110 mg) and ethylene glycol (2 ml) in benzene (25 ml) was refluxed with removal of water for 0.5 hr. A solution of the acetate diene in benzene (12 ml) was added and the reaction was refluxed for 1.5 hr. The mixture was diluted with ethyl acetate, washed with saturated sodium bicarbonate and brine, and dried over sodium sulfate. The crude product was purified by silica gel chromatography eluting with 20% to 30% ethyl acetate/hexanes to give acetic acid [85] as a white crystalline solid (420 mg).66% yield, and MS (ESI) m/z (M+1) 415.

Step 3

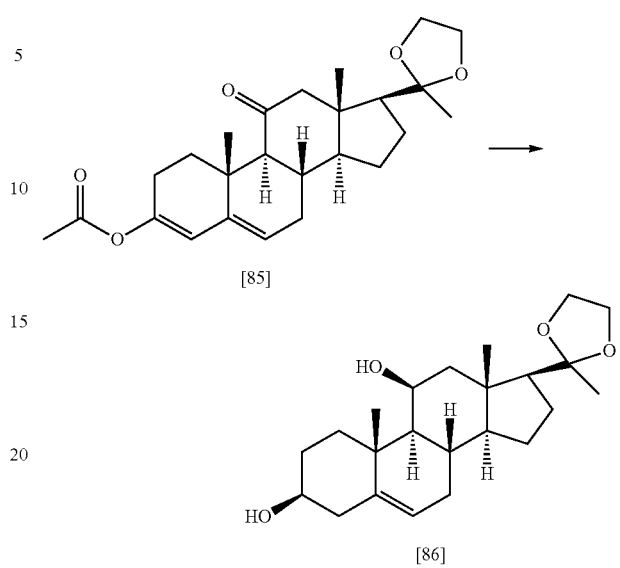

A chilled solution of acetic acid [85] (1.59 g) in 7:3 ethanol/THF (125 ml) was added dropwise to an ice cold suspension of sodium borohydride (2.5 g) in 80% ethanol (50 ml). The reaction was stirred in an ice bath for 8 hr then overnight allowing the ice bath to melt slowly. The reaction was quenched with 10% acetic acid and concentrated by rotovap until solid forms. The solid is filtered, washed with water and dried to constant weight to give [86] as a white solid (797 mg). A second crop is obtained by further concentrating the mother liquor (228 mg). MS (ES-API) m/z (M+H$^+$) 377.8.

Step 4:

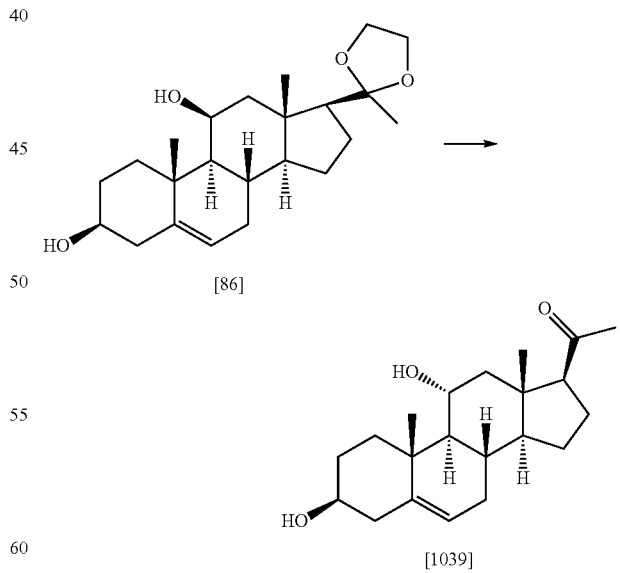

[86] (570 mg) and pyridinium p-toluenesulfonate (60 mg) were dissolved in 95% acetone (40 ml) and stirred overnight at RT. The reaction mixture was concentrated by rotovap until a solid appeared, filtered, washed with water and dried to constant weight to give as a white solid[1039] (319 mg).

The mother liquor was diluted with ethyl acetate, washed with citric acid and brine, dried over sodium sulfate and concentrated to give a second crop as a white solid (140 mg). 91% yield, MS (ESI) m/z (M+1) 353.

Example 10: Preparation of Compounds of the Present Invention

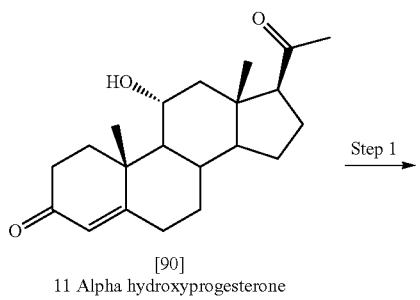

[90]
11 Alpha hydroxyprogesterone

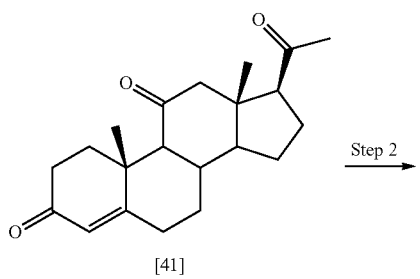

[41]

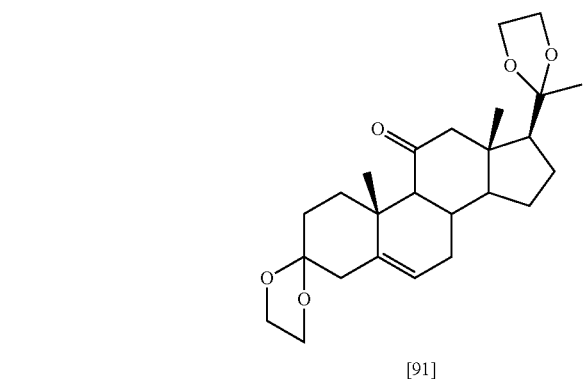

[91]

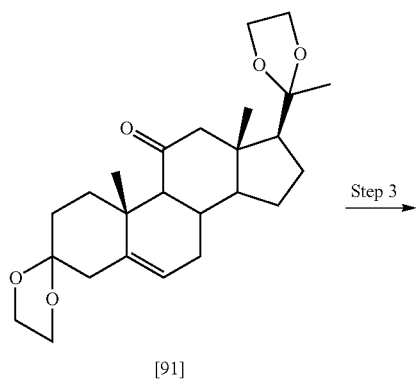

[91]

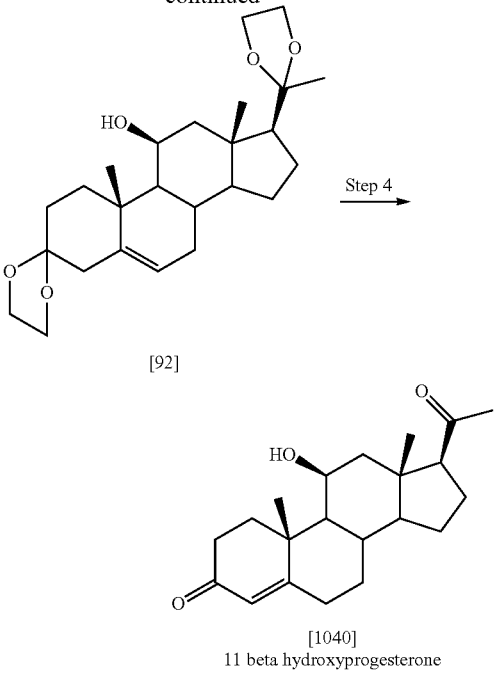

[92]

[1040]
11 beta hydroxyprogesterone

Step 1:

A solution of chromium trioxide (3.3 g, 33.3 mmol) in water (4 mL) was added dropwise to a solution of [90] (10 g, 30.3 mmol) in acetic acid (300 ml). The reaction was stirred for 1.5 hr and quenched by the addition of methanol (30 mL), stirring for 0.5 hr. The mixture was concentrated by rotovap at 70° C., dissolved in ethyl acetate/methanol, washed with saturated sodium bicarbonate and brine, dried over sodium sulfate and concentrated to give [41] as an off white solid (9.0 g).

Step 2:

A mixture of [41] (400 mg), toluenesulfonic acid hydrate (110 mg) and ethylene glycol (2 ml) in benzene (25 ml) was refluxed with removal of water for 0.5 hr. A solution of the acetate diene in benzene (12 ml) was added and the reaction was refluxed for 1.5 hr. The mixture was diluted with ethyl acetate, washed with saturated sodium bicarbonate and brine, and dried over sodium sulfate. The crude product was purified by silica gel chromatography eluting with 20% to 30% ethyl acetate/hexanes to give pure product [91] as a white crystalline solid (420 mg). M/Z 417

Step 3:

A chilled solution of [91] (0.59 g) in 7:3 ethanol/THF (125 ml) was added dropwise to an ice cold suspension of sodium borohydride (2.5 g) in 80% ethanol (50 ml). The reaction was stirred in an ice bath for 8 hr then overnight allowing the ice bath to melt slowly. The reaction was quenched with 10% acetic acid and concentrated by rotovap until a solid forms. The solid is filtered, washed with water and dried to constant weight to give pure [92] as a white solid (497 mg). MS(ES-API) m/z (M+H$^+$) 419.

Step 4:

A solution of compound [92] (0.25 g) in acetone (10 ml) was treated with concentrated sulfuric acid (0.05 ml) at 0° C. The mixture was allowed to stirred for 2 hr. Reaction mixture was diluted with ethyl acetate and washed with saturated sodium carbonate solution and brine, dried over sodium sulfate and purified purified by silica gel column chromatography eluting with 2-3% MeOH:DCM to give [1040] as a light yellow solid (0.180 mg). MS (ESI) m/z (M+H$^+$) 331

Example 11: Biological Testing of the Compounds of the Present Invention

The compounds of the present invention were tested for their activity on AMP KINASE. The activity on AMP KINASE was evaluated by quantitative fluorescent immunoenzymatic assay of AMP KINASE phosphorylation status in cultured cells. The 5-AMP-activated protein kinase (AMP KINASE) is a key sensor of intracellular energy balance. AMP KINASE is activated in response to an increase in the AMP/ATP ratio which can be caused by a number of factors such as muscle contraction, starvation, or hypoxia. AMP KINASE is a heterotrimeric protein complex comprising of α-(63 kDa), β-(38 kDa) and γ-(38 kDa) subunits. For each subunit, isoforms have been identified (α1, α2, β1, β2, γ1, γ2, γ3) which theoretically allow the formation of 12 different proteins. The α-subunit contains a serine/threonine kinase domain and the regulatory subunits contain binding sites for AMP and ATP (γ-subunit) and for glycogen (β-subunit). AMP KINASE is activated by phosphorylation on Thr-172 within the catalytic domain AMP binding results in a 2 to 5-fold increase in AMP KINASE activity compared to the basal level. Binding of AMP to the γ-subunit causes allosteric activation of the kinase and induces a conformational change in the kinase domain that protects AMP KINASE from dephosphorylation of Thr-172.

BioAssay Systems' cell-based ELISA measure phosphorylated AMP KINASE in whole cells and normalizes the signal to the total protein content. The antibody recognizes both α-subunits and, thus, can be used for cells from all tissues (human, mouse, rat). This simple and efficient assay eliminates the need for cell lysate preparation and can be used to study AMP KINASE regulation in short-term and long-term assays. In this assay, cells grown in 96-well plates are fixed and permeabilized in the wells. AMP KINASE phosphorylation (pAMPK) is measured using a fluorescent ELISA followed by total protein measurement in each well.

A few illustrative compounds of the present invention were tested at 10 nM and the AMPKinase activation of the compounds is listed at Table 2:

TABLE 2

AMP KINASE activation of the compounds of the present invention Biological data

| Compound No. | AMPKinase Activation at 10 nM |
|---|---|
| 1013 | 1.79 |
| 1014 | 1.80 |
| 1015 | 2.23 |
| 1016 | 2.38 |
| 1005 | 1.85 |
| 1017 | 2.08 |
| 1018 | 2.19 |
| 1019 | 2.23 |
| 1021 | 2.23 |
| 1022 | 2.87 |
| 1023 | 2.46 |
| 1025 | 2.11 |
| 1026 | 1.69 |
| 1008 | 1.97 |
| 1027 | 1.85 |
| 1030 | 1.51 |
| 1035 | 1.76 |
| 1026 | 2.17 |
| 1038 | 1.70 |

From Table 2, it may be seen that the compounds of the present invention are capable of activating AMPKinase, Example 12: Biological Activity of [1039] and [1040] in 3-(4,5-Dimethylthiazol-2-Yl)-2,5-Diphenyltetrazolium Bromide (MTT) Assay 6,000 BCAEC were seeded into clear 96-well flat bottom plates at 100 μl per well. After starvation, cells were treated for 48 hours with the corresponding compounds. Compounds were changed every 12 and 24 hours (with 100 μl per well of fresh medium). Following the treatment medium was aspirated from plates, and washed once with 100 μl HBSS, subsequently 100 μl per well 0.5 mg/ml MTT in phenol red-free DMEM was added. Plates were incubated for 1 hour at 37° C., and this was followed by aspiration of MTT solution, addition of 100 μl per well DMSO to dissolve formazan crystals, and incubation at 37° C. for 15 minutes. Mitochondrial function was quantified by absorbance was measured at 540 nm with background substraction at 670 nm using. After MTT absorbance measure, media was removed and cells quantify in each well as described elsewhere (Oliver et al, 1989) with some modifications. In brief, 100 μl of 10% formol saline to each well was added, and incubated at 4° C. for 24 hours. Next, formol solution was removed from the wells and 100 μl of filtered 0.1% (w/v) Methylene Blue in 0.01 M borate buffer (pH 8.5) was added to each well. After 30 minutes, excess dye was removed and washed off 3 times with 0.01 M borate buffer (pH 8.5). The stained dye on the cells was eluted by the addition of 100 μl of 1:1 (v/v) ethanol and 0.1 M-HCl in each well. The plates were then gently shaken and incubated for 15 minutes under a bench rocker. Absorbance was measured at 650 nm. The MTT/Methylene Blue ratio was used to quantify the mitochondrial function. Oliver M H, Harrison N K, Bishop J E, Cole P J, Lauren G J. A rapid and convenient assay for counting cells cultured in microwell plates: application for assessment of growth factors. J Cell Sci. 1989, 3:513-8.

Slot Blot Method.

Following treatment, bovine aortic endothelial cells grown in 12 well plates are scrapped in 50 μl of lysis buffer (1% Triton X-100, 20 mm Tris, 140 mm NaCl, 2 mm EDTA, and 0.1% SDS) with protease and phosphatase inhibitor cocktails (P2714 and P2850, Sigma-Aldrich) supplemented with 0.15 mm PMSF, 5 mm Na$_3$VO$_4$ and 3 mm NaF. Homogenates are passed through an insulin syringe five times, sonicated for 30 min at 4° C. and centrifuged (12,000 g) for 10 min. The total protein content is measured in the supernatant using the Bradford method. A total of 10-20 μg of protein are loaded into a pre-assembled slot blot apparatus to be transferred under vacuum onto polyvinyl membranes, incubated for 1 h in blocking solution (5% non-fat dry milk in TBS plus 0.1% Tween 20 (TBS-T)), followed by a overnight incubation at 4° C. with primary antibodies (oxidative phosphorylation complex I or GAPDH). Primary antibodies are diluted in TBS-T plus 5% non-fat dry milk Membranes are washed (3× for 5 min) in TBS-T and incubated 1 h at room temperature in the presence of HRP-conjugated secondary antibodies diluted in blocking solution. Membranes are again washed 3 times in TBS-T, and the immunoblots developed using an ECL Plus detection kit (Amersham-GE). Band intensities are digitally quantified using ImageJ software (http://www.nih.gov). Complex I values are normalized for loading differences using GAPDH after stripping and reprobing of the membrane. All Western blot images to be obtained will be within the linear range of X-ray film to ensure computer-assisted densitometry accuracy. The result is provided at Table 3.

TABLE 3

Biological Activity of [1039]

| Example # | MTT Assay<br>indicates ≤110% +<br>indicates >110% | Slot Blot Assay<br>indicates ≤150% HCAEC +<br>indicates >150% HCAEC |
|---|---|---|
| 1 | − | NT |
| 2 | + | + |

*NT—Not Tested

Example 13: AMP KINASE Activation of the Compounds [1039] and [1040]

AMP KINASE activation potential of the compounds was evaluated using cell based ELISA. Hepatoma (Hep G2) liver cells were maintained in a T 75 culture flask-containing 25 mM DMEM+10% fetal calf serum. The cells were maintained in a T 75 culture flask-containing medium (DMEM+ 10% fetal calf serum). On reaching a confluence of 70 to 80%, the cells were seeded in a 96 well plate at a density of 40,000 cells per well in 25 mM DMEM+10% FCS medium. The plates were then incubated at 37° C. with 5% $CO_2$ for 24 hours. Various concentrations of drugs were prepared in DMSO and diluted to required concentration with the medium and incubated at 37° C. with 5% $CO_2$ for 30 min and 1 h for Epicatechin analogs and 11-BHP analogs respectively. Metformin was used as positive control. Cells were fixed with 4% formaldehyde for 30 minutes at room temperature and washed three times with PBS containing 0.1% Triton X-100. Endogenous peroxidase was quenched with 1% $H_2O_2$ in PBS-T (0.1% Tween 20) for 30 minutes and washed three times in PBS-T. Cells were blocked with 1% BSA in PBS-T for 1 hour. The cells were incubated with 1:1000 dilution primary antibody (Phospho-AMPKα (Thr172) Rabbit mAb, Cell Signaling in PBS-T containing 5% BSA at 4° C. overnight. The cells were then washed three times with PBS-T for 5 minutes and incubated with 1:1000 dilution secondary antibody (Anti-rabbit IgG, HRP-linked Antibody, Cell Signaling) in PBS-T with 1% BSA for 1 hour at RT. Cells were washed three times with PBS-T for 5 minutes The cells were incubated with 100 µl TMB substrate solution for 30 minutes and the reaction was stopped with 100 µl of 2N $H_2SO_4$. Then the plate was read at 450 nM using ELISA plate reader and absorbance recorded. % activity was calculated using DMSO control as 100%. The result is provided at Table 4.

TABLE 4

Activation of AMP KINASE after 30 mins, over baseline of 100.

| | % pAMPK | | |
|---|---|---|---|
| Time Points | 2 mM Metformin | 0.1 nM [1039] | 0.1 nM [1040] |
| 30 m | 121 | 109 | 118 |

Figure 1B:
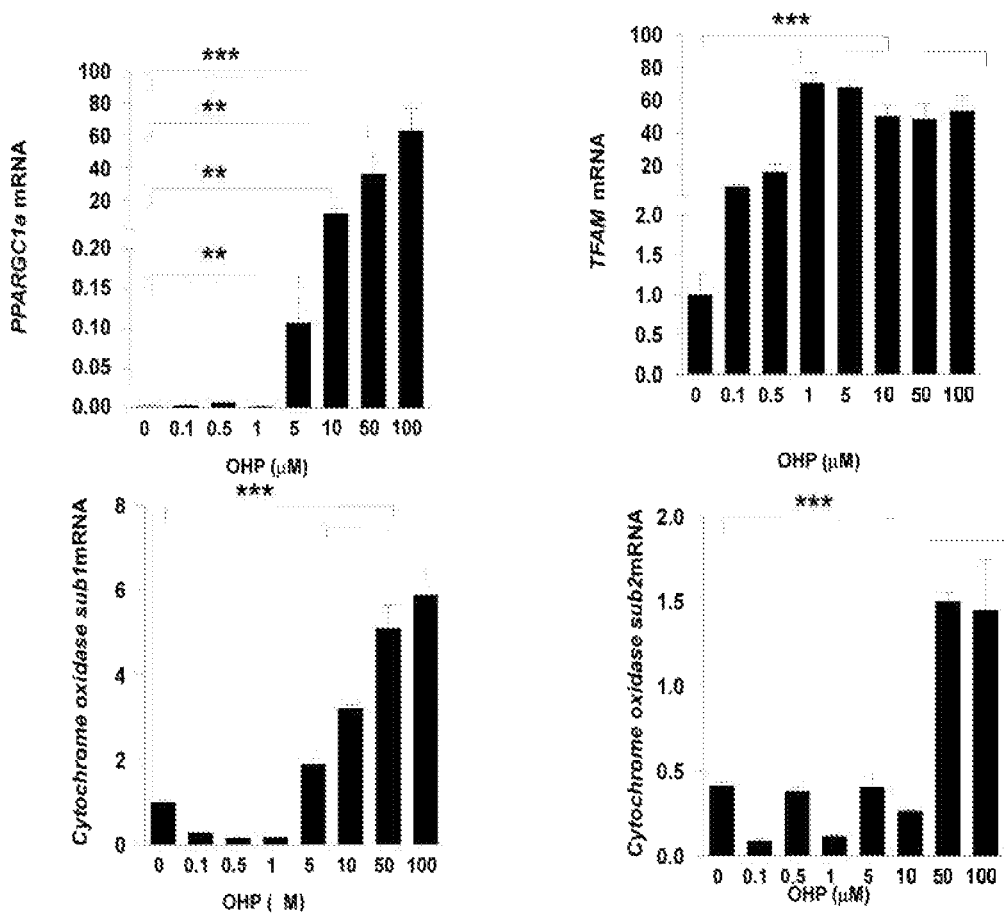

Example 14: Effects of [1039] on Human Coronary Artery Endothelial Cell Mitochondrial Oxidative Phosphorylation Complex I Protein Levels Cells were grown in Dulbecco's modified Eagle's media supplemented with fetal bovine serum (10%) to ~90% confluence. Cells were treated with either vehicle (water) or incremental doses of the agent (dissolved in water) for a total of 48 h (treatment was repeated at the 24 h time point). At the end of the experiment, cells were lysed in Western blot sample buffer. A fixed amount of protein (25 micrograms) was loaded onto a polyacrylamide gel and run for 1 h to allow for the electrophoretic separation of proteins. The gel was then transferred onto a polyvinyl membrane for incubation with blocking buffer prior to exposure to the 1ry antibody (anti-human complex I). Following a 1 h incubation at room temperature the membrane was washed and then exposed to the 2ry antibody for 1 h. after a second set of washes the membrane was incubated with an enhanced-chemiluminescence kit solution followed by exposure to X-ray film. The image obtain was used to quantitative changes in complex I protein levels as a function of compound dose. To normalize for loading differences the membrane was re-incubated (as above) with the subunit 6 ribosomal protein (S6RP) and exposed to X-ray film. Changes in values for complex I levels are normalized to differences in S6RP levels. All data are normalized to the values noted for cells treated with vehicle only (=100%). The results are presented at FIG. 1 a. From the figure, it can be clearly seen that compound [1039] causes mitochondrial biogenesis.

The OHP (another depiction of [1039]) effects on mRNA levels of genes involved in mitochondrial biogenesis PPARGC1a-PGC1a-, TFAM, and subunits 1 and 2 of cytochrome oxidase. HepG2 cells were exposed to increasing amounts of OHP (in uM) for 3 hours and then harvested for mRNA isolation (RNeasy kit, QIAGEN). mRNA were converted to cDNA (iScript, Bio-Rad) and amount of gene expression analyzed by real time PCR employing specific primers and using actin levels as the housekeeping gene. Data was plotted with graphpad Prism4 and analyze by ANOVA with ad hoc Tukey comparison between all columns (*P<0.05 and **P<0.01). The results are presented at FIG. 1b. From the figure, it can be clearly seen that compound [1039] expresses mitochondrial transcription factors as early as 3 hours of exposure.

Example 15: Activation of AMP Kinase by [1039]

Figure 2A:
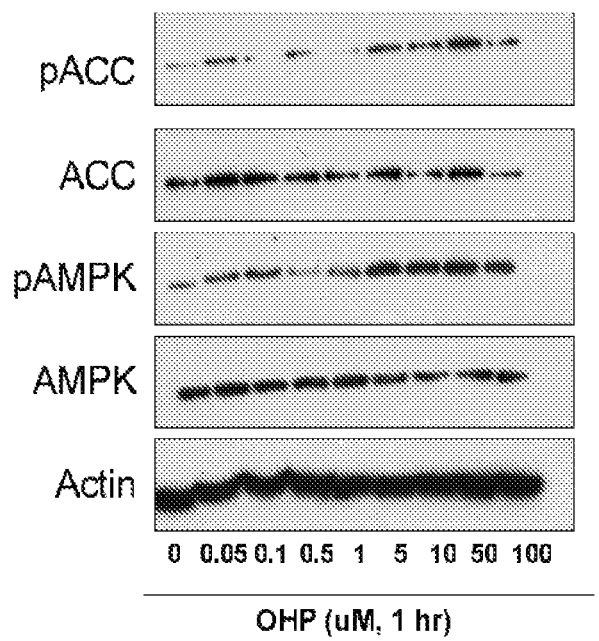
FIG. 2a depicts activation of AMP KINASE at 1 hour post-exposure by 11β-hydroxypregnenolone and FIG. 2b depicts activation APPL1 and translocation to the nucleus in 3 hr by 11β-hydroxypregnenolone.
Figure 2B:
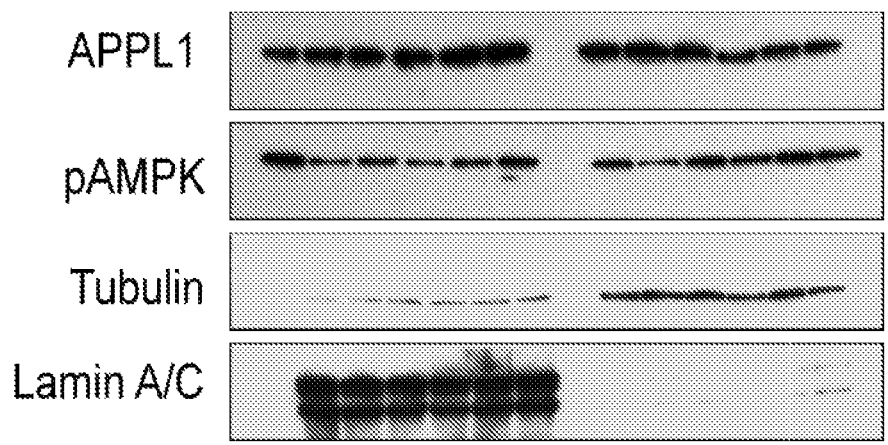

OHP effects on AMPKinase activation in HepG2 cells. HepG2 cells were exposed to increasing amounts of OHP (in uM) for 1 hour and then harvested for protein isolation employing a triton X-100 based lysis buffer containing phosphatase inhibitors (Phosstop, Roche). Protein levels were quantified (BCA assay) and 40 ug of protein loaded for detection of total AMPK, phosphorylated (active) AMPK, total and phosphorylated acetyl CoA carboxylase (ACC, AMPK target gene) and actin loading control. (RNeasy kit, QIAGEN). OHP effects on APPL1 nuclear translocation. HepG2 cells were exposed to increasing amounts of OHP (in uM) for 1 hour and nuclear and cytosolic fractions isolated (Biovision nuclear/cytosolic fractionation kit) and total protein quantified (BCA assay).40 ug of protein loaded for detection of total APPL1, phosphorylated (active) AMPK, tubulin (a marker of the cytosolic fraction) and 1 amin (a marker of the nuclear fraction). The results are presented at FIGS. 2a and 2b. From the figures, it can be seen that [1039] activates AMPkinase, even after 1 hour of exposure and activates APPL1 and causes its translocation to the nucleus.

Example 16: Activity of [1039] in Mitochondria

Figure 3A:
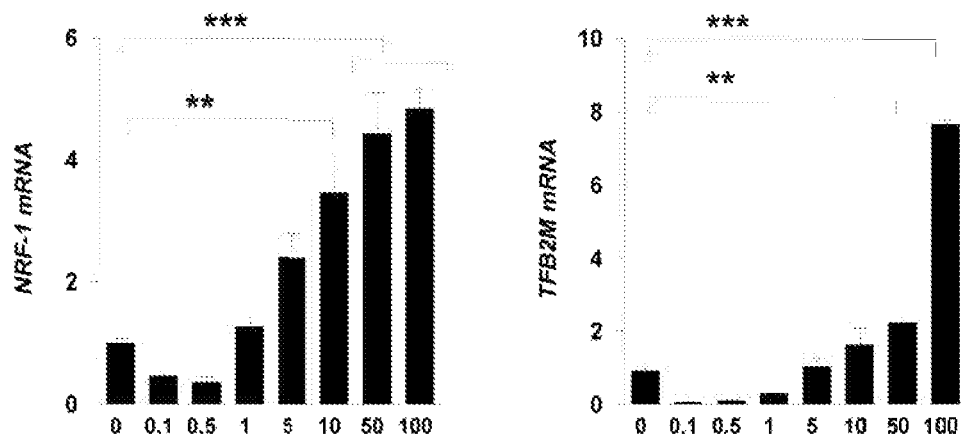
FIG. 3a depicts stimulation of expression of mitochondrial transcription factors at 3 hours post exposure (II) by 11β-hydroxypregnenolone and FIG. 3b depicts increase of mitochondrial DNA content at 24 hr post exposure by 11β-hydroxypregnenolone.
Figure 3B:
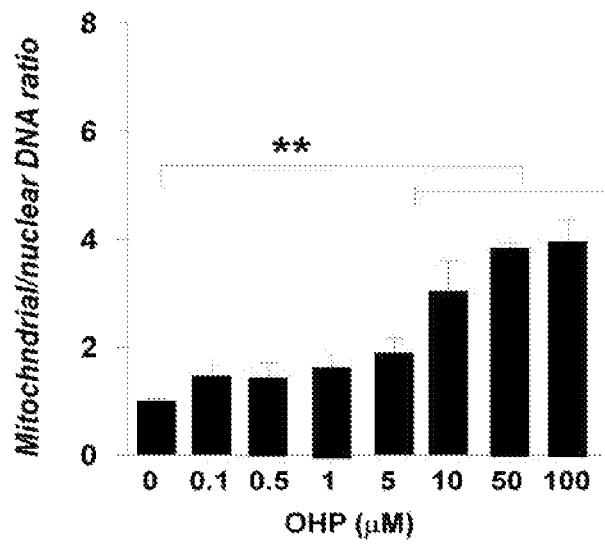

OHP effects on mRNA levels of genes involved in mitochondrial biogenesis Nrf1 and TFB2M. HepG2 cells were exposed to increasing amounts of OHP (in uM) for 3 hours and then harvested for mRNA isolation (RNeasy kit, QIAGEN). mRNA were converted to cDNA (iScript, Bio-Rad) and amount of gene expression analyzed by real time PCR employing specific primers and using actin levels as the housekeeping gene. HepG2 cells were exposed to increasing amounts of OHP (in uM) for 24 hours and then harvested for DNA isolation (Promega, Wizard DNA Isolation). Amount of DNA obtained quantified and analysis of mitochondrial DNA (a marker of mitochondrial mass) determined by measuring the number of copies of a mitochondrial gene codified by mitochondrial DNA (Cytochrome C) versus the number of copies of a mitochondrial gene codified by nuclear DNA (pyruvate dehydrogenase). Data was plotted with graphpad Prism4 and analyze by ANOVA with ad hoc Tukey comparison between all columns (*P<0.05 and **P<0.01). The results are depicted at FIGS. 3a and 3b. From the results, it can be seen that compound [1039] stimulates the expression of mitochondrial transcription factors and increases the DNA content of mitochondria.

Example 17: Effect of [1039] on Mitochondrial Oxidative Stress

Figure 4:
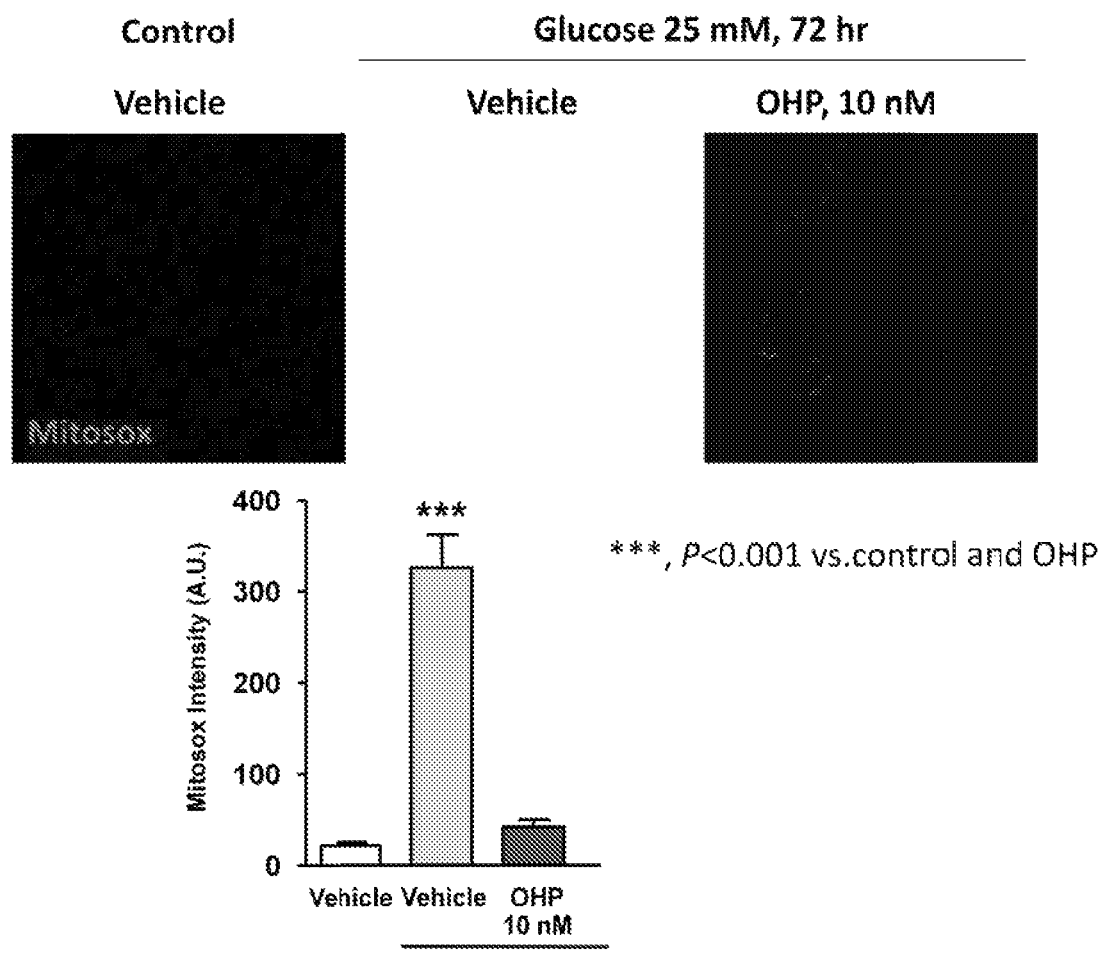
FIG. 4 depicts reduction of mitochondrial superoxide generation by 11β-hydroxypregnenolone.

HepG2 cells were exposed to vehicle or OHP (10 nM and mitochondrail superoxide production determined by confocal microscopy using the mitosox determination kit (molecular probes), intensity data was plotted with graphpad Prism4 and analyze by ANOVA with ad hoc Tukey comparison between all columns. See FIG. 4. From FIG. 4, it is clear that [1039] reduces superoxide generation in mitochondria.

Example 18: Effect of [1039] on Hepatic Gluconeogenesis and Fat Oxidation

Figure 5:
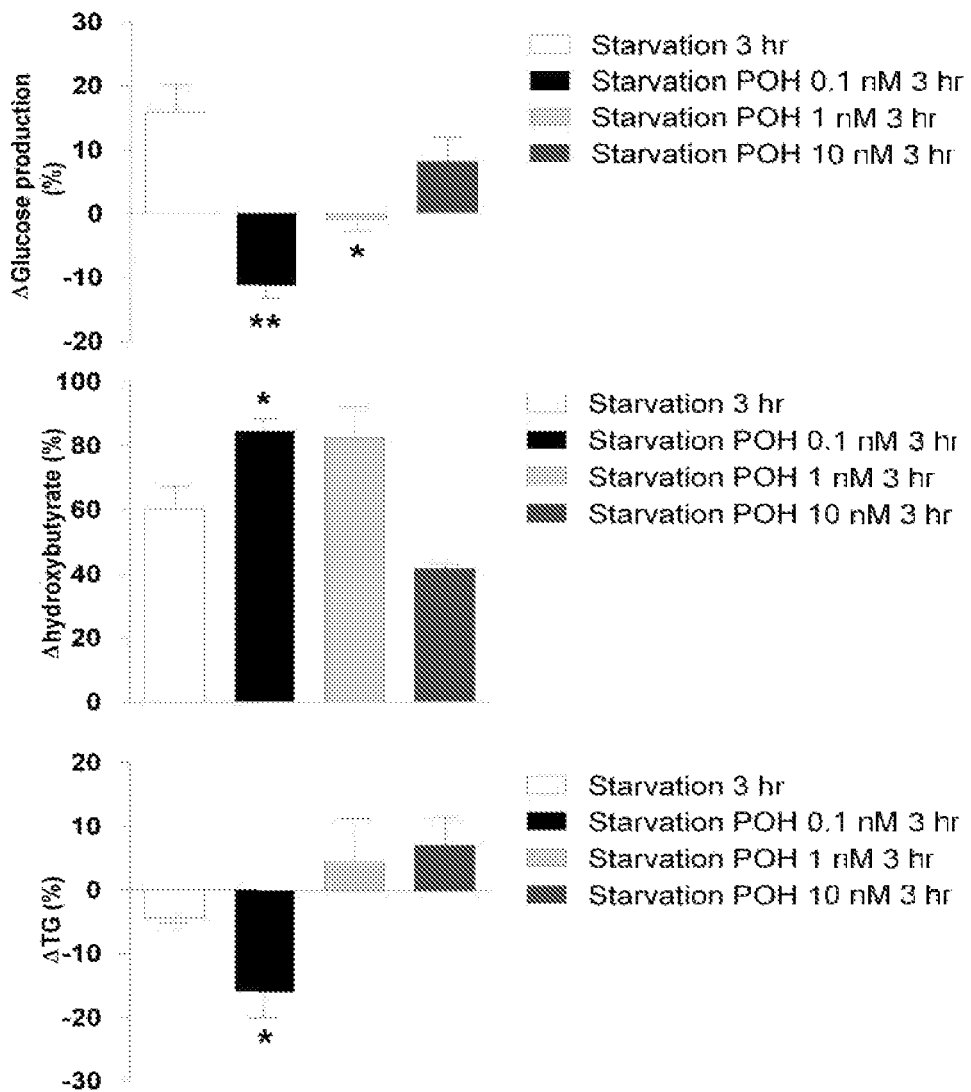
FIG. 5 depicts reduction of hepatic gluconeogenesis and stimulation of fat oxidation by 11β-hydroxypregnenolone.

HepG2 cells were exposed to serum-free media for 3 hours and then exposed to gluconeogenic factors (lactate and pyruvate 10:1 ratio) and stimulators (cAMP) in the presence of increasing concentrations of OHP (in nM). Intracellular glucose production—a marker of de novo gluconeogenesis-was determined enzimatically (biovision glucose determination kit), as well as intracellular beta-hydroxybutyrate levels (a marker of fat oxidation) and triglycerides (substrate for fat oxidation). Data was plotted with graphpad Prism4 and analyze by ANOVA with ad hoc Tukey comparison between all columns (*P<0.05 and **P<0.01). The results are depicted at FIG. 5. From FIG. 5, It can be clearly seen that [1039] reduces hepatic gluconeogenesis and stimulates oxidation of fat.

The invention claimed is:
1. A hydroxysteroid compound having formula (I):

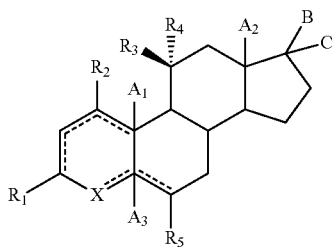

FORMULA I or a salt thereof, wherein is independently either a single bond, a double bond or a cyclopropyl ring, provided that adjacent double bonds are not allowed;

$A_1$, $A_2$, and $A_3$ are independently selected from the group consisting of hydrogen, hydroxyl, halogen, and $C_1$-$C_6$ alkyl;

B and C are each independently selected from the group consisting of hydrogen, hydroxyl, halogen, —$OR_6$, —$COR_6$, —$COOR_6$, —$OCOR_6$, —$CH_2OH$, —$CH_2OR_6$, —$CONHR_6$, —$CONR_6R_7$, —C(OH)$R_6R_7$, —$NHR_6$, —$NR_6R_7$, $C_1$-$C_{12}$ straight or branched chain alkyl, and 5-6 membered heterocycloalkyl;

wherein the $C_1$-$C_{12}$ straight or branched chain alkyl or 5-6 membered heterocycloalkyl is further optionally substituted with one or more substituents selected from the group consisting of halogen, $C_1$-$C_6$ alkyl, —$OR_6$, —$COOR_6$, —$CONHR_6$, —$OCOR_6$, =NOH, —$NR_6R_7$, —$NR_6COR_7$, 5-6 membered heterocycloalkyl, and $C_1$-$C_{12}$ alkyl substituted 5-6 membered heterocycloalkyl;

or B and C combine together to form =O or =$NOR_6$;

or B and C combine together with the carbon atom to which they are attached to form a 5-6 membered heterocycloalkyl, wherein said 5-6 membered heterocycloalkyl comprises one or more heteroatoms selected from the group consisting of O and N;

$R_1$ is selected from the group consisting of hydroxyl, =O, —$OR_6$, and -Otert-butyldimethylsilyl;

$R_2$ and $R_4$ are independently selected from the group consisting of hydrogen, deuterium, and $C_1$-$C_3$ straight or branched chain alkyl;

$R_3$ is hydroxyl;

wherein $R_3$ is in a beta configuration;

$R_5$ is hydrogen;

$R_6$ and $R_7$ are each independently selected from the group consisting of hydrogen, $C_1$-$C_{12}$ alkyl, —$NH_2$, —$(CH_2)_nNH_2$, 3-6 membered cycloalkyl, and 4-6 membered heterocycloalkyl;

X is selected from the group consisting of NH and $NR_6$; and n is 0 to 3;

wherein when $R_1$ is =O, then B and C are not —$CONHR_6$ or —$CONR_6R_7$.

2. The hydroxysteroid compound of claim 1, wherein the hydroxysteroid compound has formula (II):

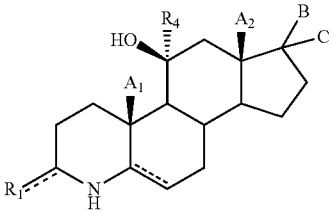

FORMULA II or a salt thereof, wherein:

is independently either a single bond, a double bond or a cyclopropyl ring, provided that adjacent double bonds are not allowed;

A₁ and A₂ are independently selected from the group consisting of hydrogen, halogen, and $C_1$-$C_6$ alkyl;

B and C are each independently selected from the group comprising consisting of hydrogen, hydroxyl, halogen, —COR₆, —COOR₆, —CH₂OH, —CH₂OR₆, —CONHR₆, —CONR₆R₇, —C(OH)R₆R₇, —NHR₆, —NR₆R₇, $C_1$-$C_{12}$ straight or branched chain alkyl, and 5-6 membered heterocycloalkyl;

wherein the $C_1$-$C_{12}$ straight or branched chain alkyl or 5-6 membered heterocycloalkyl is further optionally substituted with one or more substituents selected from the group consisting of halogen, $C_1$-$C_6$ alkyl, —OR₆, —COOR₆, —CONHR₆, —OCOR₆, =NOH, —NR₆R₇, —NR₆COR₇, 5-6 membered heterocycloalkyl, and $C_1$-$C_{12}$ alkyl substituted 5-6 membered heterocycloalkyl;

or B and C combine together to form =O or =NOR₆;

or B and C combine together with the carbon atom to which they are attached to form a 5-6 membered heterocycloalkyl, wherein the said 5-6 membered heterocycloalkyl, comprises one or more heteroatoms selected from the group consisting of O or N;

R₁ is selected from the group consisting of hydroxyl, =O, —OR₆, and —Otert—butyldimethylsilyl;

R₂ and R₄ are independently selected from the group consisting of hydrogen, deuterium, and $C_1$-$C_3$ alkyl;

R₆ and R₇ are each independently selected from the group consisting of hydrogen, $C_1$-$C_{12}$ straight or branched chain alkyl, —(CH₂)ₙNH₂, 3-6 membered cycloalkyl, and 4-6 membered heterocycloalkyl; and n is 0 to 3;

wherein when R₁ is =O, then B and C are not —CONHR₆ or —CONR₆R₇.

3. The hydroxysteroid compound of claim 1, or a salt thereof,
wherein:
A₁ and A₂ are each $C_1$-$C_6$ alkyl; and
A₃ is hydrogen.

4. The hydroxysteroid compound of claim 1, or a salt thereof, wherein:
B and C are each independently selected from the group consisting of hydrogen, halogen, —OCOR₆, —CH₂OH, —CH₂OR₆, —C(OH)R₆R₇, —NHR₆, —NR₆R₇, $C_1$-$C_{12}$ straight or branched chain alkyl, and 5-6 membered heterocycloalkyl.

5. The hydroxysteroid compound of claim 1, or a salt thereof, wherein:
B and C are each independently selected from the group consisting of —OR₆, —COR₆, and —COOR₆.

6. The hydroxysteroid compound of claim 1, wherein:
B and C are each independently selected from the group consisting of hydrogen and 5-6 membered heterocycloalkyl;
wherein the 5-6 membered heterocycloalkyl is further optionally substituted with a $C_1$-$C_6$ alkyl.

7. The hydroxysteroid compound of claim 1, or a salt thereof, wherein:
B and C combine together to form =O or =NOR₆.

8. The hydroxysteroid compound of claim 1, or a salt thereof, wherein:
B and C combine together with the carbon atom to which they are attached to form a 5-6 membered heterocycloalkyl, wherein said 5-6 membered heterocycloalkyl comprises one or more heteroatom selected from the group consisting of O and N.

9. The hydroxysteroid compound of claim 1, wherein:
R₁ is =O.

10. The hydroxysteroid compound of claim 1, or a salt thereof, wherein:
R₂ and R₄ are hydrogen.

11. The hydroxysteroid compound of claim 1, or a salt thereof, wherein:
R₂ is hydrogen; and
R₄ is $C_1$-$C_3$ alkyl.

12. The hydroxysteroid compound of claim 1, or a salt thereof,
wherein:
A₁ and A₂ are each $C_1$-$C_6$ alkyl;
A₃ is hydrogen;
R₁ is =O; and
R₂ is hydrogen.

13. A pharmaceutical composition comprising the compound of claim 1 or a pharmaceutically acceptable salt thereof.

14. A hydroxysteroid compound selected from the group consisting of:
  i. (4aR,5S,6aS)-5-hydroxy-4a,6a-dimethyl-4,4a,4b,5,6, 6a,9,9a,9b,10-decahydro-1H-indeno[5,4-f]quinoline-2, 7(3H,8H)-dione;
  ii. (4a'R,5'S,6a'S)-5'-hydroxy-4a',5',6a'-trimethyl-3',4', 4a',4b',5',6',6a',8',9',9a',9b',10'-dodecahydrospiro[[1,3] dioxolane-2,7'-indeno[5,4-f]quinolin]-2'(1'H)-one;
  iii. (4aR,5S,6aS)-4,4a,4b,5,6,6a,9,9a,9b,10-decahydro-5-hydroxy-4a,6a-dimethyl-1H-indeno[5,4-f]quinoline-2, 7(3H,8H)-dione;
  iv. (4aR,5S,6aS)-7-acetyl-4,4a,4b,5,6,6a,7,8,9,9a,9b,10-dodecahydro-5-hydroxy-4a,5,6a-trimethyl-1H-indeno [5,4-f]quinolin-2(3H)-one;
  v. (4aR,6aS)-2,3,4,4a,4b,5,6,6a,7,8,9,9a,9b,10-tetradecahydro-4a,6a-dimethyl-2,5-dioxo-1H-indeno[5,4-f]quinoline-7-carboxylic acid;
  vi. (4a'R,5'S,6a'S)-5'-hydroxy-4a',6a'-dimethyl-3',4',4a', 4b',5',6',6a',8',9',9a',9b',10'-dodecahydrospiro[[1,3]dioxolane-2,7'-indeno[5,4-f]quinolin]-2'(1'H)-one;
  vii. (4aR,5R,6aS)-5-hydroxy-4a,5,6a-trimethyl-4,4a,4b,5, 6,6a,9,9a,9b,10-decahydro-1H-indeno[5,4-f] quinoline-2,7(3H,8H)-dione;
  viii. (4aR,5S,6aS)-5,7-dihydroxy-4a,6a-dimethyl-4,4a, 4b,5,6,6a,7,8,9,9a,9b,10-dodecahydro-1H-indeno[5,4-f]quinolin-2(3H)-one;
  ix. (4aR,5S,6aS)-7-fluoro-5-hydroxy-4a,6a-dimethyl-4, 4a,4b,5,6,6a,7,8,9,9a,9b,10-dodecahydro-1H-indeno [5,4-f]quinolin-2(3H)-one;
  x. (4aR,5S,6aS,Z)-5-hydroxy-7-(hydroxyimino)-4a,6a-dimethyl-4,4a,4b,5,6,6a,7,8,9,9a,9b,10-dodecahydro-1H-indeno[5,4-f]quinolin-2(3H)-one;
  xi. (4aR,5S,6aS)-5,7-dihydroxy-1,4a,6a-trimethyl-4,4a, 4b,5,6,6a,7,8,9,9a,9b,10-dodecahydro-1H-indeno[5,4-f]quinolin-2(3H)-one;
  xii. (4aR,5S,6aS)-5,7-dihydroxy-4a,6a-dimethyltetradecahydro-1H-indeno[5,4-f]quinolin-2(3H)-one;
  xiii. (4aR,5S,6aS)-7-amino-5-hydroxy-4a,6a-dimethyltetradecahydro-1H-indeno[5,4-f]quinolin-2(3H)-one;
  xiv. (4aR,5S,6aS,7S)-5-hydroxy-4a,6a-dimethyl-7-(2-methyl-1,3-dioxolan-2-yl)-4,4a,4b,5,6,6a,7,8,9,9a,9b, 10-dodecahydro-1H-indeno[5,4-f]quinolin-2(3H)-one;
  xv. (4aR,5S,6aS,7S)-5-hydroxy-4a,5,6a-trimethyl-7-(2-methyl-1,3-dioxolan-2-yl)-4,4a,4b,5,6,6a,7,8,9,9a,9b, 10-dodecahydro-1H-indeno[5,4-f]quinolin-2(3H)-one;
  xvi. (4aR,5S,6aS,7S)-5-hydroxy-4a,6a-dimethyl-2-oxo-2, 3,4,4a,4b,5,6,6a,7,8,9,9a,9b,10-tetradecahydro-1H-indeno[5,4-f]quinoline-7-carboxylic acid;

xvii. (4aR,5S,6aS,7S)-7-acetyl-5-hydroxy-4a,6a-dimethyl-4,4a,4b,5,6,6a,7,8,9,9a,9b,10-dodecahydro-1H-indeno[5,4-f]quinolin-2(3H)-one;

xviii. (4aR,5S,6aS,7S)-5-hydroxy-7-(2-hydroxypropan-2-yl)-4a,6a-dimethyl-4,4a,4b,5,6,6a,7,8,9a,9b,10-dodecahydro-1H-indeno[5,4-f]quinolin-2(3H)-one;

xix. (4aR,5S,6aS,7S)-5-hydroxy-4a,6a-dimethyl-7-(2-methyl-1,3-dioxolan-2-yl)-4,4a,4b,5,6,6a,7,8,9,9a,9b,10-dodecahydro-1H-indeno[5,4-f]quinolin-2(3H)-one; and xx. (4aR,5S,6aS,7S)-5-hydroxy-4a,6a-dimethyl-2-oxo-2,3,4,4a,4b, 5,6,6a,7,8,9,9a,9b, 10-tetradecahydro-1H-indeno[5,4-f]quinoline-7-carboxylic acid, or a pharmaceutically acceptable salt or stereoisomer each thereof.

* * * * *